(12) United States Patent
Gallagher et al.

(10) Patent No.: US 12,702,391 B2
(45) Date of Patent: Aug. 11, 2026

(54) MINIMALLY INVASIVE NO TOUCH (MINT) PROCEDURE FOR HARVESTING THE GREAT SAPHENOUS VEIN (GSV), ENDOSCOPIC ASVAL TECHNIQUE AND ASSISTED PIN STRIPPING OF SUPERFICIAL GSV, HYDRODISSECTION-BASED ENDOSCOPIC VEIN HARVESTING (EVH) SYSTEM, VENOUS HYDRODISSECTOR, RETRACTOR AND TIP ADAPTER FOR USE WITH FLEXIBLE CYSTOSOPE AND ADAPTED CYSTOSCOPE SYSTEM

(71) Applicant: PJPG LLC, Bayshore, NY (US)

(72) Inventors: John F. Gallagher, Bay Shore, NY (US); Pamela M. Gallagher, Bay Shore, NY (US); Paul J. Gallagher, San Diego, CA (US); Kaitlin E. Masciello, Commack, NY (US)

(73) Assignee: PJPG LLC, Bay Shore, NY (US)

( * ) Notice: Subject to any disclaimer, the term of this patent is extended or adjusted under 35 U.S.C. 154(b) by 654 days.

(21) Appl. No.: 18/084,374

(22) Filed: Dec. 19, 2022

(65) Prior Publication Data

US 2023/0172593 A1 Jun. 8, 2023

Related U.S. Application Data

(60) Continuation-in-part of application No. 16/909,704, filed on Jun. 23, 2020, now Pat. No. 11,540,817, (Continued)

(51) Int. Cl.
*A61B 17/02* (2006.01)
*A61B 17/00* (2006.01)
(Continued)

(52) U.S. Cl.
CPC ........ *A61B 17/00008* (2013.01); *A61B 17/02* (2013.01); *A61B 17/0218* (2013.01); (Continued)

(58) Field of Classification Search
CPC ...... A61B 17/00008; A61B 17/320016; A61B 2017/320024; A61B 2017/320044; (Continued)

(56) References Cited

U.S. PATENT DOCUMENTS

2001/0056224 A1* 12/2001 Renner .............. A61B 1/00075 600/139
2010/0292533 A1* 11/2010 Kasahara ............... A61B 1/012 600/104
(Continued)

*Primary Examiner* — Eduardo C Robert
*Assistant Examiner* — Christina Negrellirodriguez
(74) *Attorney, Agent, or Firm* — John F. Vodopia; Thomas A. O'Rourke; James Bongiorno

(57) ABSTRACT

A method of atraumatically hydrodissecting and maintaining endothelial function and structure of a vascular target includes forming an incision in tissue proximate one end to realize an insertion space, inserting a distal end of a cannula and/or endoscope into the insertion space and while visualizing the vascular target, ejecting a hydrodissecting fluid from the distal end of the cannula and/or endoscope to substantially separate or dissect the vascular target from the surrounding tissue, while advancing the distal end through the space as it is enlarged by the hydrodissecting fluid, to a distal target end of the vascular target. The hydrodissecting fluid is formulated to minimize or prevent formation of microthrombi in the hydrodissected vascular target. The hydrodissecting fluid is a water-based vascular graft treatment solution and can include any of a balance salt solution, a metallic salt solution, such as Plasma-Lyte® A, a vascular graft treatment solution, such as Duragraft® solution, L-Arginine, aspirin and low molecular weight heparin.

16 Claims, 37 Drawing Sheets

Related U.S. Application Data which is a continuation of application No. 16/208,915, filed on Dec. 4, 2018, now abandoned, which is a division of application No. 16/039,115, filed on Jul. 18, 2018, now Pat. No. 10,687,793.

(60) Provisional application No. 63/328,413, filed on Apr. 7, 2022, provisional application No. 63/300,206, filed on Jan. 17, 2022, provisional application No. 62/683,376, filed on Jun. 11, 2018, provisional application No. 62/640,892, filed on Mar. 9, 2018, provisional application No. 62/533,714, filed on Jul. 18, 2017.

(51) Int. Cl.
*A61B 17/32* (2006.01)
*A61B 17/3203* (2006.01)
*A61B 90/30* (2016.01)
*A61B 90/00* (2016.01)

(52) U.S. Cl.
CPC .. *A61B 17/320016* (2013.01); *A61B 17/3203* (2013.01); *A61B 90/30* (2016.02); *A61B 2017/320024* (2013.01); *A61B 2017/320044* (2013.01); *A61B 2017/320056* (2013.01); *A61B 2017/32035* (2013.01); *A61B 2090/306* (2016.02); *A61B 2090/309* (2016.02); *A61B 90/361* (2016.02); *A61B 2217/007* (2013.01)

(58) Field of Classification Search
CPC ........ A61B 2017/320056; A61B 90/30; A61B 2090/306
USPC ......... 600/141–146, 184–246; 285/181–185; 606/108, 41, 45, 50, 171, 150
See application file for complete search history.

(56) References Cited

U.S. PATENT DOCUMENTS

2013/0158345 A1* 6/2013 Majlessi ............... A61M 19/00 606/159
2014/0316211 A1* 10/2014 Hermle ............ A61B 17/00008 600/210

* cited by examiner 1
1
1
1
102
104

102
104

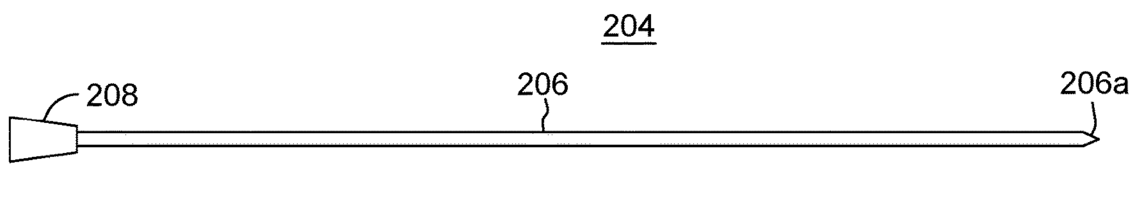
FIG. 5A
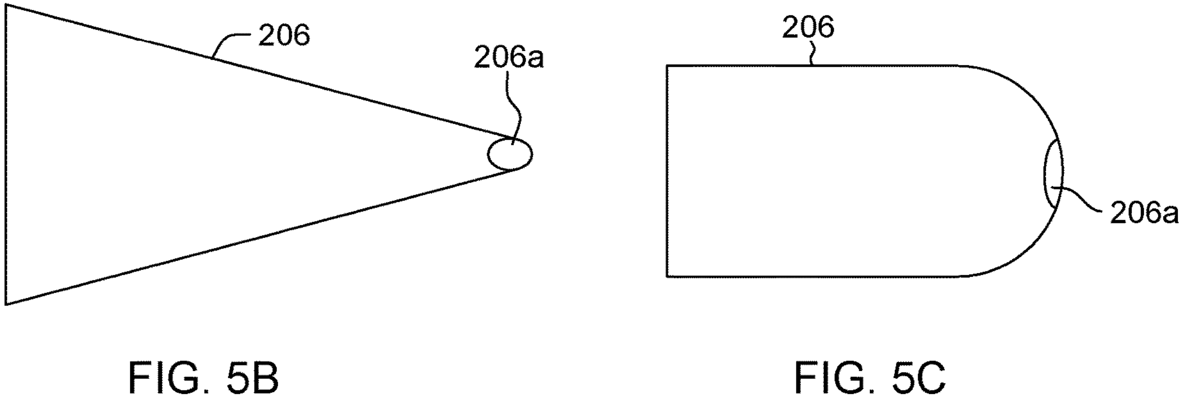
FIG. 5B
FIG. 5C

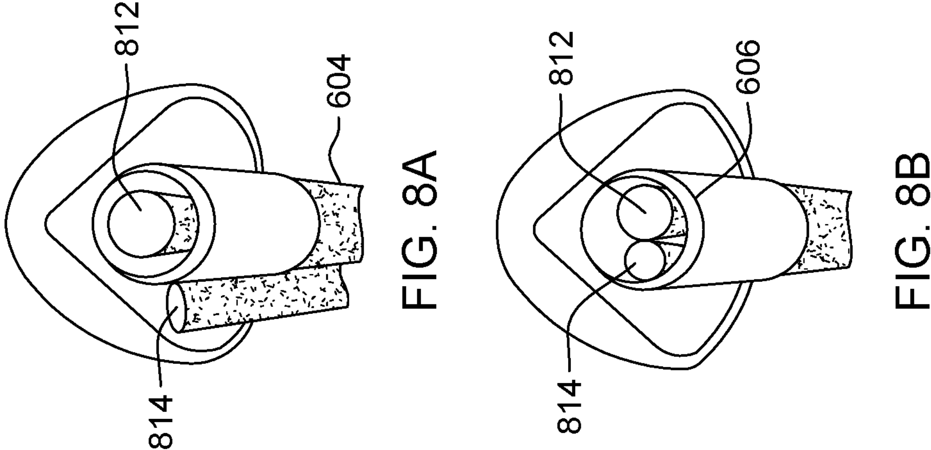
FIG. 8A
FIG. 8B
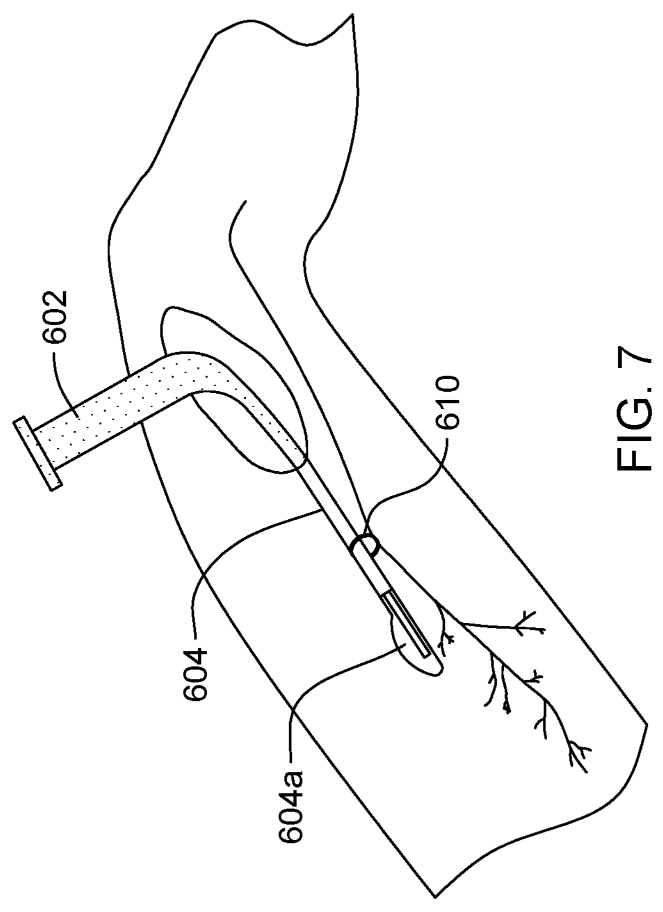
FIG. 7

3 CM INCISION IN KNEE

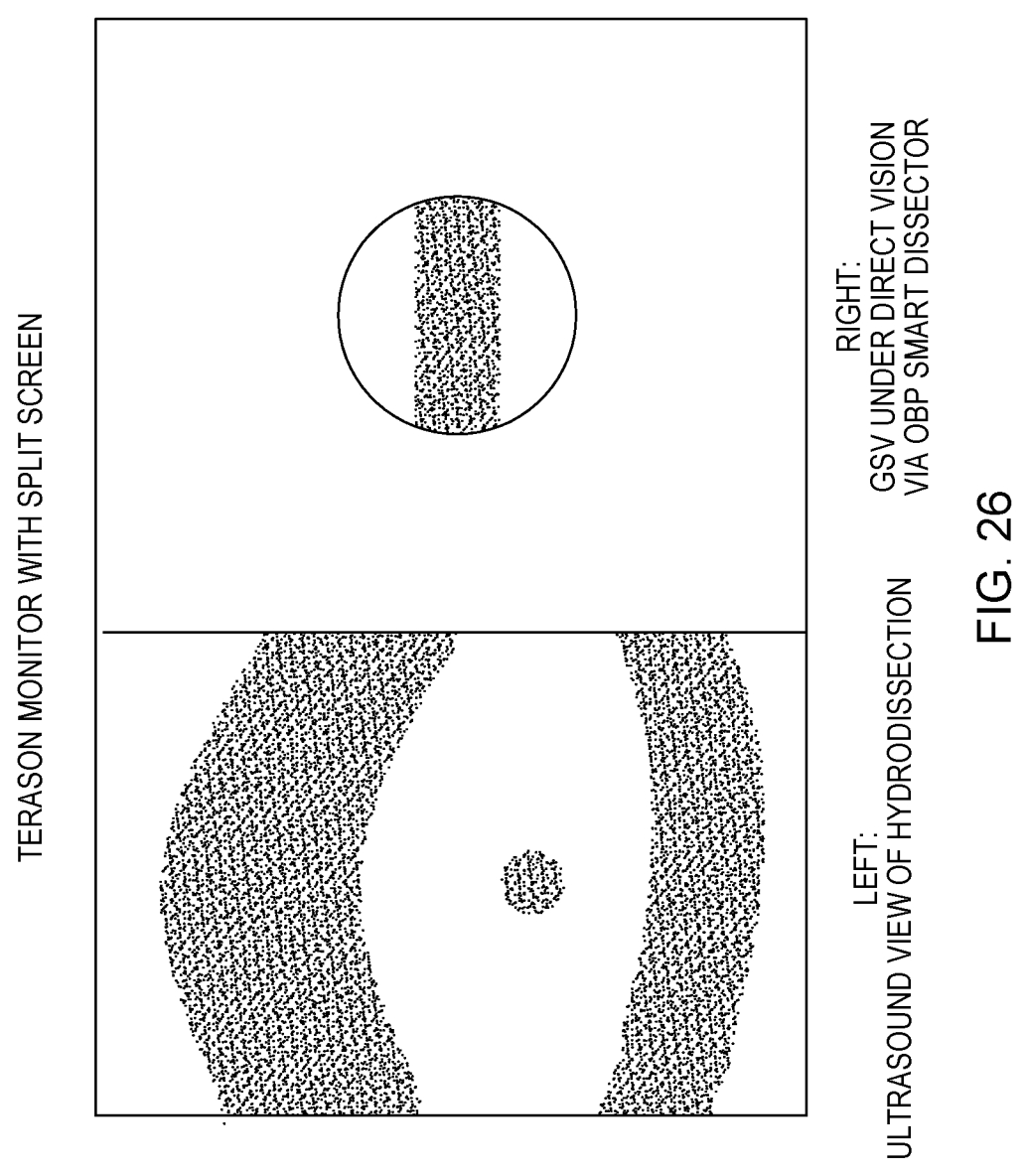

TERASON MONITOR WITH SPLIT SCREEN

LEFT:
ULTRASOUND VIEW OF HYDRODISSECTION

RIGHT:
GSV UNDER DIRECT VISION
VIA OBP SMART DISSECTOR

FIG. 26

MINIMALLY INVASIVE NO TOUCH (MINT) PROCEDURE FOR HARVESTING THE GREAT SAPHENOUS VEIN (GSV), ENDOSCOPIC ASVAL TECHNIQUE AND ASSISTED PIN STRIPPING OF SUPERFICIAL GSV, HYDRODISSECTION-BASED ENDOSCOPIC VEIN HARVESTING (EVH) SYSTEM, VENOUS HYDRODISSECTOR, RETRACTOR AND TIP ADAPTER FOR USE WITH FLEXIBLE CYSTOSOPE AND ADAPTED CYSTOSCOPE SYSTEM

CROSS-REFERENCE TO RELATED APPLICATIONS

This application is a continuation-in-part (CIP) of U.S. patent application Ser. No. 16/909,704 filed on Jun. 23, 2020, which is a continuation of U.S. patent application Ser. No. 16/208,915 filed on Dec. 4, 2018 and abandoned Nov. 13, 2020, which is a divisional of U.S. patent application Ser. No. 16/039,115 filed on Jul. 18, 2018 and issued as U.S. Pat. No. 10,687,793 on Jun. 23, 2020, which claims the benefit of U.S. Provisional Application Nos. 62/533,714 filed on Jul. 18, 2017, 62/640,892 filed on Mar. 9, 2018 and 62/683,376 filed on Jun. 11, 2018. This CIP application also claims the benefit of U.S. Provisional Application Nos. 63/300,206 filed on Jan. 17, 2022 and 63/328,413 filed on Apr. 7, 2022. The entire disclosures of these five (5) applications are incorporated herein by reference.

BACKGROUND OF THE INVENTION

There are currently two vascular epidemics present in the population of the United States. Atherosclerosis directly leads to coronary artery disease (CAD), which is the leading cause of death in the United States today. Coronary artery bypass grafting (CABG) may be described simply as a procedure for bypassing severely damaged or non-functional coronary arteries using a grafted portion of a healthy vein or artery harvested from the patient under treatment, such as the great saphenous vein (GSV), explained in greater detail below. Atherosclerosis also is the cause of peripheral arterial disease (PAD), which leads to significant disability, increased amputation rates, and death. A second epidemic facing the United States is a very high incidence of damaged vasculature, such as significant varicose veins.

In greater detail, current medical technology enables bypass or replacement of severely damaged vasculature, such as coronary arteries, with veins, such as the great saphenous vein (GSV). The replacement veins are harvested using various conventional harvesting techniques, which, before the inventive techniques, apparatus and systems disclosed hereby, may be said to be less than optimal. For example, trauma to the GSV (and its branches) during harvesting is likely to occur during blunt dissection of the GSV. Blunt dissection of the GSV occurs in most endoscopic harvesting carried out in cooperation with known endoscopic harvesting (EVH) systems. This trauma is especially severe when the EVH is carried out by inexperienced operators.

One known EVH technique employs a 2 cm incision at the level of the knee to expose the GSV. The GSV then is bluntly dissected from its surrounding connective tissue, including a well-developed laminar ligament which attaches the GSV to the underlying muscular fascia. The blunt force, however, results in patency rates of the GSV harvested by EVH being inferior to those harvested by the open vein technique (OVH). To address this issue, Domingos R Souza, Department of Cardiovascular and Thoracic Surgery, Orebro University Hospital, Orebro, Sweden, developed a so called "No Touch" technique. In this "No Touch" technique, the GSV is harvested with a cuff of surrounding tissue so that the GSV itself is never touched during the harvesting procedure. This "No Touch" technique has resulted in five year patency rates of 90% for GSVs harvested in this manner. The "No Touch" technique, however, is technically demanding and results in local leg wound complications as high as 50%. The "No Touch" technique, therefore, has not been widely adopted.

SUMMARY OF THE INVENTION

This patent application discloses an improvement over the known endoscopic vein harvest (EVH) methods presently used to harvest the GSV for use in CABG procedures in a way that increases long term patency of the grafted portions as well as an improvement in the treatment of varicose veins that preserves the GSV in the body of the patient under treatment so that it will be available in an optimized state for harvesting in the future, if required.

In certain embodiments of the invention, a minimally invasive method for dissecting a greater saphenous vein (GSV) from surrounding tissues is provided. The method comprises inserting one of a needle and a hydrodissector into a patient's body so that a tip of the one of the needle and the hydrodissector is placed in a predetermined position adjacent to the GSV to be dissected from surrounding tissues, and injecting fluid at a substantially constant volumetric flow rate from the one of the needle and the hydrodissector while moving the one of the needle and the hydrodissector along a predetermined length of the GSV to cause dissection of the GSV from the surrounding tissues, wherein hydrodissected GSV is suitable for subsequent harvesting for use in surgical bypass procedures. In certain embodiments, the predetermined position adjacent the GSV is 1-2 mm away from an upper surface of the GSV closest to the patient's skin or 1-2 mm away from a lower surface of the GSV furthest from the patient's skin.

In certain embodiments, the fluid injected in the injecting step comprises tumescent fluid including one or more of: isotonic sodium bicarbonate solution, Balanced Salt Solution with a pH of 7.4, isotonic saline solution, balanced salt solution, such as Plasma-Lyte® solution by Baxter Laboratories Inc., and an endothelial damage inhibitor solution comprising glutathione, ascorbic acid and L-arginine. In certain embodiments, the tumescent fluid further comprises one or more medications including one or more of: aspirin, low-molecular weight heparin, one or more vasodilators, nitroglycerine, Endothelin A receptor antagonist, folic acid, angiotensin II receptor antagonist, Spermine/NO, Losartan, Perilyl alcohol, Superoxide dismutase, Antitissue factor antibody, Verapamil, Ursolic acid, Rapamycin, Azathioprin, Paclitaxel, C-type natriuretic peptide, Leoligin, Papaverine, platelet rich plasma and stem cells. In some embodiments, these medications may be applied to the GSV after performing the hydrodissection.

In some embodiments, the GSV is hydrodissected from the surrounding tissues using one or more needles, and the inserting and injection steps are successively performed for each of a plurality of portions of a length of the GSV to cause dissection the respective portion of the length of the GSV from the surrounding tissues. In some embodiments, a plurality of needles is used, and each respective portion of the length of the GSV is hydrodissected from the surrounding tissues using a respective one of the plurality of needles.

In certain embodiments, the steps of inserting and injecting are performed under one or more of: (1) ultrasound guidance for visualizing the one of the needle and the hydrodissector and (2) direct vision of the one of the needle and the hydrodissector using an image capturing device provided on or in proximity with the one of the needle and the hydrodissector. The ultrasound guidance for visualizing one of the needle and hydrodissector may be performed using a portable ultrasound device. When direct vision is used, the direct vision may be obtained by capturing live images using the image capturing device provided at the tip of the hydrodissector.

In certain embodiments, the minimally invasive method further comprises, before performing the inserting and injecting steps, making an incision in a patient's extremity; and positioning a barrier with an access port through the incision so as to cover and seal the incision, wherein the inserting step comprises inserting the one of the needle and the hydrodissector through the access port into the predetermined position adjacent the GSV to be dissected from the surrounding tissues. In some embodiments, the barrier is formed from fluid-tight material and comprises one of a diaphragm and a tissue occluder, and the access port comprises a fluid-tight one way valve.

The present invention is also directed to a surgical bypass method that includes the above minimally invasive method, and further includes harvesting the hydrodissected GSV by exposing the hydrodissected GSV, dividing side branches of the hydrodissected GSV and dividing proximal and distal ends of the hydrodissected GSV, and using harvested GSV for bypass surgery. In some embodiments, the harvesting step further comprises lifting the hydrodissected GSV after exposing the hydrodissected GSV and prior to dividing the side branches.

The present invention is also directed to an ambulatory selective varicose vein ablation method comprising the above minimally invasive method and further including exposing the hydrodissected GSV; and ligating incompetent perforator and varicosed vein side branches. The ambulatory selective varicose vein ablation method may further include applying drug eluting stents to the hydrodissected GSV and ligated vein side branches for delivering one or more of drug therapy, stem cell therapy and gene therapy to the GSV.

The present invention is further directed to harvesters and hydrodissectors used for the above methods. In some embodiments, the invention provides a harvester for harvesting a vein, the harvester comprising a handle, a blade extending at an angle from the handle, and one or more hook-shaped attachments configured to couple with the blade so as to protrude from a surface of the blade, the one or more hook-shaped attachments being configured for lifting of a vein during a vein harvesting procedure. The hook-shaped attachment may be a C-shaped attachment or a U-shaped attachment and may be detachable from the blade. In certain embodiments, the blade includes a plurality of coupling mechanisms along a length of the blade, each of the coupling mechanisms being configured to selectively couple with one of the hook-shaped attachments. In some embodiments, the blade has a first surface facing away from the handle and an opposing second surface, and the one or more hook-shaped attachments are configured to couple to the first surface of the blade. In other embodiments, the blade comprises a tubular shaft and a spoon-shaped tip at a distal end of the tubular shaft and the one or more hook-shaped attachments are configured to couple to one or more of the tubular shaft and the spoon-shaped tip.

The harvester of the present invention may also include one or more ports provided at the distal end of the tubular shaft, each of the one or more ports is configured to be coupled to one of a fluid supply, a gas supply and a vacuum. In some embodiments, the harvester further includes an image capturing assembly for capturing images of an operating field, with the image capturing assembly including an image capturing device provided at a tip of the blade. The tip of the blade may be spoon-shaped including a concave surface and an opposing convex surface, and the image capturing device may be provided on the concave surface of the spoon-shaped tip.

In another embodiment, the present invention provides a harvester for harvesting a vein, the harvester comprising a handle, a blade extending at an angle from the handle and having a spoon-shaped tip at a distal end of the blade, the spoon-shaped tip including a concave surface and a convex surface, and an image capturing assembly for capturing images of an operating field, the image capturing assembly including an image capturing device provided on the concave surface of the spoon-shaped tip.

In yet another embodiment, the present invention provides a harvesting retractor for harvesting a vein, which includes a handle, a blade extending at an angle from the handle and having a first surface facing away from the handle and an opposing second surface, and a tunnel formed on the first surface of the blade and extending along a portion of the blade configured for accommodating a direct visualization device therein. The harvesting retractor may also include a channel along the first surface of the blade and a channel cover covering the channel, wherein the channel is configured for one or more of: removal of fluids from operating field, removal of debris from the operating field, removal of smoke from the operating field, injecting fluid into the operating field and infusing gas into the operating field, and wherein the channel and the tunnel extend along the first surface of the blade and are parallel to one another.

The present invention also provides a hydrodissector for hydrodissecting a vein, the hydrodissector comprising a handle, a shaft extending from the handle at an angle and including a tip at a distal end thereof, at least one port configured to be coupled to a fluid supply for supplying fluid at a substantially constant pressure, and provided at the distal end of the shaft, and an image capturing assembly configured to provide direct visualization of the vein during hydrodissection. In certain embodiments, the image capturing assembly comprises an image capture device encased by the tip of the shaft. The image capture device includes a lens, an image sensor and/or one or more light sources. The image capturing assembly may also include a power source for powering the image capture device, said power source being provided in one of the tip, the shaft and the handle.

In certain embodiments, the tip of the shaft is transparent and the image capture device is positioned inside the tip so that an optical axis of the image capture device is angled relative to a lengthwise axis of the tip so as to allow direct viewing of the vein to be hydrodissected. In some embodiments, the tip has a substantially cylindrical shape and an angled end so that a first surface of the tip is longer than an opposing second surface of the tip.

In certain embodiments, the at least one port is external and adjacent to the first surface of the tip, while in other embodiments, the at least one port is provided in the tip and is configured to be coupled the fluid supply via one of the shaft and a conduit extending inside the shaft. The at least one port may include a first port configured to be coupled to a fluid supply and having a size between 14 and 22 gauge, and in some embodiments, a second port may be provided for coupling to a vacuum.

In certain embodiments, the tip is configured to rotate relative to the shaft. In some embodiments, the shaft is configured to rotate relative to the handle. In some embodiments, the tip of the shaft is removable from a body of the shaft and interchangeable with one or more second tips, while in other embodiments the shaft is removable from the handle and interchangeable with one or more second shafts. The second tip may be a spoon-shaped tip configured for retracting tissues and for harvesting the vein, and a second image capturing device may be provided on the spoon-shaped tip. The second shaft may include a second tip, such as a spoon-shaped tip, and may be configured to releasably couple with the handle and to convert the hydrodissector into a harvester for harvesting the vein and may have a second image capturing device is provided on the second tip.

In an embodiment, the invention provides an endoscopic hydrodissector for atraumatically hydrodissecting a vascular target. The hydrodissector has a handle, an elongate endoscopic tube attached to or integral with the handle at a proximal end, a working tip attached to or integral with a distal end of the elongate endoscopic tube, a working port or opening at the working tip; and a fluid ejection port arranged at the working tip in fluid-flow connection to a fluid conduit or channel in an inner volume of the elongate endoscopic tube, the fluid conduit of channel in fluid flow connection to a supply of fluid for ejection from the fluid ejection port to dissect and substantially separate the vascular target from tissues surrounding the vascular target, creating a space therebetween. The elongate endoscopic tube and the working tip with the ejection port are configured for insertion into an incision space created by making an incision into the tissue proximate a targeted end of the vascular target. The elongate endoscopic tube and working tip with the ejection port is controlled to move through the incision space and the created space realized by hydrodissecting to separate the vascular target from the surrounding tissues and enlarging the created space as the elongate endoscopic tube and the working tip with ejection port are controlled to traverse the created space to a targeted end of the vascular target. The fluid is formulated to minimize or prevent formation of microthrombi in the endothelium of the hydrodissected vascular target.

The fluid is formulated to maintain endothelial function and structure of the vascular target. The fluid may include Duragraft® vascular graft treatment solution. The Fluid may further include at least one of aspirin and low molecular weight heparin. The fluid ejection port and/or the fluid conduit or channel and/or the fluid supply preferably is configured to provide sufficient pressure and velocity to the fluid to effect the hydrodissection. The endoscopic hydrodissector may also include a short blunt tip (SBT) cannula with an insertion end, a fluid seal end, and a side port configured to slide on an outer surface of the elongate endoscopic tube, wherein the insertion end extends partially into the incision to form a fluid barrier to prevent or minimize fluid leakage. Fluid may be input to the initial space and/or the created space via the side port. Preferably, the working tip includes an image capture assembly or device for direct visualization of the vascular target and initial and inner spaces during hydrodissection. Either the image capture assembly or device includes illumination means or an illumination means is arranged at the working tip.

In one form, the elongate endoscopic tube is rigid. In that case, the rigid, elongate endoscopic tube is maintained in a rigid cannula such that the working tip with ejection port is maintained at a distal end of the cannula. The fluid supply is maintained in a housing, separate from the cannula, and detachably connected to an outer surface of the cannula and wherein the fluid is ejected from an ejection port arranged, not in the working tip but in a distal end of the housing proximate the working tip.

In one form, the elongate endoscopic tube is flexible. In that case, the flexible, elongate endoscopic tube includes a bending portion comprising a first end and a second end, wherein the first end of the bending portion is attached to or integral with a truncated end of the flexible, elongate endoscopic tube and wherein the second end of the bending portion is attached to or integral with the working tip. The handle includes a manipulating means coupled or connected to the bending portion, to control articulation of the bending portion and a position of the working tip with the ejection port and thereby a direction to which the fluid is directed to effect hydrodissection. And the hydrodissector can further include an end cover formed as a housing that is detachably connected over the working tip with ejection port and to the endoscopic tube such that the working tip with ejection port and image capture device are positioned within an inner volume of the housing. The end cover housing includes a port or opening through which hydrodissecting fluid is ejected to effect dissection and further includes a window through which an image signal is captured by the image capture device. The hydrodissector further includes a portable display detachably connectable to the image capture device for processing the captured image signal and displaying an image of the target vessel, the insertion space, the created space and the surrounding tissues during hydrodissection.

In an embodiment, the invention provides a method of atraumatically hydrodissecting a vascular target while maintaining an endothelial function and structure of the vascular target. The method includes acts of forming an incision in tissue proximate a proximal target end of the vascular target to realize an insertion space, inserting a distal end of an endoscope or a cannula with an endoscope arranged in an inner volume thereof, into the insertion space, visualizing the vascular target and ejecting a hydrodissecting fluid from a distal end of the endoscope or the cannula with the endoscope arranged in the inner volume thereof, into the incision space to substantially separate or dissect the vascular target from the surrounding tissues and creating a created space, and advancing the distal end through the created space as the created space is enlarged along a course of the target vessel in reliance upon the ejecting hydrodissecting fluid and the visualizing, to a distal target end of the vascular target, wherein the hydrodissecting fluid is formulated to minimize or prevent formation of microthrombi in the endothelium of the hydrodissected vascular target.

Preferably, the hydrodissecting fluid is a water-based vascular graft treatment solution. The water-based vascular graft treatment solution preferably comprises water and one or more of Plasma-Lyte® solution, a vascular graft treatment solution, such as Duragraft® vascular graft treatment solution by Marizyme Inc., L-Arginine, aspiring and low molecular weight heparin. The method may include dividing and/or sealing incompetent or varicosed branches of the vascular target and substantially closing about the incision about the endoscope or cannula while some portion of hydrodissecting fluid is maintained as a tumescent fluid or is otherwise introduced into the created space remains in the created space. And the method may include harvesting the vascular target by dividing and/or ligating all branches and the proximal and distal target ends and atraumatically extracting the vascular target from the created space.

The above features of the invention as well as the features recited in the claims are interchangeable and may be combined and used in any configuration with one another. Further features and advantages will be apparent to those skilled in the art after reviewing the drawings and detailed description provided herein.

BRIEF DESCRIPTION OF THE DRAWINGS

FIGS. 5A-5C show an exemplary venous hydrodissector for use in the process of FIG. 4;

FIG. 7 shows another version of a retractor for use during the harvesting of the GSV;

FIGS. 8A and 8B show a front view of different versions of the retractor of FIG. 7;

FIG. 26 shows an exemplary split screen visualization which includes an ultrasound view of hydrodissection and a direct visualization view'

DETAILED DESCRIPTION OF THE INVENTION

Figures 1A, 1B:
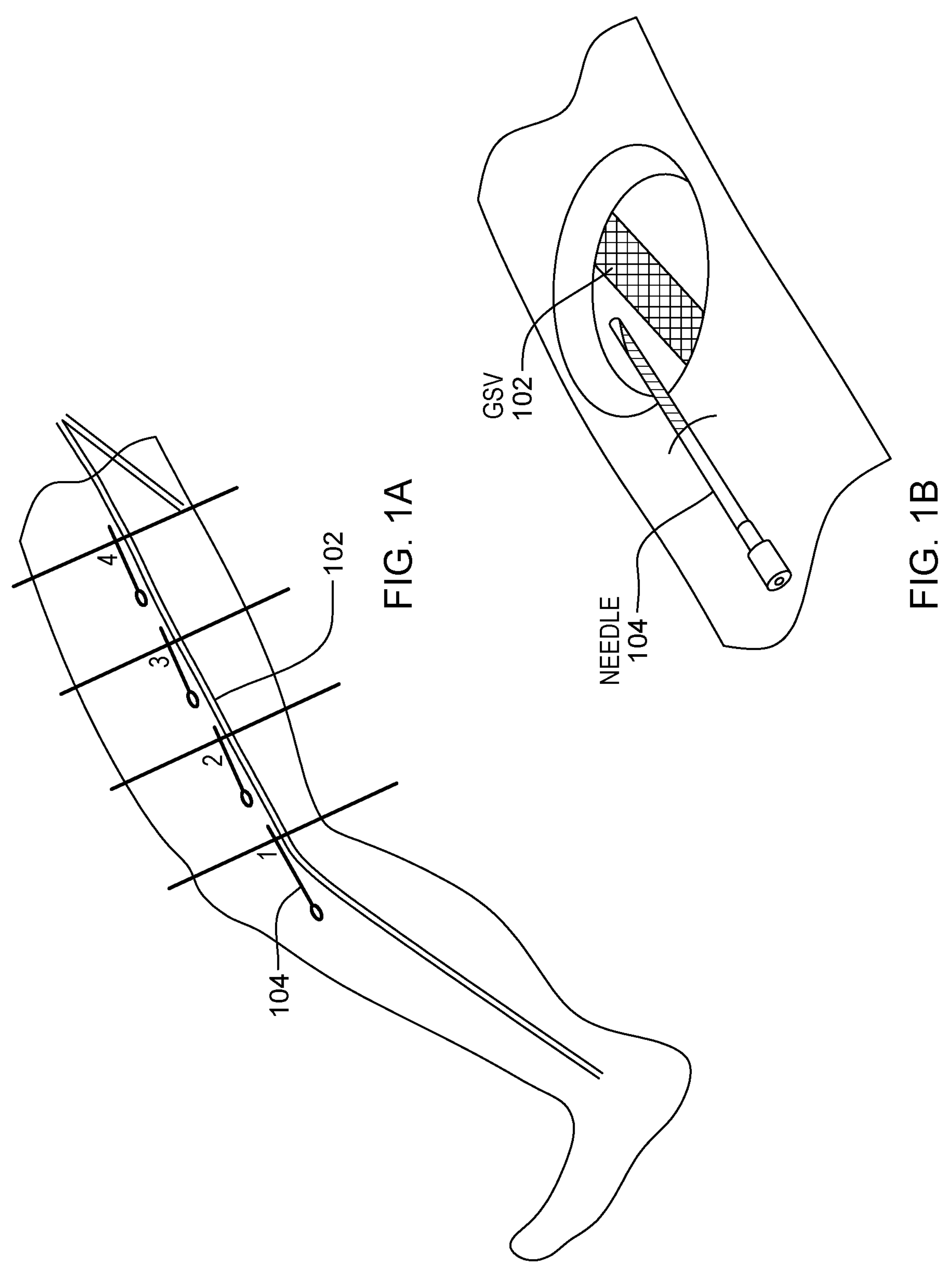
FIGS. 1A-1B show a process of hydrodissecting the GSV using one needle to hydrodissect multiple sections of the GSV.

Minimally Invasive No Touch (Mint) Procedure for CABG and Lower Extremity Bypass Since its introduction in 1967 by Renee Favalaro, coronary artery bypass surgery (CABG) has saved the lives of millions of patients with coronary artery disease (CAD). As originally described, CABG was performed by harvesting the great saphenous vein (GSV) via a longitudinal incision over the entire length of the GSV, referred to as the open vein (OVH) technique. The OVH technique, however, resulted in a significant incidence of leg wound complications, including bleeding, hematoma, infection, amputation and death. In the mid-1990's, a minimally invasive harvesting technique was developed to reduce leg wound complications called endoscopic vein harvest (EVH). EVH employs the techniques of minimally invasive surgery to harvest the GSV. Specifically, the EVH technique employs a 2 cm incision at the level of the knee. The GSV is exposed through this incision and bluntly dissected from its surrounding connective tissue, including a well-developed laminar ligament which attaches the GSV to the underlying muscular fascia. This laminar ligament has been anatomically well defined and arises from the adventitia of the GSV. While EVH has greatly reduced the incidence of leg wound complications, several recent articles have suggested that the patency rates of the GSV harvested by EVH are inferior to those harvested by the open vein technique (OVH).

Concurrent with the development of EVH, Dr. Domingos R Souza, Department of Cardiovascular and Thoracic Surgery, Örebro University Hospital, Orebro, Sweden, has developed a so called "No Touch" technique for harvesting the GSV. In this technique, the GSV is harvested with a cuff of surrounding tissue so that the GSV itself is never touched during the harvesting procedure. This technique has resulted in five year patency rates of 90% for this vascular conduit, which is equivalent to the results obtained when utilizing the internal thoracic artery (ITA), which is considered to be the gold standard of vascular conduits for CABG. Unfortunately, this technique is technically demanding and results in local leg wound complications as high as 50%. As a result, this technique has not been widely adopted.

Therefore, a need exists for a venous harvesting technique that improves patency rates of the harvested GSVs without wound complications and without requiring extensive training in adopting the technique. The minimally invasive no touch (MINT) procedure of the present invention provides these advantages by effectively improving the patency rates of harvested GSVs without the local leg wound complications associated with the known "No Touch" harvesting technique. The MINT procedure also provides for visualization of the vein during dissection and harvesting, thereby reducing or eliminating a risk of damaging the harvested GSV and making it easy for physicians to acquire the skill of harvesting the GSV.

The MINT procedure utilizes the technique of hydrodissection to facilitate the harvesting of the GSV. It should be noted that the MINT procedure, including the hydrodissection and the harvesting of the GSV, can be readily applied to harvesting the GSV for CABG and for lower extremity bypass procedures.

Hydrodissection is a technique that has been used in microsurgical procedures such as DIEP flaps, robotic prostatectomy and dissection of ITA for CABG. It has been established that hydrodissection facilitates microvascular dissection while not affecting the patency of the microvascular pedicle itself. One difficulty in using hydrodissection for harvesting the GSV is the laminar ligament which attaches the GSV to the underlying muscular fascia and which typically requires a blunt force to divide it. For example, the blunt force necessary to divide this ligament during the EVH procedure likely contributes to endothelial damage to the GSV, which can result in reduced patency rates. In order to minimize or eliminate any endothelial damage done to the GSV, the MINT procedure contemplates performing hydrodissection several hours and preferably, several days, prior to harvesting the GSV at the time of CABG. Doing so allows for recovery of any endothelial damage done at the time of the hydrodissection. However, in those patients with a need for an emergency bypass, hydrodissection can be performed immediately before harvesting and excess fluid remaining after hydrodissection can be milked or suctioned from the tunnel along the GSV before harvesting the GSV.

In greater detail, the inventive improved MINT procedure includes bringing the candidate for CABG surgery to the catheterization lab (or an associated venous treatment facility) several hours and preferably, several days prior to the actual harvesting of the GSV. The candidate is placed with the lower extremity in a frog leg position and then subjected to duplex scanning of the GSV to be hydrodissected and utilized. Ultrasonic equipment may be used for evaluating the GSV and to trace its course using a marker, e.g., Sharpie® marking pen. After confirming that the GSV is of significant caliber and quality to be utilized, the lower extremity is prepped and sterilized with Chlorhexidine prep. Hydrodissection of the GSV is then carried out under sonographic control, such as by ultrasound guidance, using a needle, such as a 20 gauge or 22 gauge echogenic spinal needle and an infusion pump, or using a venous hydrodissector with a blunt tip or a pencil tip and an opening at the end, or a venous hydrodissector as described below and shown in FIGS. 10-13 and 15-21. After the GSV is hydrodissected, the GSV is exposed using a harvester (or retractor) described in more detail herein below and is harvested by exposing and dividing side branches of the GSV and by dividing proximal and distal ends of the GSV.

During hydrodissection, needle visualization or venous hydrodissector visualization using ultrasound is used in order to insert the needle into a "sweet spot" in the extremity near the GSV without making contact with the GSV. The "sweet spot" is a predetermined position into which a tip of the needle or hydrodissector is inserted and is preferably about 1-2 mm distance away from the wall of the GSV. In other embodiments, the distance from the GSV may be smaller or greater than 1-2 mm. In certain embodiments, the "sweet spot" is located at or near the upper surface of the GSV, i.e., surface closest to the patient's skin, i.e., at a 12 o'clock location, while in other embodiments, the "sweet spot" is located to the side of the upper surface of the GSV, i.e., at about 20-90 degrees away from a plane connecting the center of the GSV and the top surface of the GSV in either direction (or between 9 o'clock and 12 o'clock or between 12 o'clock and 3 o'clock), and preferably at an angle of around 30-60 degrees from the plane connecting the center and the top surface of the GSV. Although the "sweet spot" may include other surfaces of the GSV, the top and side surfaces of the vein are the preferred locations because the GSV is held tightly to the fascia by a ligament. Since the GSV is surrounded by the fascia, needle or venous hydrodissector localization and placement of the needle or venous hydrodissector in the "sweet spot" is important so that fluid to be injected flows only into desired areas around the GSV. When multiple hydrodissection passes are performed along the length of the GSV, a second or subsequent hydrodissection pass may be performed with a second "sweet spot" being adjacent to the lower surface of the GSV, i.e., at or around a 6 o'clock location, which is opposite to the to the upper or top surface of the GSV. Alternatively, the first pass may be performed with the "sweet spot" being adjacent to the lower surface of the GSV and the second or subsequent pass may be performed with the second "sweet spot" being adjacent to the upper surface of the GSV. In certain embodiments, the second "sweet spot" may be to the side of the lower surface of the GSV (between 6 o'clock and 9 o'clock or between 6 o'clock and 3 o'clock).

Fluid used during hydrodissection is tumescent fluid, such as isotonic sodium bicarbonate with or without lidocaine, Balanced Salt Solution with a pH of around 7.4, such as Hank's Balanced Salt Solution manufactured by Thermo Fisher Scientific Isolyte Solution, or isotonic saline solution and/or any other suitable tumescent fluid solution. In some embodiments, the tumescent fluid is DuraGraft (GALA Solution named after Glutathione, Ascorbic acid, L-Arginine) endothelial damage inhibitor solution manufactured by Somahlution, Inc. based in Jupiter, Florida. DuraGraft is used for tissue preservation in the GSV specifically for CABG and is a preferred solution for performing the hydrodissection in order to reduce endothelial damage during this procedure. Examples of a GALA solution and a Hank's Balanced Salt Solution suitable for use as tumescent fluid during hydrodissection are disclosed in U.S. Pat. No. 7,981,596. In certain embodiments, tumescent fluid includes one or more medications for protecting the GSV and assisting in healing of the GSV. These one or more medications include one or more of aspirin, which protects the endothelium, heparin, such as local low-molecular weight heparin, and one or more vasodilators, such as venous vasodilators or combination dilators. Other medications that can be included in the tumescent fluid include but are not limited to one or more of the following: Nitroglycerine, Endothelin A receptor antagonist, Folic Acid, Angiotensin II receptor antagonist, Spermine/NO, Losartan, Perilyl alcohol, Superoxide dismutase, Antitissue factor antibody, Verapamil, Heparin, Ursolic acid, Local Aspirin, Rapamycin, Azathioprin, Paclitaxel, C-type natriuretic peptide, Leoligin and Papaverine. In some embodiments, tumescent fluid may include platelet rich plasma or stem cells for strengthening the wall of the GSV, and in certain embodiments, gene therapy may be used as part of the tumescent fluid.

When used for performing hydrodissection of the GSV, the use of the above-mentioned solutions should greatly reduce the initial learning curve for inexperienced Physicians Assistants, as well as improve the patency of the GSV when grafted. That is, even in experienced hands, this inventive MINT procedure should greatly eliminate the amount of blunt trauma resulting in endothelial dysfunction at the time of harvesting.

In some embodiments, the GSV is hydrodissected completely from the surrounding fascia. Complete hydrodissection may be necessary when the harvesting of the vein is performed immediately or shortly after the hydrodissection. In order to completely hydrodissect the GSV from the surrounding fascia, it may be necessary to perform multiple passes of hydrodissection along the length of the GSV, e.g., two passes of hydrodissection. For example, in a first hydrodissection pass, the needle or the hydrodissector is inserted into the "sweet spot" at or around the upper surface of the GSV (at or around 12 o'clock) and the GSV is hydrodissected by moving the needle or the hydrodissector along the upper surface of the GSV. The first hydrodissection pass will hydrodissect at least the upper half of the GSV (from 9 o'clock to 3 o'clock). In order to ensure that the GSV is completely hydrodissected around the lower half of the GSV, the second hydrodissection pass may be performed by placing the needle or hydrodissector in the second "sweet spot" at or around the lower surface of the GSV (at or around 6 o'clock), which is opposite to the "sweet spot" at the upper surface so that the needle and the dissector is between the GSV and the muscular fascia. The second hydrodissection pass proceeds by moving the needle or the hydrodissector along the lower surface of the GSV until the GSV is lifted off the muscular fascia. As discussed above, the locations of the "sweet spot" and the second "sweet spot" may be reversed or may be provided at different locations relative to the GSV.

However, in other embodiments, the GSV is partially hydrodissected so that all surrounding fascia is dissected from the vein except the laminar ligament, which can be dissected at a later time, under direct vision. In certain embodiments, the partially hydrodissected GSV remains tethered to some of the surrounding tissues. Partial hydrodissection of the GSV may result in less damage to the vein, thus extending the utility of the GSV and reducing its failure rate. Any remaining tissue can be hydrodissected under direct vision with either a spinal needle or venous hydrodissector.

As mentioned above, ultrasound guidance is used for needle or venous hydrodissector localization and during hydrodissection. After the needle or venous hydrodissector is inserted and fluid is injected, the fluid makes a pocket around the GSV and the GSV may move during the hydrodissection. Ultrasound guidance allows the user to see the pocket forming around the vein and to see the tip of the needle or venous hydrodissector to ensure that the needle or venous hydrodissector does not damage the GSV. In some embodiments of the invention, portable ultrasound equipment is used for the ultrasound guidance. For example, Terason® t3200 or t3300 Ultrasound System with Enhanced Needle Visualization (ENV) may be used for ultrasound guidance and for needle localization during the hydrodissection. The ENV helps the user to insert the needle or venous hydrodissector close to the GSV without coming into contact with the GSV.

When hydrodissection is performed using one or more needles, a needle is inserted into the lower extremity and the needle tip is visualized using ultrasound guidance. In the present illustrative embodiment, the "sweet spot" for hydrodissection using one or more needles is at the top of the GSV and about 1 mm away from the wall of the GSV. However, in other embodiments, the "sweet spot" may be off to the side of the GSV.

Once the needle tip is visualized in the "sweet spot", fluid is injected at high pressure to hydrodissect the GSV from the surrounding connective tissue. In this illustrative embodiment, a predetermined length of the GSV, e.g., about 10 cm of the GSV, is hydrodissected, after which the needle is removed, inserted at the next section of the GSV to be hydrodissected, the needle tip is visualized under ultrasound guidance, and after the needle tip is visualized in the "sweet spot," fluid is again injected at high pressure to hydrodissect another predetermined length of the GSV. This process is repeated until the entire length of the GSV is hydrodissected. In hydrodissecting each section of the GSV, the amount of fluid may be determined based on time of performing the hydrodissection, wherein the fluid is pumped at a constant volumetric flow rate (e.g., ml/m or ml/s). In the illustrative embodiment of the invention, about 100 ml of fluid is injected for about every 10 cm of the GSV being hydrodissected. In such embodiments, typically hydrodissection is performed 3 or 4 times along the length of the GSV, injecting between about 300 ml and 400 ml of fluid. Hydrodissection using one or more needles may be performed using one needle, such as an 18 gauge needle, a 20 gauge needle or a 22 gauge needle, e.g., 22 gauge echogenic spinal needle or an introducer needle with a 1/50 inch opening, or using multiple needles of similar size, wherein each needle is used for hydrodissecting a separate predetermined length of the GSV. The size of the needle is not limited to 18, 20 or 22 gauge sizes and other sizes may be used as long as sufficient fluid pressure is provided for hydrodissection. For example, the size of the needle may be between 14 gauge and 22 gauge.

Figures 2A, 2B:
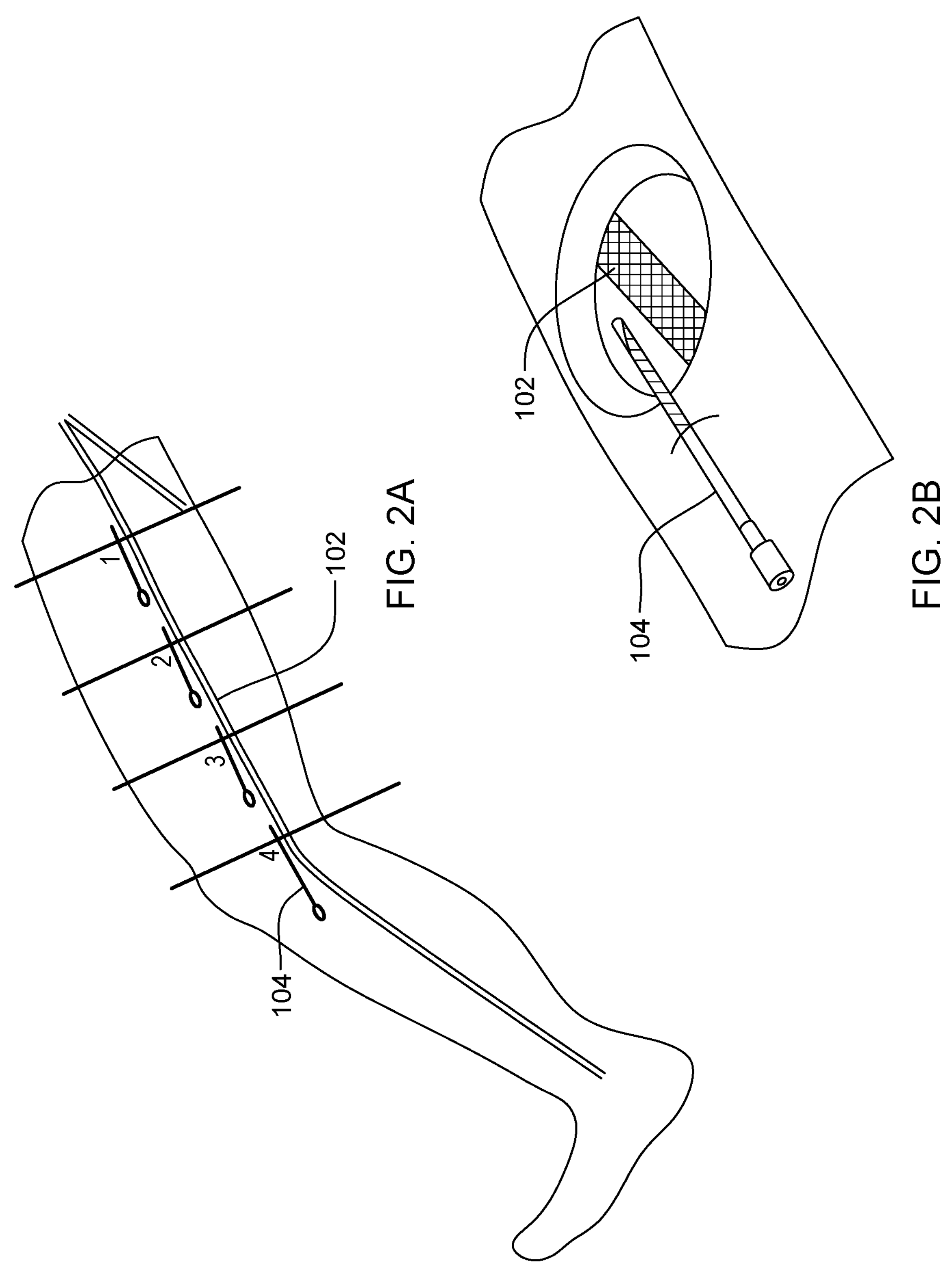
FIGS. 2A-2B show another process of hydrodissecting the GSV using one needle to hydrodissect multiple sections of the GSV.
Figures 3A, 3B:
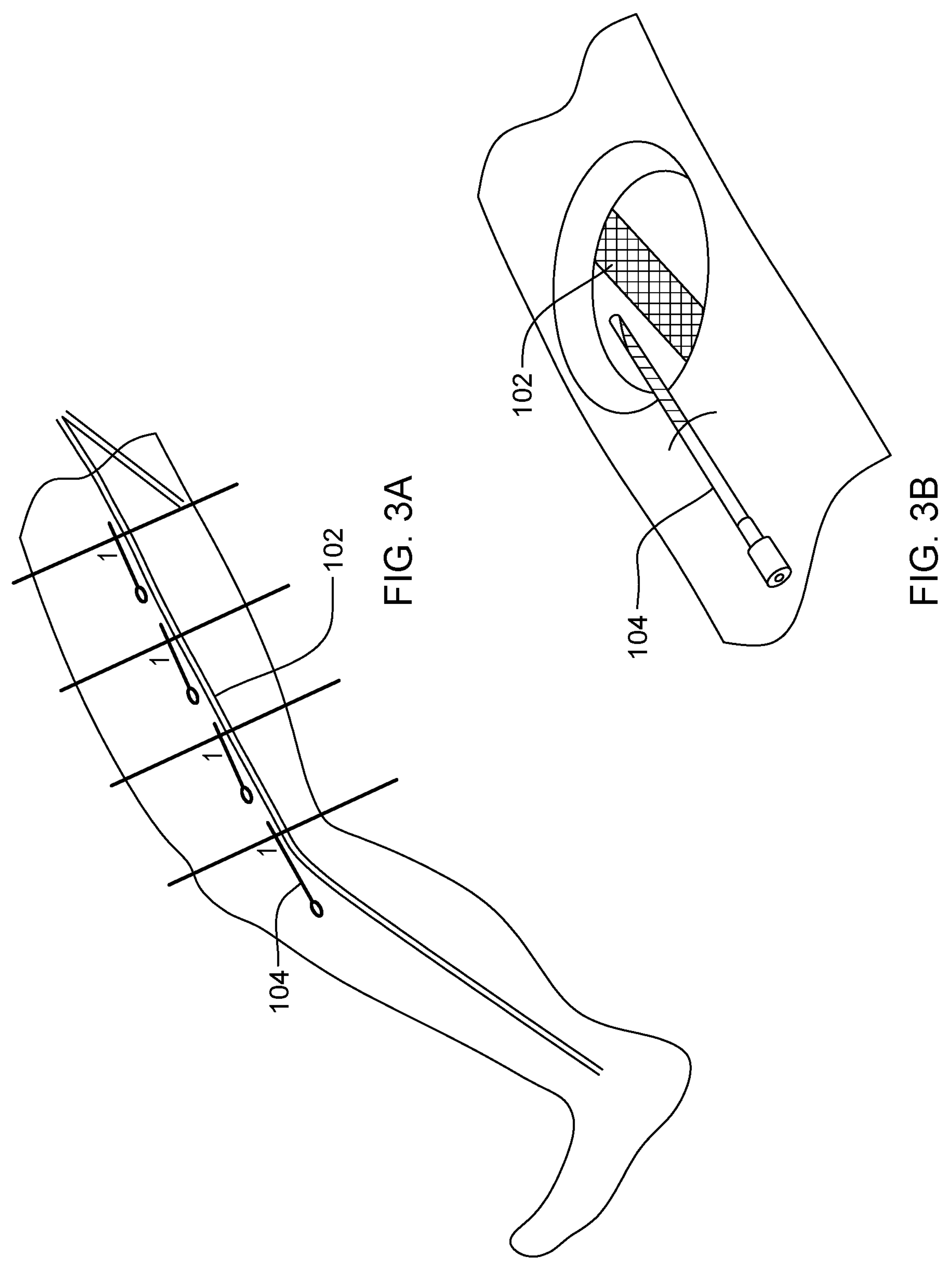
FIGS. 3A-3B show another process of hydrodissecting the GSV using multiple needles to hydrodissect respective sections of the GSV.

The process of hydrodissecting the GSV using one or more needles is illustrated in FIGS. 1A-1B, 2A-2B and 3A-3B. As shown in FIGS. 1A-1B, one needle 104 is used for hydrodissection to hydrodissect four consecutive sections of the GSV 102. In FIGS. 1A-1B, the needle 104 is inserted into each consecutive section of the GSV 102 in accordance with the circled numbers 1-4, from the knee area and up to the groin area. FIG. 1B illustrates insertion of the needle 104 into the "sweet spot" adjacent to the GSV 102 prior to injecting the fluid to dissect the GSV from surrounding connective tissue. In FIGS. 2A-2B, the order of insertion of the needle 104 into each consecutive section of the GSV 102 is opposite of FIG. 1A, starting from the groin area to the knee area. The insertion of the needle 104 into the "sweet spot" adjacent the GSV 102 in FIG. 2B is similar to that of FIG. 1B. In FIGS. 3A-3B, four needles are used for hydrodissection of four consecutive sections of the GSV 102. As shown in FIG. 3A, all four needles 104 are inserted into the "sweet spot" as shown in FIG. 3B, after which the fluid is injected through each needle to hydrodissect the corresponding section of the GSV from the surrounding connective tissue. Although FIGS. 1A-3B show hydrodissection being performed on the GSV between the knee area and the groin area, it is understood that the same hydrodissection procedure may also be performed between the knee area and the ankle of the lower extremity and may be performed along the entire length of the GSV. It is also understood that the number of sections of the GSV is not limited to 3 or 4 and may be greater depending on the length of the GSV being hydrodissected. Moreover, as described above, multiple hydrodissection passes may be made where needed in order to achieve sufficient dissection of the GSV.

Alternatively, hydrodissection may be performed by passing a narrow pencil-tip or a blunt-tipped venous hydrodissector under ultrasound guidance in the "sweet spot" through a small incision in the lower extremity and by pumping fluid, e.g., tumescent fluid, at high pressure through an opening at the tip of the venous hydrodissector to hydrodissect the GSV from surrounding connective tissues. In certain embodiments, the incision for inserting the venous hydrodissector is formed around the knee area. In this way, the hydrodissection procedure requires only one incision for hydrodissecting the entire length of the GSV, including a portion between the knee area and the groin area and a portion between the knee area and the ankle area. In some embodiments, the "sweet spot" for inserting the venous hydrodissector is about 1 mm away from the GSV wall and at a location off to the side of the GSV, such as about 20-90 degrees in either direction from a plane connecting the top surface of the GSV and the center of the GSV. This way, the venous hydrodissector is introduced along the side of the vein transversely, reducing possibility of damage to the GSV.

In some embodiments, the venous hydrodissector is introduced into the incision and after the venous hydrodissector tip is visualized in the "sweet spot," fluid is injected at high pressure through the opening in the venous hydrodissector to hydrodissect the GSV from the surrounding connective tissue. During hydrodissection, the venous hydrodissector is slid up along the GSV while injecting the fluid until the venous hydrodissector is fully inserted into the lower extremity along the GSV. After performing hydrodissection on one of the portions of the GSV, i.e., either the portion between the knee and the groin area or the portion between the knee and the ankle, the venous hydrodissector is removed and the same hydrodissection process may be performed on the other portion of the GSV through the same incision until the whole length of the GSV has been hydrodissected. In other embodiments, the venous hydrodissector may be introduced into the incision and fully inserted along the GSV to the other end of the GSV before visualizing the venous hydrodissector tip in the "sweet spot" and thereafter injecting fluid. In such embodiments, after the fluid is injected, the GSV is hydrodissected by pulling the venous hydrodissector back along the GSV. Similarly, both portions of the GSV may be hydrodissected through the same incision made in the knee area. As in the hydrodissection using one or more needles, the amount of fluid may be determined based on the amount of time of performing the hydrodissection, wherein the fluid is pumped at a constant volumetric flow rate (e.g., ml/m or ml/s). In the illustrative embodiment of the invention, about 100 ml of fluid is injected for about every 10 cm of the GSV being hydrodissected, with around 300-400 ml of fluid injected for each portion of the GSV that is hydrodissected.

Figure 4:
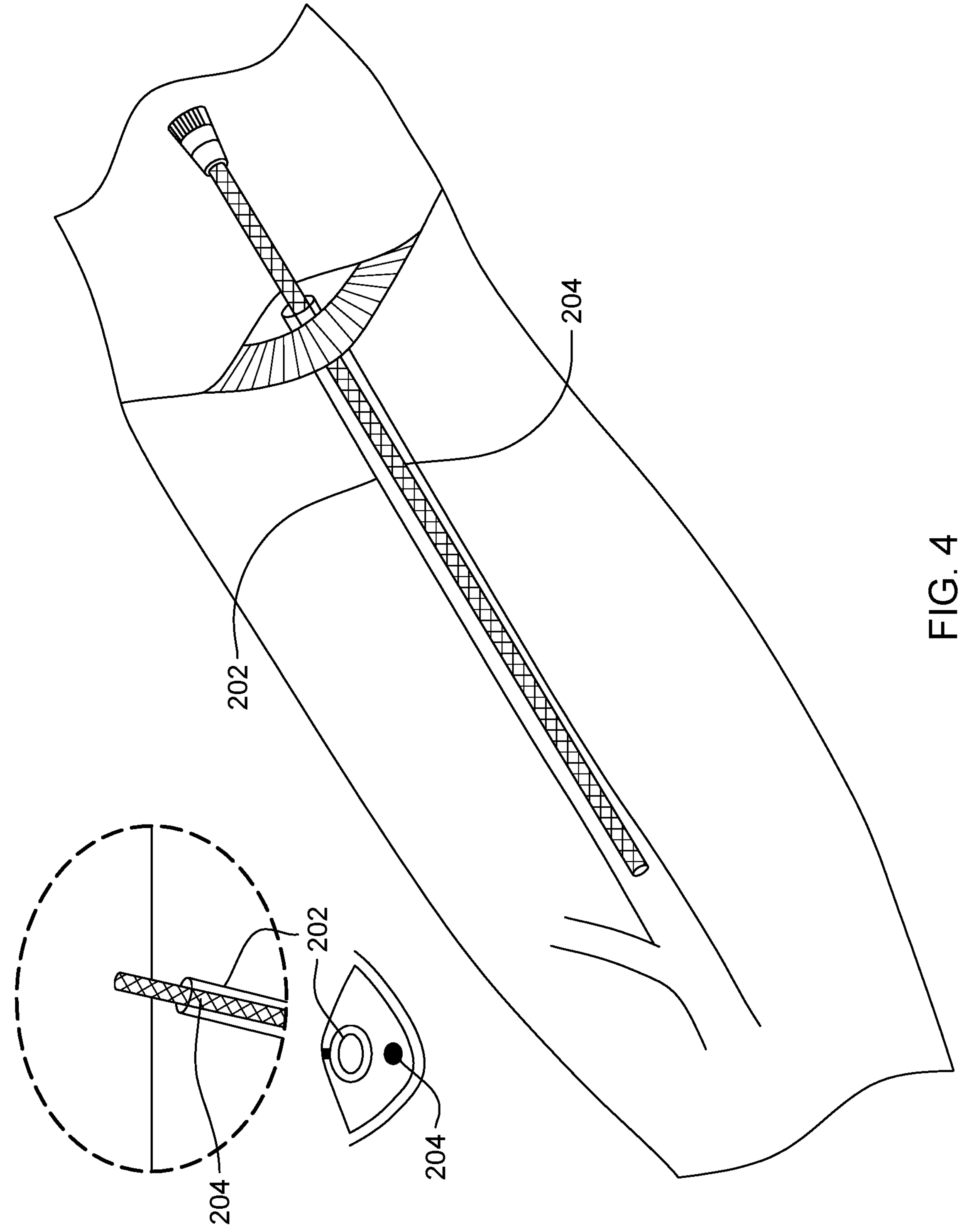
FIG. 4 shows another process of hydrodissecting the GSV using a venous hydrodissector.

The process of hydrodissecting the GSV using a venous hydrodissector is illustrated in FIG. 4. As shown, a blunt tipped venous hydrodissector 204 is used for hydrodissection to hydrodissect the one of two sections of the GSV 202. The venous hydrodissector 204 is inserted into a small incision, which is preferably formed in the knee area, and slid along the GSV 202 before placing the tip of the venous hydrodissector in the "sweet spot" and pumping tumescent fluid to hydrodissect the GSV from the surrounding tissue. In this case, the venous hydrodissector 204 is slowly pulled out through the incision while hydrodissecting the GSV. Alternatively, the venous hydrodissector 204 may be inserted into the incision and once the venous hydrodissector 204 tip is visualized in the "sweet spot", the fluid is pumped to hydrodissect the GSV while sliding the venous hydrodissector 204 further along the GSV. Although FIG. 4 shows the venous hydrodissector being inserted at the top of the GSV, in other embodiments, the venous hydrodissector is inserted along the side of the GSV, at an angle between 20 and 90 degrees from the plane connecting the center and the top of the GSV. As described above, multiple hydrodissection passes may be made where needed in order to achieve sufficient dissection of the GSV, and in a second hydrodissection pass, the hydrodissector is visualized in the second "sweet spot" which is on the opposite side of the GSV from the "sweet spot" during the first hydrodissection pass (e.g., around 180 degrees relative to the "sweet spot" during the first hydrodissection pass).

An example of a pencil tip venous hydrodissector suitable for hydrodissecting the GSV is shown in FIGS. 5A-5B. The venous hydrodissector may be disposable or may be reusable. The venous hydrodissector 204 has an elongate hollow substantially cylindrical body 206 and a pencil tip with a small opening **206*a* therein. The length of the venous hydrodissector body 206 can be between 10 and 30 cm long, and preferably between 15-25 cm long. The body of the venous hydrodissector may be made from metallic materials, such as stainless steel or titanium, or from polymers and/or plastics with sufficient strength. The venous hydrodissector 206 also includes a port 208 at the other end to which an infusion pump for pumping the fluid can be connected. The port 208 can be a standard port, e.g., a Luer Lock port, to which any standard infusion pump may be coupled, or can be any other type of port. FIG. 5B shows a close-up of the tip of the venous hydrodissector, showing a small opening 206*a* formed at the tip. The opening 206*a* should be small enough to create sufficient pressure when the fluid is pumped therethrough. For example, an opening sized between about 0.01 and 0.1 inches in diameter is suitable, and preferably between 0.01625 and 0.06 inches in diameter (14-22 gauge in size). In one illustrative embodiment, the opening 206*a* is about 0.02 inches to about 0.04 inches in diameter. In another illustrative embodiment, the opening is between 0.01625 and 0.024 inches in diameter. FIG. 5C shows a close-up view of another venous hydrodissector tip which has a cone-shaped blunt tip. Like in FIG. 5B, the venous hydrodissector tip in FIG. 5**C includes a small opening formed at the tip which is sized to create sufficient fluid pressure when fluid is pumped therethrough.

In certain embodiments, a venous hydrodissector with a wider body and a larger opening at tip may be used in combination with a needle. In such embodiments, the needle is inserted into the venous hydrodissector so that the tip of the needle is covered by the tip of the venous hydrodissector. The needle may be 14 gauge to 22 gauge in size, similar to the needle size used for the hydrodissection with a needle or a different size (gauge) needle. The infusion pump is connected to the needle and pumps the fluid through the needle and out of the tip of the venous hydrodissector. This arrangement provides for sufficient fluid pressure to hydrodissect the GSV from the surrounding tissue while protecting the GSV from inadvertent damage by using the venous hydrodissector near the wall of the GSV.

The inventive hydrodissection techniques are optimized by use of the above-described venous hydrodissector. The venous hydrodissector is configured with a pencil tip shaped or a cone-shaped tip and only one outflow port in the center of the tip to ensure that the hydrodissection implemented by use of the venous hydrodissector occurs in parallel to the GSV.

Using the above-described venous hydrodissector minimizes force vectors that might result off-angle from the axial center of the linear extent of the GSV, for example, at 90° or less which is likely in conventional or standard infusion cannulas, which are known to have one or more outflow ports arranged in the cannula shaft, which create fluid paths substantially perpendicular to the cannula longitudinal axis. Fluid typically exits from these conventional ports creating force vectors perpendicular or slightly less than perpendicular to the longitudinal axis. The venous hydrodissector, therefore, reduces trauma that the hydrodissection procedure might impose on or to the GSV.

Figure 10:
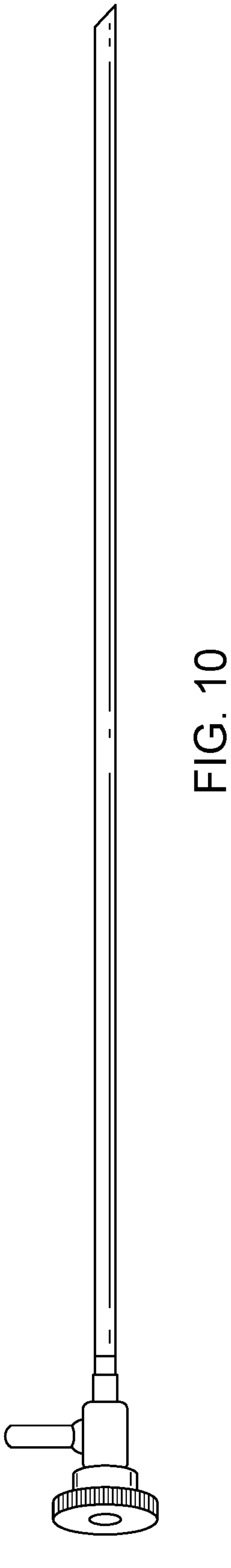
FIG. 10 shows an exemplary visualization device that uses a pediatric cystoscope.

Although the hydrodissection procedure described above is performed under ultrasound guidance, it is also possible to perform the above-described hydrodissection of the GSV under direct vision instead of using ultrasound guidance. Direct vision of the hydrodissection procedure can be achieved by using a visualization device comprising a thin tube with a camera and a light source provided at one end and capable of connecting to a display panel (e.g., a tablet, a TV, a monitor, etc.) either using a wire or wirelessly. In certain embodiments, the diameter of the tube is about 2 mm or smaller. In some embodiments, a port for infusion of liquid may be included in the visualization device, which is used as a hydrodissector, while in other embodiments, no such port is included in order to reduce the diameter of the tube. In certain embodiments, a pediatric cystoscope, an angioscope or an endoscope may be used as the visualization device. It is desired for the visualization device to be capable of capturing and transmitting clear images when exposed to liquids. An example of a suitable visualization device, which is a pediatric cystoscope, is shown in FIG. 10, or a hydrodissector shown in FIGS. 15-19. An example of a suitable angioscope is an Olympus 2 mm angioscope. In this way, the MINT procedure can be performed utilizing currently available urologic or vascular equipment.

In the embodiments that use direct vision when performing hydrodissection, the patient is first prepped and draped in the usual fashion with the donor lower extremity in the frog leg position. First, about 30 ml of tumescent fluid is injected inside the fascial envelope. In some embodiments, the tumescent fluid is injected just above the GSV, i.e., at 12 o'clock position, while in other embodiments, the tumescent fluid may be injected to the side of the GSV. This injection of the tumescent fluid can be performed either percutaneously with ultrasound guidance, such as by using a portable ultrasound device, or under direct vision via a small incision, e.g., about 2 cm incision, which exposes the GSV. If a percutaneous injection is performed, the GSV is then exposed via a small incision, e.g., standard 2-3 cm incision, just below the tumescent fluid collection.

Figure 11:
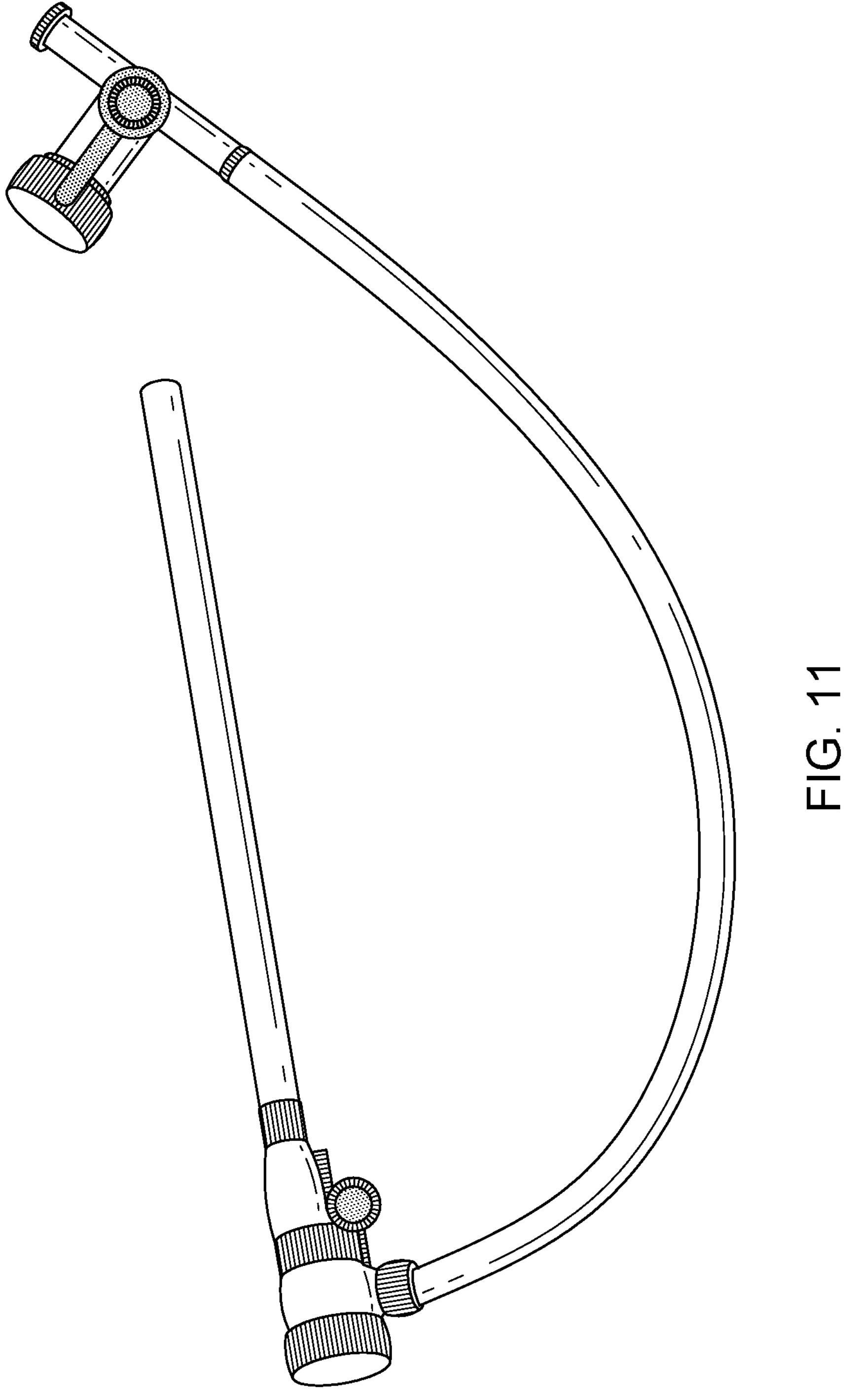
FIG. 11 shows a 7F introducer sheath suitable for use with the visualization device of FIG. 10.

Using a syringe with a needle, such as a 10 mL syringe with a 21 gauge spinal needle, the fluid collection is entered while keeping the needle and syringe parallel to and just above the exposed GSV. After the fluid is aspirated, a guide wire is passed into the fluid space and an introducer sheath, such as a 7F introducer sheath, is placed into the fluid space. FIG. 11 shows a 7F introducer sheath suitable for use in this procedure. As shown, the introducer sheath includes a side port which can be used for pumping fluid through the introducer sheath, as described in more detail below.

Figure 12:
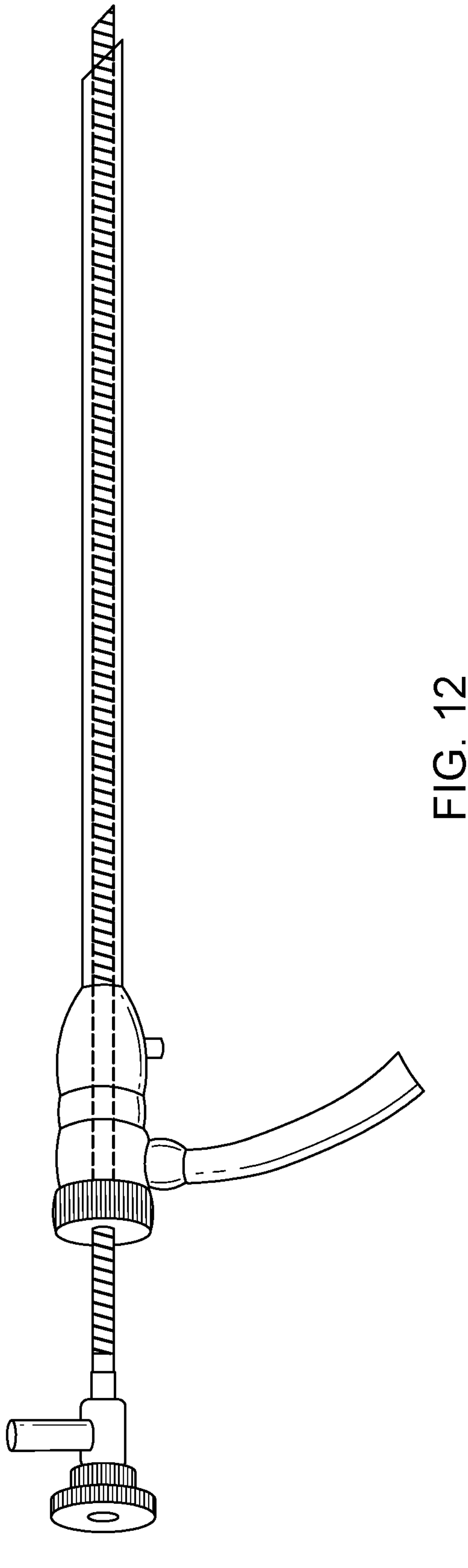
FIG. 12 shows the visualization device used with the introducer sheath.

After the introducer sheath is placed, the visualization device, such as a 2 mm pediatric cystoscope shown in FIG. 10 or a 2 mm angioscope, is passed into the fluid space via the introducer sheath. FIG. 12 shows a 2 mm cystoscope inserted into the 7F introducer sheath and demonstrates the positioning of the cystoscope relative to the 7F introducer sheath. When the visualization device, e.g., cystoscope or angioscope, is connected to a display device, either by a wire or wirelessly, the GSV is visualized directly on the monitor using the visualization device, e.g., cystoscope or angioscope. This technique allows the hydrodissection of the GSV to be performed under direct vision in real time. After the introducer sheath and the visualization device, e.g., cystoscope or angioscope, are positioned, hydrodissection can be performed using one of the following techniques.

Figure 13:
FIG. 13 shows an end portion of the visualization device extending through an end of the introducer sheath and fluid being pumped through the introducer sheath around the visualization device.

In a first technique, the side port of the introducer sheath is attached to an infusion pump and fluid is infused via the introducer sheath at a sufficiently high rate to hydrodissect the GSV. Hydrodissection is performed by moving the assembly of the visualization device with the introducer sheath, while pumping fluid along the length of the GSV or a portion of the GSV. FIG. 13 shows an end portion of the visualization device extending through an end of the introducer sheath, and fluid being pumped through the introducer sheath around the visualization device. The visualization device allows the hydrodissection to be performed under direct vision in real time and eliminates the need for ultrasound guidance.

In one example, a 7F introducer sheath like the one shown in FIG. 11 and a 2 mm cystoscope as shown in FIG. 10 or a 2 mm angioscope are used for performing hydrodissection of the GSV. The size match of the 7F introducer and the 2 mm cystoscope/angioscope diameter allows just enough room for the fluid to travel in the sheath and around the cystoscope/angioscope and to exit the sheath as a jet of fluid with sufficient pressure to hydrodissect the GSV. In addition, there is no back up or leaking of fluid. In this technique, the hydrodissection of the GSV is performed using a single assembly of the visualization device with the introducer sheath, with the assembly being advanced together as a unit along the GSV. In certain embodiments, the hydrodissection is performed by advancing the cystoscope/angioscope and introducer sheath assembly proximally toward the groin. However, in other embodiments, the direction in which the hydrodissection is performed may be changed.

In a second technique of performing hydrodissection, the hydrodissection of the GSV is performed using a needle or the venous hydrodissector, as described above, with the fluid being pumped through the needle or the venous hydrodissector and using the visualization device with the introducer sheath for direct visualization of the GSV and of the needle or the venous hydrodissector. The configuration of the needle or venous hydrodissector used in this variation of the hydrodissection procedure is the same as described above. For example, the hydrodissection may be performed percutaneously using a needle, such as a 22 gauge spinal needle, under direct vision using the visualization device with the introducer sheath. This hydrodissection technique is similar to the hydrodissection technique described above using one or more needles or using the venous hydrodissector, but instead of ultrasound guidance, this procedure is performed under direct vision.

In a third technique, a needle or a venous hydrodissector is attached to the visualization device lengthwise, so that the visualization device and the needle or the venous hydrodissector extend side by side within the introducer sheath. The configuration of the needle or venous hydrodissector used in this variation of the hydrodissection procedure is the same as described above. The needle or the venous hydrodissector is attached to an infusion pump so as to pump fluid therethrough. For example, a 20 or 22 gauge blunt tipped spinal needle can be attached lengthwise to a 2 mm cystoscope. The hydrodissection of the GSV in this technique is performed by advancing the visualization device with the attached needle or venous hydrodissector along the GSV as the fluid is being pumped, while leaving the introducer sheath in place. As in the first and second techniques, the hydrodissection of the GSV is performed under direct vision via the venous hydrodissector in real time.

Other types of hydrodissectors 1200 (or dissectors) that can be used for hydrodissection of the GSV are shown in FIGS. 15-21. The hydrodissectors of FIGS. 15-21 provide direct visualization of the GSV during hydrodissection by capturing and transmitting live images of the GSV and surrounding areas during the procedure.

Figure 15:
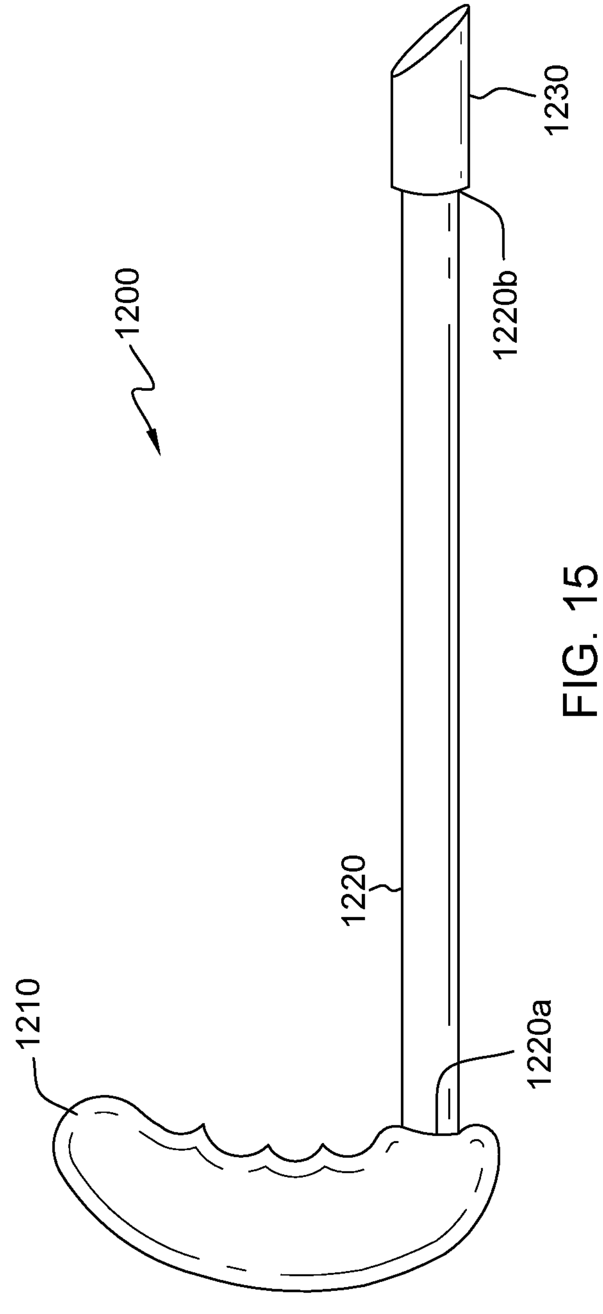
FIG. 15 shows a side view of another exemplary hydrodissector for use with the procedure shown in FIG. 4.

FIG. 15 shows a general side view of the hydrodissector 1200 with a handle 1210. As shown, the hydrodissector 1200 includes an elongate tubular-shaped body 1220 having a proximal end 1220*a* to which the handle 1210 is coupled and a distal end 1220*b* to which an angled tip 1230 is coupled. The angled tip 1230 is preferably formed from plastic, polymer material, glass, acrylic glass, e.g., poly(methylmethacrylate), Plexiglass, etc., or other suitable materials, and is transparent or translucent. The body 1220 can be formed from a metallic material, e.g., stainless steel, aluminum, titanium, etc., or from a suitable plastic or polymer material. Similarly, the handle 1210 can be formed from plastic or polymer material or may be formed from metal or any other suitable material.

The angled tip 1230 has a substantially cylindrical shape and has an angled end so that a lower surface (first surface) of the tip 1230 is longer than an upper surface (second surface) of the tip 1230. The angled end of the tip 1230 is preferably sealed or closed so as to prevent fluids and debris from entering the angled tip 1230 through the angled end. However, in other embodiments, the angled end of the tip 1230 may be partially sealed/closed or may be open. In the illustrative embodiment shown in FIGS. 15-19, the lower surface of the tip 1230 would be positioned closer to the GSV than the upper surface during the hydrodissection procedure.

To allow the lower surface of the angled tip 1230 (longer surface of the angled tip) to be positioned closer to the GSV than the opposing upper surface during the hydrodissection procedure, the orientation of the angled tip 1230 relative to the orientation of the handle 1210 may be adjustable. In certain embodiments, the handle 1210 can be rotated around the tubular-shaped body 1220 and can be locked in one or more orientations, or the tubular-shaped body 1220 can be rotated relative to the handle 1210. The locking orientations of the handle 1210 may be flexible to allow an operator to select any suitable orientation, or the locking orientations of the handle 1210 may be predetermined so as to limit the number of orientations of the handle 1210 relative to the tubular-shaped body 1220. For example, in the hydrodissector of FIG. 15, one locking orientation may be as shown in FIG. 15 where the handle is oriented in the same direction as the upper surface of the angled tip 1230, and another locking orientation may be 180 degrees around the tubular-shaped body so that the handle 1210 is oriented in the same direction as the lower surface of the angled tip 1230. Additional locking orientations may be provided in the hydrodissector. In certain embodiments, the angled tip 1230 may be rotated relative to the tubular-shaped body 1220 and may be locked in one or more orientations, which may be predetermined or may be flexible so as to be selectable by the operator. Rotating the handle 1210 and/or the angled tip 1230 around the tubular-shaped body 1220 allows the hydrodissector 1220 to be used to hydrodissect the GSV along the upper surface of the GSV, i.e., along the surface closest to the patient's skin, and to hydrodissect the GSV along the lower surface of the GSV, i.e., along the surface adjacent the muscular fascia.

Figure 16:
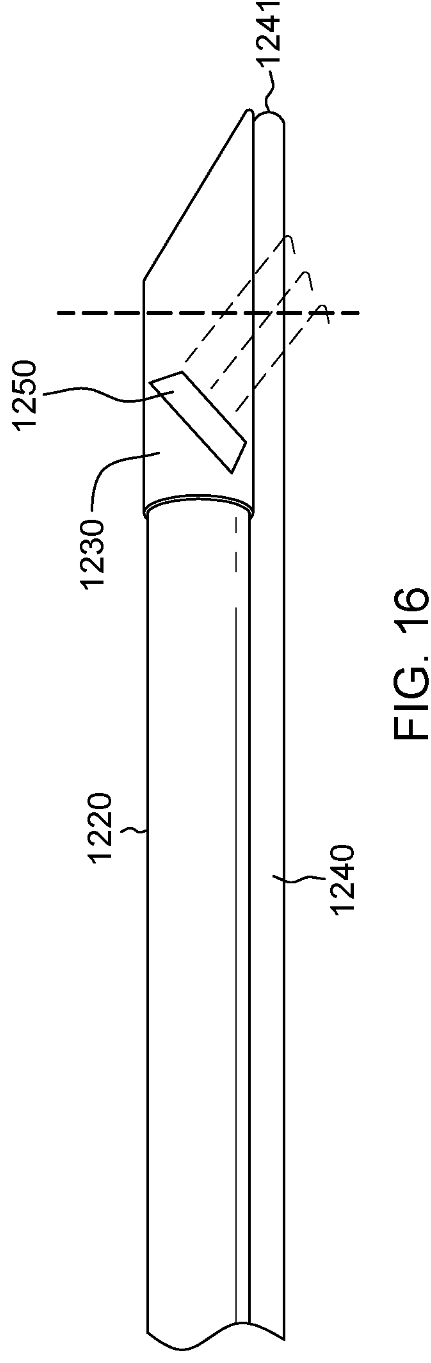
FIG. 16 shows a close-up of the side view of the hydrodissector of FIG. 15 at its distal end.
Figure 17:
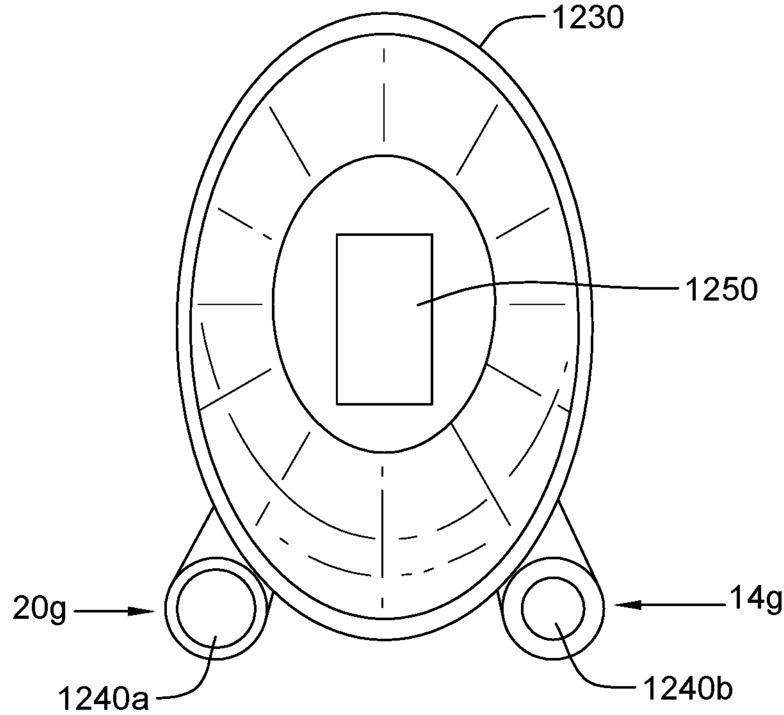
FIG. 17 shows a cross-sectional view of the hydrodissector tip, taken along a dashed line in FIG. 16.

FIG. 16 shows a close-up of the side view of the hydrodissector 1200 at its distal end and FIG. 17 shows a cross-sectional view of the hydrodissector angled tip 1230 taken along a dashed line in FIG. 16. As shown in FIGS. 16 and 17, the hydrodissector 1200 includes at least one fluid port 1240 for injecting fluid therethrough to hydrodissect the GSV as described above. The at least one fluid port 1240 includes a conduit that extends along the tubular-shaped body 1220 and is coupled to a fluid supply at a proximal end thereof (not shown) and has an injection opening 1241 at a distal end thereof. The proximal end of the conduit of the fluid port 1240 may have a Luer Lock fitting or any other suitable fitting at its end to allow the fluid port 1240 to be connected to the fluid supply, e.g., tumescent fluid supply, gas supply, e.g., CO2 supply, and/or vacuum source. The injection opening 1241 is preferably located at or near the angled end of the angled tip 1230.

In some embodiments, as shown in FIG. 17, the hydrodissector 1200 includes two fluid ports 1240*a*, 1240*b* including conduits that extend substantially parallel to one another along the tubular-shaped body 1220. The conduit of each port may have a Luer Lock fitting or any other suitable fitting at its proximal end for connection to fluid supply, gas supply and/or vacuum source. The fluid ports 1240*a*, 1240*b* may have the same size or may have different sizes from one another, and the sizes of the ports may vary between 14 and 22 gauge. In the illustrative embodiment shown in FIG. 17, the fluid port 1240*a* is smaller than the fluid port 1240*b*, with the fluid port 1240*a* having a 20 gauge size opening and the fluid port 1240*b* having a 14 gauge size opening. In this illustrative embodiment, the fluid port 1240*a* is used for injecting tumescent fluid for hydrodissecting the GSV, as described above, and the fluid port 1240*b* is used for suction of tumescent fluid after hydrodissection of the GSV. However, in other embodiments, the smaller sized port may be used for suction of fluid while the larger sized port is used for injection of fluid, or the ports may have the same size. In the embodiment of FIG. 17, the conduits of the ports 1240*a*, 1240*b* are provided along a lower outer surface of the tubular-shaped body 1220 and along the outer lower surface of the angular tip 1230. Specifically, the ports 1240*a*, 1240*b* are spaced from one another so that each port 1240*a*, 1240*b* is provided along a different side of the lower outer surface of the tubular-shaped body 1220 and along a different side of the lower surface of the angled tip 1230. In other embodiments, the ports 1240*a*, 1240*b* may be provided along the same side of the lower outer surface of the tubular-shaped body 1220 and the lower surface of the angled tip 1230. In certain embodiments, one or both of the ports may include a sealing or closing mechanism to close the port opening when not in use. In this way, when one of the ports is being used to inject fluid to hydrodissect the GSV, the fluid is prevented from escaping though the other port.

Certain embodiments may include only one port 1240, instead of two ports, for supplying fluid for hydrodissection of the GSV. In such cases, the conduit of the single port may extend along the lower outer surface of the tubular-shaped body 1220 and along the lower surface of the angled tip 1230 and may be centered or may be shifted to one of the sides relative to the tubular-shaped body and the tip. The positioning of the port depends on the position of an image capture device 1250 and is made such that the port does not block the field of view of the image capture device.

As also shown in FIGS. 16 and 17, the hydrodissector 1200 includes the image capture apparatus 1250, such as a video camera or the like, disposed inside the angled tip 1230. By placing the image capture apparatus 1250 inside the angled tip 1230, the image capture apparatus 1250 is protected from fluids and debris during the hydrodissection of the GSV. As mentioned above, in certain embodiments, the angled end of the angled tip 1230 is closed or sealed, and thus, in such embodiments, the image capture apparatus 1250 is encapsulated or encased in the angled tip and protected from fluids and debris. The image capture apparatus 1250 is configured to capture live images so as to visualize the GSV during the hydrodissection procedure. The live images may be transmitted wirelessly from the image capture apparatus 1250 to a computer, a tablet or a suitable display, or may be transmitted through a wire, e.g., by a USB connection.

The image capture apparatus is preferably a miniature camera so that it can be fitted within the angled tip 1230. The image capture apparatus may be a waterproof or non-waterproof, CMOS-based video camera with encapsulated lighting. In one example, the camera is a HD waterproof endoscope video camera probe with a small diameter of less than 1 inch, e.g., about 0.1-0.5 inch diameter, which includes a Hi-Vision or Super Hi-Vision CMOS sensor and has a resolution of 2.0 MP or higher. The camera preferably has a focal distance between 0.5 and 4 inches. However, the focal distance of the camera may vary depending on its configuration and desired position within the angled tip 1230. The camera of this example includes one or more of a USB-C connection, a Micro USB connection, a Bluetooth® connection and/or a Wi-Fi connection for connecting with an external display, computer or tablet. In other examples, the camera may be a miniature cystoscope, angioscope or laparoscope camera. In certain examples, the camera may be compatible with any operating system, such as Windows 7/8/10, Mac OS, Android system, etc. and may support a USB On-The-Go (USB OTG or OTG) and USB video device class (UVC) functions. In certain embodiments, the camera uses a lens carrier housing for enclosing the lens, and image sensor chip and/or lighting, such as the endoscope video cameras, and the lens carrier housing is attached to a surface of the angled tip of the hydrodissector or positioned within the angled tip. In other embodiments, the camera may be a one-piece assembly that incorporates the lens, the image sensor chip and/or the lighting, which can be molded into the angled tip or received in a cavity formed in the angled tip of the hydrodissector.

As shown, the image capture apparatus 1250 is positioned at an angle with respect to the lower surface of the angled tip 1230, i.e., an optical axis of the camera is at an angle with respect to the lower surface of the angled tip 1230, so that a camera lens and a camera sensor are provided at an angle with respect to the line of sight to the GSV which underlies the lower surface of the angled tip during hydrodissection. The angle of the image capture apparatus 1250 may be between 15 and 60 degrees relative to the lower surface of the angled tip 1230. In the illustrative embodiment of FIG. 16, the image capture apparatus 1250 is positioned at about a 30 degree angle relative to the lower surface of the angled tip 1230. This angled positioning of the image capture apparatus 1250 allows for direct viewing of the GSV to be hydrodissected and during the hydrodissection procedure. The angle of the image capture apparatus 1250 relative to the lower surface of the angled tip 1230 will depend on the distance of the image capture device 1250 from the injection opening 1241 of the fluid input port 1240*a* and the field of view of the image capture apparatus 1250. Although not shown in FIGS. 16 and 17, the angled tip 1230 may also have one or more light sources, e.g., one or more LEDs, disposed therein. For example, a plurality of LEDs may be disposed around the image capture apparatus 1250, or at least one LED may be disposed adjacent to the image capture apparatus 1250. In some embodiments, the LEDs are angled relative to the lower surface of the angled tip 1230 similarly to the image capture apparatus 1250 so as to direct light emitted from the LEDs in the same direction as the object being captured by the image capture apparatus 1250. Also not shown in FIGS. 15-17 are one or more power sources for powering the image capture apparatus 1250 and/or the light source(s) and any connections or wiring necessary for connecting the power source(s) to the image capture apparatus 1250 and/or the light source(s) and for connecting the image capture apparatus 1250 with a display, a computer or tablet, if needed. In some embodiments, the image capture apparatus 1250 may include an internal power source, while in other embodiments, the power source may be disposed within the tubular-shaped body 1220 or within the handle 1210. The connections or wiring to the power source and/or to the display, computer or tablet may be provided through the tubular-shaped body 1220 and/or through the handle 1210.

Figure 18:
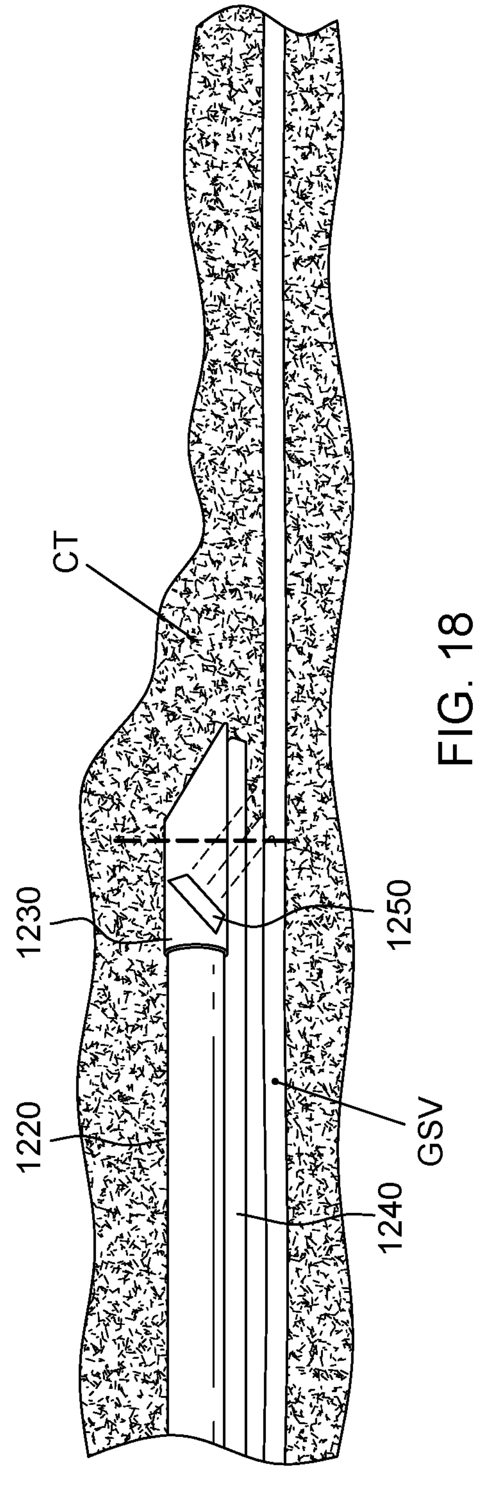
FIG. 18 shows an end view of the hydrodissector of FIG. 15 in situ, surrounded by connective tissue above the GSV.
Figure 19:
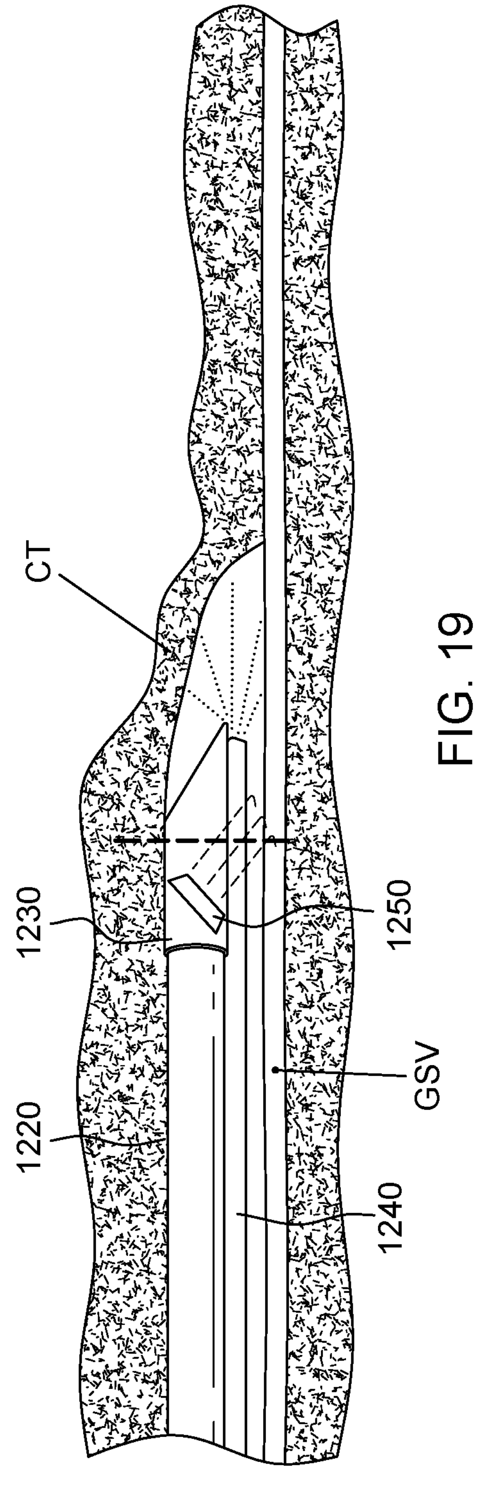
FIG. 19 shows an end view of the hydrodissector of FIG. 15 in situ while dissecting connective tissue off the underlying GSV.

FIGS. 18 and 19 show the hydrodissector of FIGS. 15-17 being used during hydrodissection of the GSV along the top surface of the GSV. As shown in FIG. 18, the hydrodissector is surrounded by the connective tissue just above the GSV. As discussed above, to hydrodissect the GSV, the hydrodissector is placed in the "sweet spot", with the angled tip 1230 being preferably just above the top surface of the GSV, e.g., a few millimeters above the GSV, and the image capture apparatus 1250 is used for directly visualizing the hydrodissector 1200 in the "sweet spot" and for directly visualizing the GSV and the surrounding area. After the hydrodissector of FIGS. 15-17 is placed in the "sweet spot," fluid is injected through one of the fluid ports 1240*a* or 1240*b* as shown in FIG. 19 so as to dissect the connective tissue off the GSV. The hydrodissector 1200 is moved along the length of the GSV while dissecting the connective tissue off the GSV in order to hydrodissect the entire length of the GSV.

As mentioned above, the GSV may be hydrodissected using multiple hydrodissection passes, so that during the second hydrodissection pass, the hydrodissector 1200 is visualized adjacent the lower surface of the GSV, which is opposite to the upper surface of the GSV shown in FIGS. 18 and 19, and then fluid is injected through one of the fluid ports of the hydrodissector, while moving the hydrodissector along the lower surface of the GSV to dissect the muscular fascia from the GSV. Before using the hydrodissector 1200 for the second hydrodissection pass, the handle 1210 or the angled tip 1230 of the hydrodissector is rotated about 180 degrees relative to the tubular body so that during the second hydrodissection pass, the lower (longer) surface of the angular tip 1230 faces the GSV.

Figures 20A, 20B, 20C:
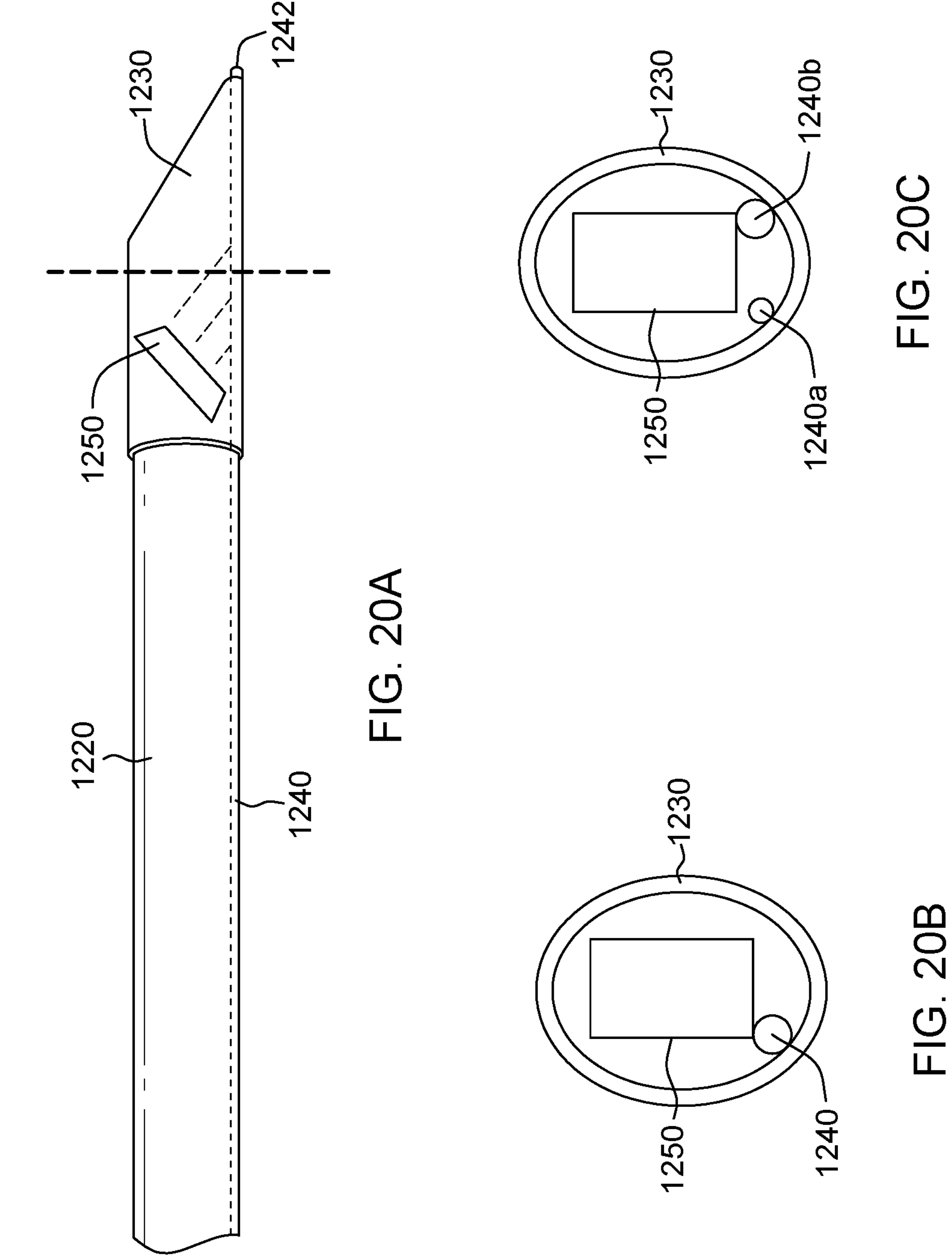
FIGS. 20A-20C show another exemplary version of the hydrodissector for use with the procedure shown in FIG. 4.
Figures 21A, 21B, 21C:
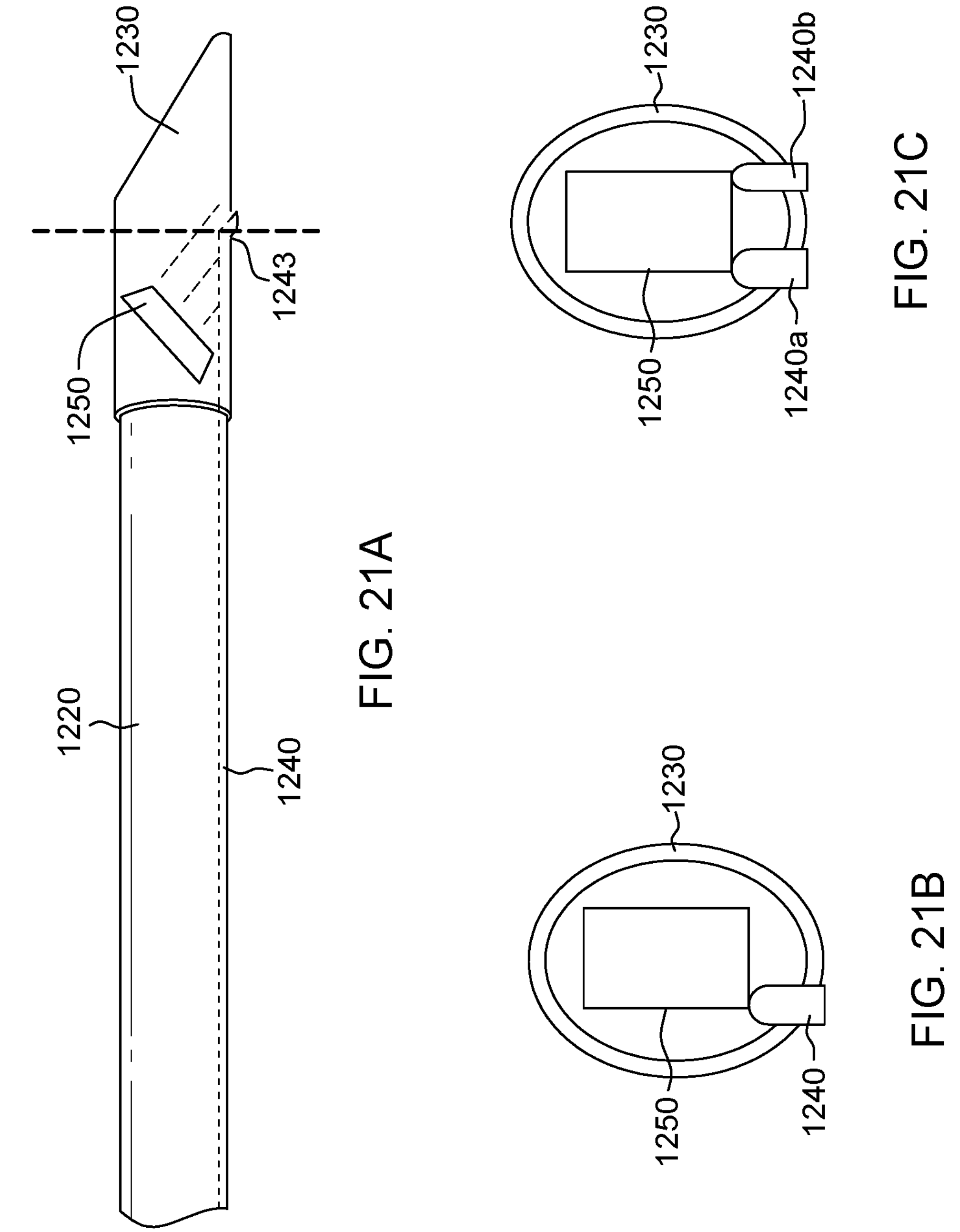
FIGS. 21A-21C show another exemplary version of the hydrodissector for use with the procedure shown in FIG. 4.

FIGS. 20A-20C and 21A-21C show other versions of the hydrodissector 1200 that can be used for hydrodissecting the GSV. The hydrodissector 1200 in FIGS. 20A-20C and 21A-21C is modified by providing the one or more ports 1240 that include conduits inside the tubular-shaped body 1220. FIGS. 20A and 21A show a close-up side view of the hydrodissector 1200 near its distal end, and in each of these embodiments, the hydrodissector 1200 includes the tubular-shaped body 1220, the angled tip 1230 attached to the distal end of the tubular-shaped body 1220, the image capture apparatus 1250 provided inside and enclosed by the angled tip 1230 and one or more ports 1240 for fluid supply, gas supply and/or vacuum. As in the embodiment of FIGS. 15-19, the image capture apparatus 1250 is provided at an angle between 15 and 60 degrees relative to the lower surface of the angled tip 1230. The conduits of the one or more ports 1240 are provided within the tubular-shaped body 1220 and the difference between the embodiment of FIG. 20A-C and FIG. 21A-C is the configuration of the one or more ports 1240.

As shown in FIG. 20A, the conduits of the one or more ports 1240 extend along the lower inner surface of the body 1220 and along the inner lower surface of the angled tip 1230. An opening 1242 is provided for each port at the end of the angled tip 1230. FIGS. 20B and 20C show cross-sectional views of the hydrodissector 1200 in FIG. 20A taken along the dashed line in FIG. 20A. FIG. 20B shows a cross-sectional view of a hydrodissector with one port 1240, and FIG. 20C shows a cross-sectional view of a hydrodissector with two ports 1240*a* and 1240*b*. The ports 1240, 1240*a*, 1240*b* preferably have an opening of 14-22 gauge in size. In FIG. 20B, the port 1240 is preferably a fluid port for supplying tumescent fluid for hydrodissection of the GSV and has a size between 14 and 22 gauge, and preferably, 20 or 22 gauge. In FIG. 20C, the ports 1240*a*, 1240*b* may have the same size or may have different sizes. For example, port 1240*a* may be used as a fluid port for supplying tumescent fluid for hydrodissection of the GSV and may have a size between 14 and 22 gauge, and preferably, 20 or 22 gauge. The port 1240*b* may be used as a suction port and may have a larger size between 14 and 22 gauge, and preferably between 14 and 18 gauge. In certain embodiments, the port 1240*a* may be used for suction and the port 1240*b* may be used for fluid supply and may be sized as needed for these functions. In certain embodiments, one or both of the ports 1240*a*, 1240*b* may be closed or sealed when not in use in order to prevent fluid from entering the unused port during the hydrodissection procedure.

As shown in FIGS. 20B and 20C, the port 1240 or the ports 1240*a*, 1240*b* are disposed on the inner lower surface of the angled tip 1230 and are shifted to the side away from the center. In FIG. 20C, both ports may be provided on the same side instead of being on different sides of the angled tip 1230. In any case, the ports 1240, 1240*a*, 1240*b* are positioned so as not to block the field of view of the image capture apparatus 1250 through the lower surface of the angled tip 1230.

In FIGS. 21A-21C, the hydrodissector 1200 has one or more ports 1240 including conduits which extend along the lower inner surface of the tubular-shaped body 1220 and along a portion of the angled tip 1230. Each port 1240 is then directed through an opening 1243 in the lower surface of the angled tip 1230 to outside of the hydrodissector 1200. The end of the port 1240 may extend downwardly from the opening or may be angled toward the distal end of the hydrodissector, as shown in FIG. 21A. Although FIG. 21A shows the port 1240 extending through the opening 1243 in the lower surface of the angled tip 1230, in other embodiments, the opening may be provided in the lower surface of the tubular body 1220 and the port 1240 would extend through the opening in the tubular body 1220. The position of the opening would depend on the desired position of fluid injection from the hydrodissector 1200 during the hydrodissection procedure.

FIGS. 21B and 21C show cross-sectional views of the hydrodissector 1200 in FIG. 21A taken along the dashed line in FIG. 21A. FIG. 21B shows a configuration of the hydrodissector 1200 with one port 1240, while FIG. 21C shows a configuration of the hydrodissector 1200 with two ports 1240*a*, 1240*b*. As in FIGS. 20B and C, the ports 1240, 1240*a*, 1240*b* are shifted to the side away from the center so as not to block the view of the image capture apparatus 1250 through the angled tip 1230. In FIGS. 21B and 21C, port sizes and uses are similar to those of FIGS. 20B and 20C and thus, detailed description thereof is omitted.

Although the embodiments of FIGS. 20A-21C show at least one port 1240 extending along the lower surface of the body 1220 and the angled tip 1230, in other embodiments, fluid may be supplied directly to the tubular-shaped body 1220, without using a separate structure for the port, and a small opening may be provided in the angular tip for fluid injection therefrom. The opening size should be such that fluid is injected from the opening with sufficient fluid pressure for hydrodissection of the GSV. The opening size may be between 14 and 22 gauge and preferably, 20 or 22 gauge. The opening may be provided at the end of the angled tip, similar to FIG. 20A or may be provided in the lower surface of the angled tip, similar to FIG. 21A.

Although FIGS. 15-17 and 20A-21C show the hydrodissector that uses the angled tip 1230, in other embodiments, the angled tip 1230 may be removable from the body 1220 and may be interchangeable with other types of tips attachable to the body 1220. Different tips may be used for different phases of the procedure, e.g., angled tip 1230 for hydrodissection of the GSV and other types of tips for harvesting of the GSV. In certain embodiments, the angled tip 1230 may be removable from the body 1220 and may be replaced with a shovel-shaped or spoon-shaped tip. An example of a shovel-shaped or spoon-shaped tip is shown in FIGS. 7, 8A and 8B, which show the shovel-shaped or spoon-shaped tip being used on a harvesting retractor. In such cases, the camera and/or any light sources are held in the shovel-shaped or spoon-shaped tip, e.g., on the concave surface of the shovel-shaped or spoon-shaped tip, which provides partial protection for the camera and/or light source(s) from fluids and debris. The camera and/or light source(s) may be positioned so as to face in a direction away from the handle and toward a distal end of the dissector (e.g., at about 90 degrees relative to the lower surface of the tip) or may be angled to face away from the concave surface of the shovel-shaped or spoon-shaped tip (e.g., at an angle between 90 and 180 degrees relative to the lower surface of the tip). In such embodiments, the camera may use a lens carrier housing that encloses the lens, the image sensor chip and/or lighting (e.g., LEDs) and the lens carrier is attached, either permanently or detachably, to the concave surface of the spoon-shaped tip. In yet other embodiments, the camera may be a one-piece assembly that incorporates the lens, the image sensor chip and/or the lighting, which can be molded into the spoon-shaped tip or received in a cavity formed in the spoon-shaped tip.

As in the embodiment of FIGS. 15-17, the port(s) in this embodiment are provided along the lower surface of the shovel-shaped or spoon-shaped tip (along the convex surface thereof) and any wiring or connections and power source(s) are provided within the body 1220 and/or the handle 1210. Alternatively, the fluid port(s) may be provided along the inside surface of the body 1220, similar to the embodiments of FIGS. 20A and 21A, and may be passed to the outside through an opening in the body 1220.

In certain embodiments, instead of interchangeable tips which can be removed from the body 1220 and changed as needed, the body 1220 of the hydrodissector is releasable and removable from the handle and can be replaced with a different body having a different tip. For example, the body 1220, i.e., shaft, of the hydrodissector of FIGS. 15-17 that includes the angled tip, may be removable from the handle and interchangeable with a second body, i.e., shaft, with a different tip, such as a shovel-shaped or spoon-shaped tip, to be attached to the handle. This configuration of the hydrodissector, where the body together with the tip, is interchangeable, avoids removal and changing of small parts on the hydrodissector during or in between surgical procedures.

The dissector with the shovel-shaped or spoon-shaped tip thereon, or with the second body having the shovel-shaped or spoon-shaped tip, may be used as a retractor or harvester during the harvesting of the GSV, as described in more detail below. Similar to the retractor shown in FIGS. 6 and 7, and described below, one or more C-shaped and/or U-shaped attachments may be releasably attached to the shovel-shaped or spoon-shaped tip or to the body 1220 of the dissector. In addition, as in the retractor of FIGS. 6 and 7, the tip and/or the body 1220 may have multiple coupling positions for selectively coupling or clipping on the C-shaped and/or U-shaped attachments at different locations.

Figure 22:
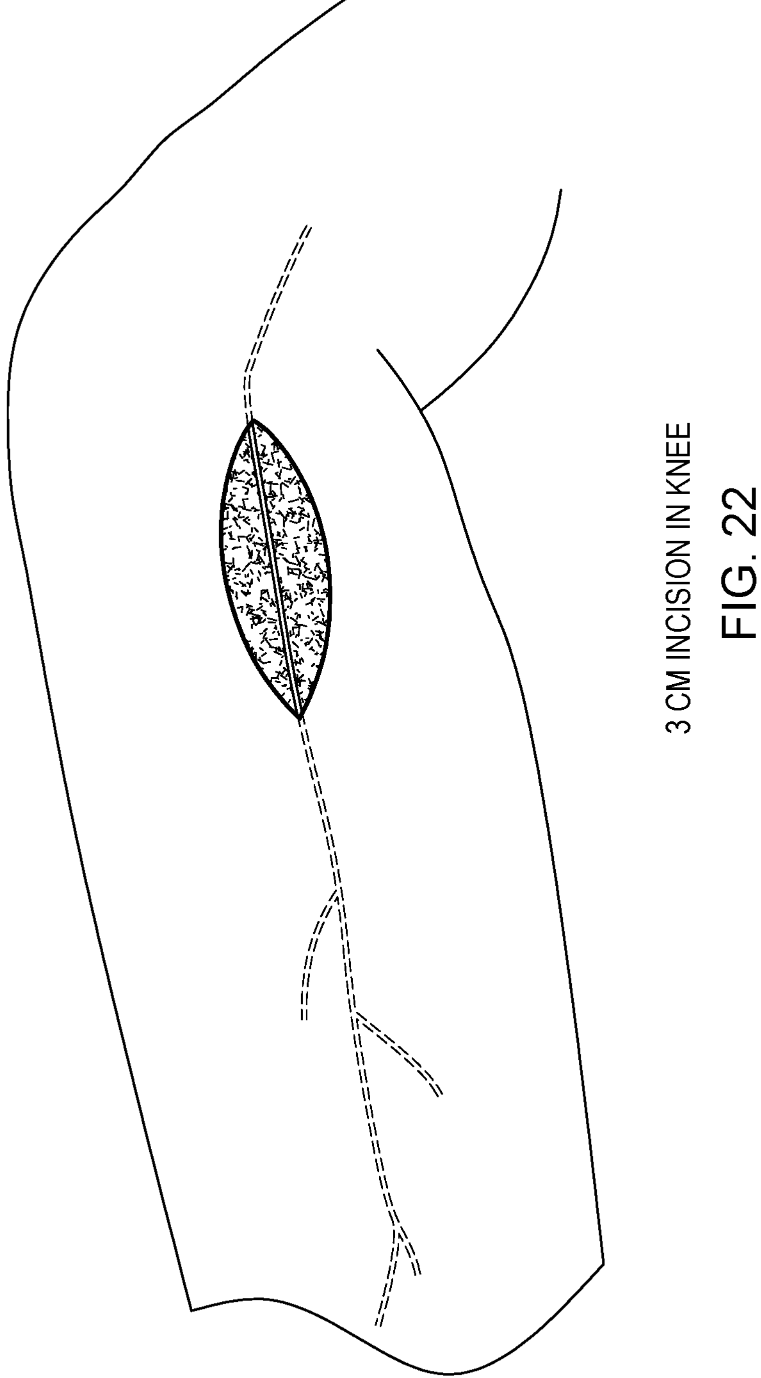
FIGS. 22-25 show another version of the procedure for hydrodissecting the GSV.
Figure 23:
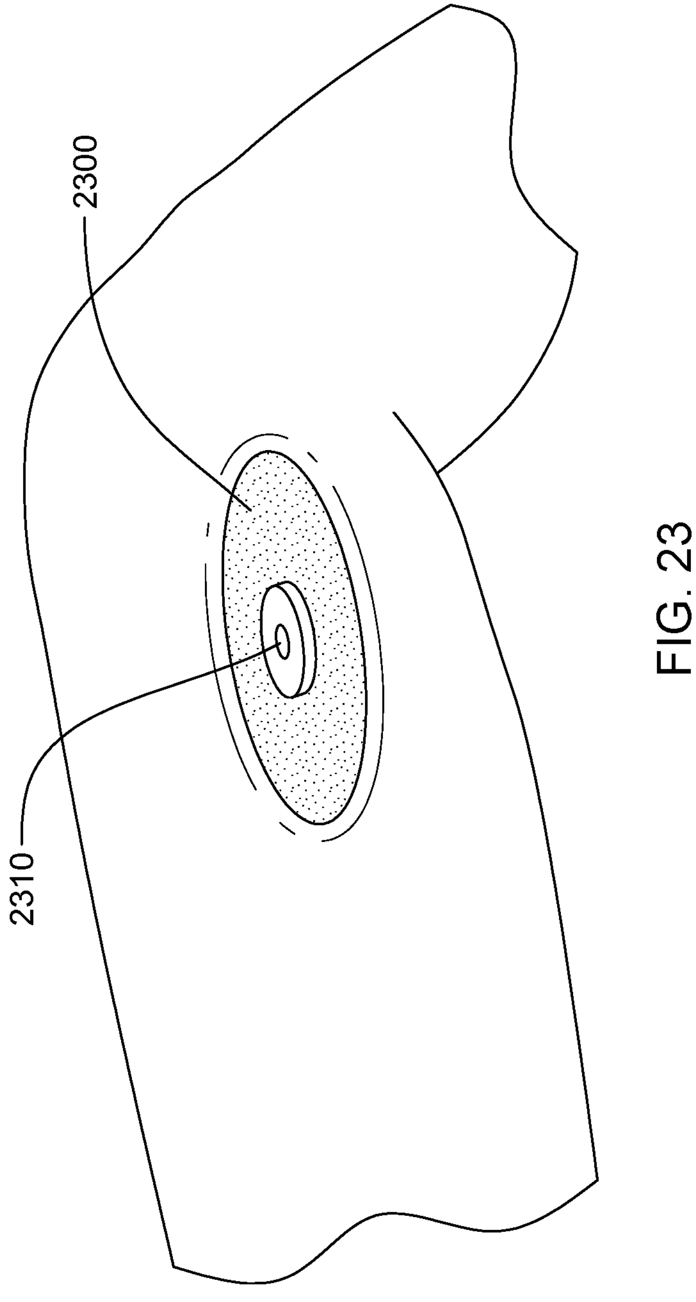
Figure 24:
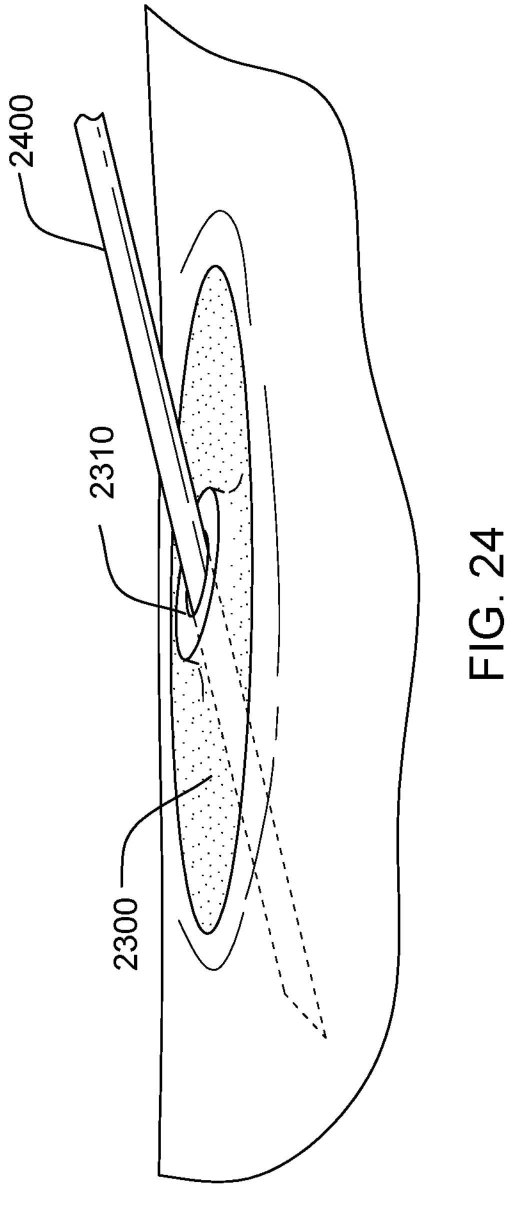

When the venous hydrodissector of FIGS. 5A-5C, the visualization device of FIGS. 10-13 or the hydrodissectors of FIGS. 15-19, 20A-C and 21A-C are used for hydrodissecting the GSV, the above-described hydrodissection procedure may be modified as shown in FIGS. 22-26 in order to provide a fluid-tight insertion access site to the GSV through an incision. The modified hydrodissection procedure of FIGS. 22-26 may also be used when the tumescent fluid is injected using one or more needles. As shown in FIG. 22, a 3 cm or similar size incision is made at the knee of the patient, and as shown in FIG. 23, a small circular or elliptical diaphragm 2300 or a suitable tissue occluder with a one-way valve 2310 or access port is placed through the incision to cover and seal the incision made in FIG. 22. The diaphragm may be made of rubber or similar fluid-tight and malleable material. The one-way valve 2310 is water-tight so as to prevent leakage of tumescent fluid injected into the incision during hydrodissection. As shown in FIG. 24, the hydrodissector 2400, such as the visualization device of FIGS. 10-13 or the hydrodissector of FIG. 5A-5C, 15-19, 20A-C or 21A-C, is placed through the access port 2310 and thereafter directed to the "sweet spot" adjacent the top surface of the GSV. The hydrodissection procedure is then performed as described above by injecting tumescent fluid to hydrodissect the GSV from the surrounding fascia and moving the hydrodissector along the top surface of the GSV to accomplish hydrodissection of the entire length of the GSV.

Figure 25:
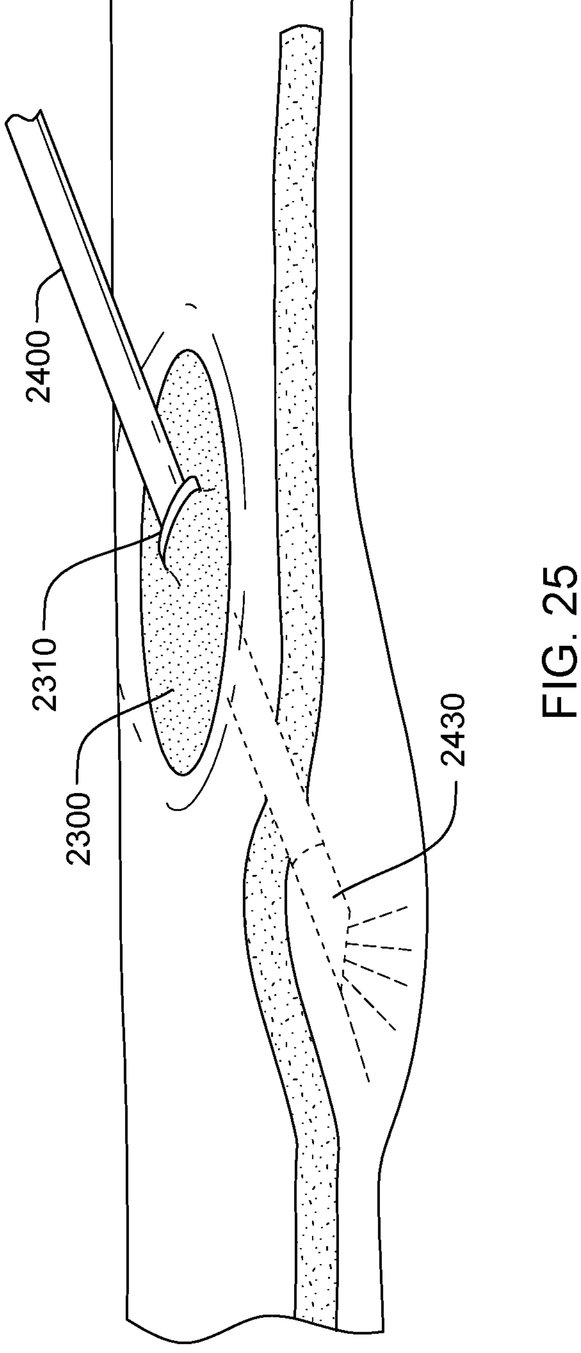

As discussed above, in certain embodiments, multiple hydrodissection passes may be needed to achieve sufficient hydrodissection of the GSV from the surrounding fascia. In certain cases, when hydrodissection of the GSV is performed as shown in FIGS. 22-24, at least the upper half of the GSV from about 9 o'clock to about 3 o'clock is hydrodissected from the surrounding fascia. In order to ensure that the lower half of the GSV is completely hydrodissected from 3 o'clock to 9 o'clock, the second hydrodissection pass may be performed along the lower surface of the GSV. Prior to performing the second hydrodissection pass, the handle 1210 or the angled tip 1230 of the hydrodissector shown in FIGS. 15-21C is rotated about 180 degrees and locked in this orientation so that when the hydrodissector is used for the second hydrodissection pass, the image capture apparatus in the angled tip 1230 faces the GSV to provide direct visualization of the GSV. As shown in FIG. 25, the hydrodissector 2400 is placed through the access port 2310 in the diaphragm and directed to the second "sweet spot" adjacent the lower surface of the GSV (at or around the 6 o'clock position). In this position, the angled tip 2430 of the hydrodissector 2400 is positioned between the GSV and the muscular fascia to which the GSV is attached. The second hydrodissection pass then proceeds in a controlled fashion by injecting tumescent fluid from the hydrodissector and with the image capture apparatus facing the GSV, i.e., looking up at the GSV at 6 o'clock, as the GSV is being lifted off the muscular fascia. The second hydrodissection pass ensures complete hydrodissection of the GSV from the surrounding fascia and eliminates the need for use of a needle to touch up the hydrodissection.

In certain embodiments, in addition to the direct visualization provided by the hydrodissector using a camera, ultrasound guidance may be used in order to place the tip of the hydrodissector in the "sweet spot" and to advance the hydrodissector along the GSV. In such cases, an ultrasound probe used for ultrasound guidance is connected to the same or different display unit, computer or tablet as the camera of the hydrodissector. When the ultrasound probe and the camera of the hydrodissector are connected to the same display unit, computer or tablet, a split screen is displayed showing live images from the camera and ultrasound images from the ultrasound probe. In this way, the operator can control the dissection of the GSV by keeping the hydrodissector right over the GSV and also watching the fluid form a halo around the GSV using the ultrasound probe. As mentioned above, portable Terason® ultrasound devices may be used for ultrasound guidance during hydrodissection. FIG. 26 shows an exemplary split screen visualization which includes an ultrasound view of hydrodissection on a left screen portion and direct visualization on a right screen portion. After the hydrodissection of the GSV is complete, the hydrodissector is removed and the fluid is evacuated. Alternatively, prior to removing the hydrodissector, fluid supply is turned off and suction is turned on via a suction port of the hydrodissector in order to evacuate the fluid. In this case, the hydrodissector is removed after evacuating the fluid.

The above described hydrodissection of the GSV procedures allow the GSV to be dissected from the surrounding fascia without damaging the GSV. Moreover, the saphenous nerve runs along the GSV and is often damaged by conventional techniques, resulting in loss of a sensory function. Hydrodissection of the GSV completely dissects the saphenous nerve from the GSV, without damaging the nerve, and as a result, sensory function of the extremity is not affected. In experienced hands, the GSV hydrodissection procedure takes less than 10 minutes to perform. In this technique, a catheter in the GSV is not required to render the GSV echogenic and thus easy to visualize during hydrodissection. Therefore, the above-described hydrodissection is performed without a catheter present in the GSV.

As discussed above, the hydrodissection procedure also requires that a sufficient amount of tumescent fluid is injected around the GSV so that the vein is surrounded by a dark halo of fluid (when viewed using u/s or under direct vision) without any echogenic connective tissue. This ensures that at the time of GSV harvest for CABG, the only attachments of the GSV will be its branches which have also been hydrodissected from the surrounding connective tissue. This is possible because in a closed space such as the fascial envelope surrounding the GSV, the force vector of the fluid creating the hydrodissection travels along the path of least resistance which is the interface between the adventitia of the GSV and its branches and the surrounding connective tissue.

Moreover, by hydrodissecting the GSV, the hydrodissected GSV may be used as a drug-delivery system by applying one or more medications or solutions to the adventitia or the outer wall of the GSV. The one or more medications or solutions may be applied to the GSV during hydrodissection by including one or more medications in the tumescent fluid, as described above, or by separately applying the one or more medications to the hydrodissected GSV after performing the hydrodissection. As discussed above, in some embodiments, medications to protect the GSV and to heal the GSV may be applied to the hydrodissected GSV, and in particular, to the adventitia of the hydrodissected GSV, including aspirin, which protects the endothelium, heparin, such as local low-molecular weight heparin, and one or more vasodilators, such as venous vasodilators or combination dilators. Other medications may include but are not limited to one or more of the following: Nitroglycerine, Endothelin A receptor antagonist, Folic Acid, Angiotensin II receptor antagonist, Spermine/NO, Losartan, Perilyl alcohol, Superoxide dismutase, Antitissue factor antibody, Verapamil, Heparin, Ursolic acid, Local Aspirin, Rapamycin, Azathioprin, Paclitaxel, C-type natriuretic peptide, Leoligin and Papaverine. Characteristics and use of these medications is described in more detail in "*Perivascular administration of drugs and genes as a means of reducing vein graft failure*" by Wiedemann, et al., published by Current Opinion in Pharmacology 2012, 12:203-216. In some embodiments, platelet rich plasma or stem cells may be used to strengthen the wall of the GSV. In certain embodiments, gene therapy may be used on the GSV.

As discussed above, ideally, hydrodissection of the GSV is performed several hours or one or two days prior to the harvesting of the GSV and the actual bypass surgery. For harvesting of the GSV and the bypass surgery, the patient is prepped and draped in a standard fashion, and the hydrodissected GSV is exposed through an incision in the knee area. A retractor (also referred to as a "harvester") described below can be used to expose the GSV so as to allow for visualization of the GSV in order to allow harvesting of the GSV. Alternatively, as discussed above, the hydrodissector described above with respect to FIGS. 15-17 and with the shovel-shaped or spoon-shaped tip may be used for harvesting the GSV. During the harvesting procedure, the retractor or harvester is used to expose the GSV and to lift the GSV so that exposed side branches of the GSV can be divided. Specifically, the side branches of the GSV are divided with a bipolar cautery device or using hemoclips or scissors. Thereafter, proximal and distal ends of the GSV are also divided so as to allow the harvested GSV to be used for bypass surgery.

Figure 6:
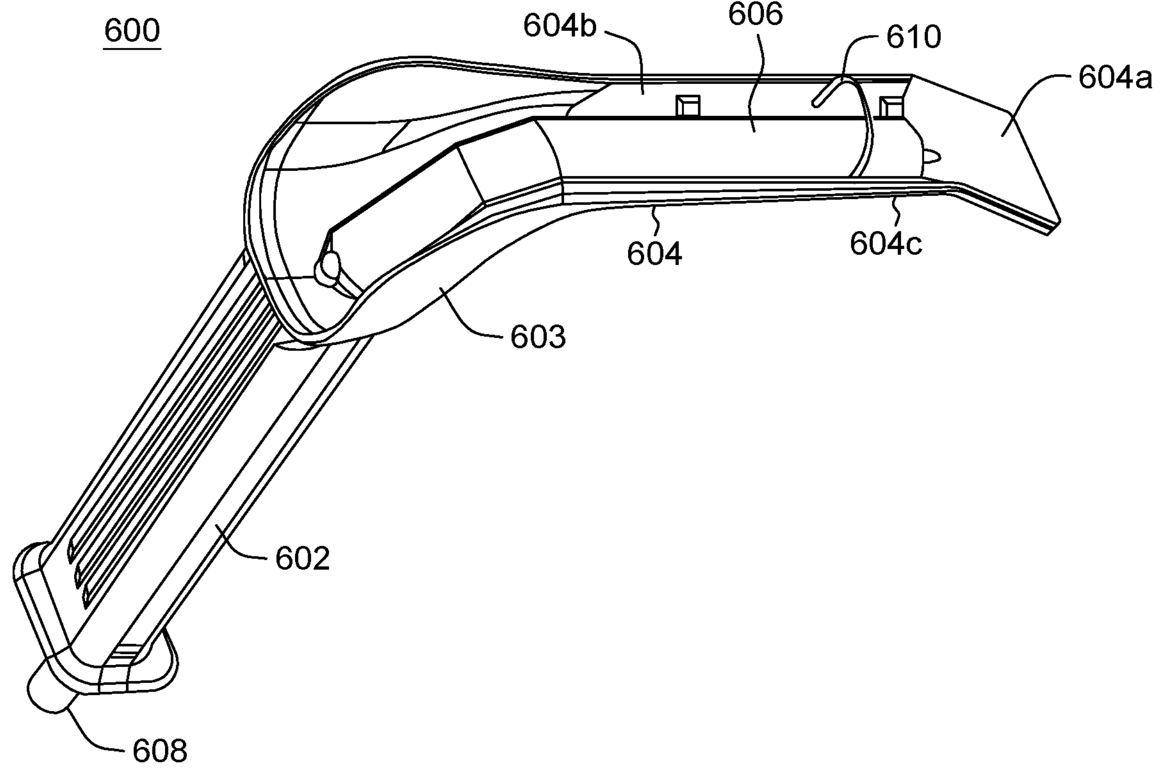
FIG. 6 shows a retractor for use during harvesting the GSV.

FIGS. 6, 7, 8A and 8B illustrate a retractor or harvester which may be used during the GSV harvesting procedure. The retractor is preferably a disposable retractor. However, in some embodiments, the retractor may be reusable. FIG. 6 shows one embodiment of the retractor or harvester, while FIGS. 7 and 8A-8B show another variation of the retractor of FIG. 6, which has a different blade and tip configuration. Both retractors of FIG. 6 and of FIGS. 7 and 8A-8B may be used for harvesting as shown in FIG. 7.

As shown in FIG. 6, the retractor 600 includes a handle 602 and a blade 604 extending at an angle from the handle 602. The retractor 600 may include a curved section 603 connecting the handle 602 to the blade 604.

The blade 604 of the retractor 600 is of sufficient length to be inserted along the dissected GSV so as to expose the GSV and its branches. For example, the length of the blade 604 may be between 10 and 30 cm. In one example, the length of the blade is around 25 cm, while in another example, the blade is 15 cm in length. The width of the blade can be between 1 and 5 cm, and preferably between 2 and 4 cm. In one example, the width of the blade 604 is 2 cm, while in another example, the width of the blade is 4 cm. As shown in FIG. 6, the blade 604 also includes a tip 604*a*, which in FIG. 6 is shown as a substantially rectangular tip angled relative to the rest of the blade 604. The configuration of the tip 604*a* of the blade 604 may be varied and is not limited to the one shown in FIG. 6. For example, the tip 604*a* may have a rounded shape or may have a triangular shape with the sidewalls converging to a narrower tip or to a point. In another example, the tip may be shovel-shaped or spoon-shaped, as shown in FIGS. 7 and 8A-8B. In some examples, the tip 604*a* may include a lip at its end, or projections or an in-molded pattern to assist in holding back the tissue. In other variations, the end of the tip 604*a* may be smooth. In yet other examples, the tip 604*a* may be aligned with the rest of the blade 604 instead of being angled.

The blade 604 has a first surface 604*b* which faces an inside of the patient when in use and a second surface 604*c* which faces the outside of the patient when in use. The retractor 600 also includes a channel formed along the first surface 604*b* of the blade 604 and extending through the handle 602 of the retractor to a port 608. The channel includes a channel cover 606 that covers at least a portion of the channel extending along the first surface 604*b* of the blade 604 and which is coupled with the handle and/or may extend into the handle. The configuration of the channel and the channel cover 606 may be similar to the smoke evacuation channel used in a retractor described in U.S. Pub. Nos. US 2016/0354072 and 2017/0245849 and U.S. application Ser. No. 15/869,994, all of which are assigned to the same assignee herein and are incorporated herein by reference. In the retractor of the present invention, the channel can be used for removal of fluid, debris and/or smoke as well as for providing fluid into the incision and the open cavity. For example, the channel may be used for washing the GSV with fluid, such as the sodium bicarbonate solution or a solution of one or more medications mentioned above, and/or for providing a $CO_2$ infusion to the GSV.

In certain embodiments, particularly those that use the channel for conducting liquids and for supplying liquids to the patient cavity, the construction of the channel is made airtight and/or watertight so as to prevent the fluids from leaking into and possibly damaging other components of the retractor, e.g., electrical components. For example, in order to ensure watertight construction, the channel may include a tube, a conduit or a similar fluid conveying member extending from the port 608 in the handle and through the length of the handle 602. The tube may also extend under the cover 606 along at least a portion of the length of the blade 604. In other embodiments, the cover may engage with the blade 604 in an airtight manner and extend into the handle to fluidly couple with the tube or similar device passing through the handle to the port 608. As can be appreciated, the port 608 can be connected to a fluid supply and/or an infusion pump for supplying the fluid, e.g., $CO_2$, sodium bicarbonate solution, medication solution, etc. Additionally, the port 608 can be connected to a vacuum source when suction from the cavity is needed.

As shown in FIG. 6, the retractor also includes one or more U-shaped attachments 610 which are releasably attached to the blade 604 so as to protrude from the first surface 604*b* of the blade. In the illustrative embodiment of FIG. 6, a single U-shaped attachment is provided near the distal end of the blade 604. However, it is understood that the position of the U-shaped attachment may be varied and may be changed from one position to another depending on the needs of the user. In some embodiments, multiple U-shaped attachments may be used if desired.

Multiple coupling mechanisms may be provided along the length of the blade 604 so as to allow desired positioning of the U-shaped attachment(s) along the length of the blade. As shown in FIG. 7, the U-shaped attachment is used to gently lift and hold the hydrodissected GSV. This allows for holding and exposing the perivenous space with one hand. As can be seen in FIG. 7, the tip 604*a* of the blade 604 is inserted into the incision to expose the hydrodissected GSV. After inserting the tip of the blade 604 into the incision and exposing the GSV, the U-shaped attachment can be snapped or clipped onto the blade and around the GSV so as to allow the retractor to gently raise the GSV to separate it from the surrounding tissues. When the GSV is exposed and held by the retractor 600 of the present invention, the branches are easily visible to the user and can be divided using bipolar cautery, hemoclips or scissors.

In the present invention, it is desired for the U-shaped attachment(s) to be completely releasable from the retractor blade. This configuration avoids having any branches of the GSV being torn or damaged. The U-shaped attachment may be clipped onto the blade 604 such as by inserting the ends of the U-shaped attachment into corresponding slots in the blade and engaging the ends of the U-shaped attachment with the corresponding slots. In some embodiments, the ends of the U-shaped attachment may include outward protrusions, which are inserted into corresponding slots in the blade while squeezing the legs of the U-shaped attachment toward each other and which engage with the corresponding slots in the blade by releasing the legs of the U-shaped attachment. The slots in the blade may have a horizontal, vertical or angled orientation relative to the length of the blade. Other mechanisms of releasable coupling of the U-shaped attachment, such as use of cantilever joints and other types of snap-fit mechanisms, are contemplated by the invention. In other embodiments, the U-shaped attachment may have only one leg permanently fixed to the retractor and the other leg releasably attached so as to allow opening and closing of the U-shaped attachment.

In yet other embodiments, one or more C-shaped attachments may be used instead of the U-shaped attachment(s), wherein one of the ends of the C-shaped attachment is attached to or engaged with the first surface of the blade, while the other end is not attached to the blade and is positioned at a distance from the first surface of the blade. This configuration allows the GSV to be slipped into the C-shaped attachment through the space between the unattached end and the first surface of the blade. The C-shaped attachment(s) may be releasable from the retractor blade, or in some embodiments, the C-shaped attachment(s) may be permanently attached to the retractor blade.

Although FIG. 6 shows the U-shaped attachment being coupled to the first surface of the blade, in other embodiments, the span of the U-shaped attachment or C-shaped attachment may be smaller and the coupling of one or both legs of the attachment may be to the channel cover 606. In yet other embodiments, one or more coupling mechanisms for the attachment may be provided at or near the tip 604*a* of the blade. It is also understood that the particular shape of the attachment is not limited to the U or C shape and that other shapes may be suitable for lifting the GSV.

In accordance with the present invention, the retractor 600 of FIG. 6 may be a "smart" retractor which is provided with an illumination assembly for illuminating the operating field and/or with an image capturing assembly for capturing still and/or video images of the operating field in order to allow for observation of the GSV during the harvesting procedure. In some embodiments, the illumination assembly is provided separately from the image capturing assembly. In other embodiments, the illumination assembly is integrated into the image capturing assembly, wherein the image capturing assembly includes one or more light sources for illuminating the operating field and for illuminating an area to be captured in one or more still or video images.

FIGS. 8A and 8B show schematic exemplary embodiments of the "smart" retractor when viewed from the tip 604*a* of the retractor blade 604 of FIG. 7. The "smart" retractor of FIGS. 8A and 8B includes an illumination assembly with at least one light source 812 and/or an image capturing assembly with a camera 814. The light source 812 may be an LED or any other suitable light source, and in some embodiments, the light source may be used in combination with an optical guide (a waveguide) for conducting light from the light source. In some embodiments, the camera 814 is an endoscope camera which is miniature in size so that it can be attached to the retractor blade 604 without interfering with the tissues and the GSV. The camera 814 may be a waterproof, CMOS-based video camera with encapsulated lighting. In one example, the camera 814 is a HD waterproof endoscope video camera probe with a small diameter of less than 1 inch, e.g., about 0.1-0.5 inch diameter, which includes a Hi-Vision or Super Hi-Vision CMOS sensor and has a resolution of 2.0 MP or higher. The camera preferably has a focal distance between 0.5 and 4 inches, and in this example has a focal distance between 1.2 and 2.4 inches. However, the focal distance of the camera may vary depending on its configuration and desired position on the retractor blade. The camera may include adjustable light sources, e.g., LEDs, at the camera tip. The camera in this example may have 6-8 LEDs disposed at the tip of the camera and spaced around the periphery of the tip. The number of LEDs may be varied depending on the size of the camera and the size and brightness of the LEDs. The brightness and/or color of the LEDs may be adjustable. The camera 814 of this example includes one or more of a USB-C connection, a Micro USB connection, a Bluetooth® connection and/or a Wi-Fi connection for connecting with an external display. In certain examples, the camera may be compatible with any operating system, such as Windows 7/8/10, Mac OS, Android system, etc. and may support a USB On-The-Go (USB OTG or OTG) and USB video device class (UVC) functions. More specific examples of the camera 814 include endoscope cameras manufactured by Depstech® including NTC85S 2-In-1 Endoscope, WiFi10 WIFI Endoscope or WIFI Borescope. Other waterproof miniature cameras are suitable for use in the retractor of the present invention.

Although not shown, in certain embodiments, the illumination assembly further includes at least one energy source, e.g., a battery, an activation device, e.g., a removable tab, a switch, a button or the like, and electrical connections among the activation device, the energy source and the light source(s). The construction of the illumination assembly may be similar to the illumination assemblies disclosed in U.S. Pub. Nos. US 2016/0354072 and 2017/0245849 and U.S. application Ser. No. 15/869,994, which are incorporated herein by reference.

The image capturing assembly includes an image capture apparatus, i.e., a camera 814, which is capable of taking still and/or video images. The image capturing assembly may also include a storage device, e.g., a memory card, flash storage, or the like, for storing captured images/videos and/or a communication interface for communicating captured images/videos and/or live view images/videos to one or more outside devices. The communication interface may be a wired communication interface, such as USB or HDMI, or a wireless communication interface, such as Bluetooth®, Wi-Fi or Near Field Communication. In certain embodiments, the camera may be capable of both wired and wireless communication, including but not limited to USB, HDMI, Bluetooth®, Wi-Fi, Near Field Communication, etc. For example, the image capture assembly may be connected, by a wire or wirelessly, to a video screen, so as to transmit images during the procedure and to allow the user to view the images on the video screen. The image capture apparatus, the storage device and/or the communication interface are preferably housed within the same housing. In certain embodiments, the image capturing assembly also includes one or more energy sources, e.g., batteries, or may be electrically coupled with the one or more energy sources of the illumination assembly. In yet other embodiments, the image capturing assembly may not include any energy sources therein and may require external power supply, e.g., via a USB connection. For example, during use, the image capturing assembly may be connected via the USB connection with a display screen so that power is supplied to the image capturing assembly from the display screen via the USB connection and captured or live images are transmitted from the image capturing assembly to the display screen via the same USB connection.

In certain embodiments, the camera uses a lens carrier housing for enclosing the lens, and image sensor chip and/or lighting, such as the endoscope video camera described above, and the lens carrier housing is permanently or releasably attached to the surface of the retractor or to the tip of the retractor. In other embodiments, the camera may be a one-piece assembly that incorporates the lens, the image sensor chip and/or the lighting, which can be molded into the retractor blade or into the tip of the retractor blade or may be received in a cavity formed in the retractor blade or the tip of the blade.

In the embodiments of FIGS. 7, 8A and 8B, the retractor is modified from the retractor of FIG. 6, wherein the blade includes a channel passing therethrough, the channel cover 606 is formed on the concave surface of the tip 604*a* and is coupled with the channel passing through the blade 604. In other embodiments, the blade may include a channel along the surface of the blade with a channel cover provided on the surface of the blade 604, similar to the configuration of FIG. 6, and the channel cover 606 formed on the surface of the tip 604*a* may be coupled with the channel and the corresponding channel cover provided on the blade 604. In the embodiment of FIG. 8A, the light source 812 (or a waveguide when used in combination with the light source) of the illumination assembly is positioned at or near the open end of the channel cover 606 and is configured to illuminate the operating area around the tip 604*a* of the retractor blade. In FIG. 8A, the camera 814 is provided outside of the channel cover 606 and is attached to the concave surface of the retractor tip 604*a*, the surface of the retractor blade and/or to the external surface of the channel cover 606. In some cases, the camera 814 is releasably attached to or clipped or snapped onto the retractor blade, the retractor tip or the channel cover. In other embodiments, the camera is permanently attached to the retractor. Although FIG. 8A shows the camera 814 being provided outside the channel cover 606 while the light source 812 is provided inside, or partially enclosed by, the channel cover 606, in other embodiments, the positions of the camera 814 and the light source 812 may be switched so that the camera 814 is provided inside or partially enclosed by the channel cover 606 and the light source 812 is provided outside the channel cover 606.

In the embodiment of FIG. 8A, wiring connecting the light source 812 to the at least one energy source (not shown) can be provided between the channel cover 606 and the concave surface of the tip 604*a* and extend along or inside the blade and into the handle of the retractor. Exemplary positioning of the wiring between the light source and the energy source is described in U.S. Pub. Nos. US 2016/0354072 and 2017/0245849. Wiring, if any, for connecting the camera 814 to an energy source (external or within the handle of the retractor) and/or to any external device (e.g., display screen) may be provided along the surface of the retractor blade 604 outside of the channel in the retractor blade or may be provided in the channel in the retractor blade and may extend from the proximal end of the blade or through the retractor handle.

In the embodiment of FIG. 8B, the light source 812 of the illumination assembly and the camera 814 of the image capturing assembly are positioned adjacently at or near the open end of the channel cover 606. In this case, wiring connecting the light source 812 and the camera 814 are provided between the channel cover 606 and the concave surface of the tip 604*a*, along the channel in the blade 604 or along the outer surface of the blade and may extend into and through the handle of the retractor and/or from the proximal end of the blade.

In certain embodiments of FIGS. 8A and 8B, the positioning of the light source 812 and/or the camera 814 may be varied relative to the end of the channel cover 606. For example, either the light source 812 or the camera 814, or both, may be positioned closer to a distal end of the tip 604*a* of the retractor blade. For example, in some embodiments, the camera 814 may be positioned at the end of the tip of the retractor blade, and in other embodiments, the camera may be positioned about 1-2 cm away from the end of the blade tip. In yet other embodiments, the camera 814 may be positioned further away from the blade tip. The positioning of the camera 814 relative to the tip of the retractor blade is dependent on the depth of field, the color of the illumination and the amount of light provided by the illumination assembly. The camera 814 should be positioned so as to allow clear visualization of the GSV being harvested while avoiding debris and fluids from the operating region blocking the view of the camera 814. In certain embodiments, the position of the camera 814 relative to the tip of the blade may be changeable, such as by sliding by a sliding mechanism along the blade or by detaching the camera 814 from one position and reattaching the camera 814 at another position relative to the tip. In some embodiments, the camera may be a self-cleaning camera that is capable of clearing any debris or fluids accumulating on the camera lens. In certain embodiments, the camera may be waterproof or liquid proof and/or may be coated with a waterproof coating, such as a silicone coating.

As mentioned above, in some embodiments, the illumination assembly may be integrated with the image capturing assembly. For example, one or more light sources may be provided as part of the image capturing assembly on the camera 814 or may surround the camera 814 or the camera lens so as to provide a single integrated assembly. In such embodiments, power for the integrated image capturing and illumination assembly may be provided from an external source, e.g., via a USB cable. Alternatively, the retractor may include one or more energy sources provided in the handle or near the proximal end of the blade for powering the one or more light sources and/or the camera. In some embodiments, the integrated image capturing and illumination assembly may selectively use power supplied by one or more energy sources in the retractor, e.g., in the handle or on the blade, for the light sources and/or the camera when external power is not available and use external power supplied from an external power source when available.

As discussed above, the "smart" retractor or harvester of the present invention can be used during the GSV harvesting procedure to enable direct visualization of the GSV being harvested and to provide illumination during the harvesting procedure. In one specific example, the camera 814 of the retractor is connected wirelessly or by a sterile USB cord to a portable ultrasound machine, such as Terason® t3200 or t3300, so that the display screen of the portable ultrasound machine acts as a monitor or display for the camera. In addition, when the camera is connected to the ultrasound machine or any other display screen using the USB cord, power may be supplied to the camera via the USB cord so that additional wires or batteries are not required for operation of the camera. The retractor of this invention exposes the GSV and allows for better visualization of the GSV and its branches during the harvesting procedure.

Figure 14:
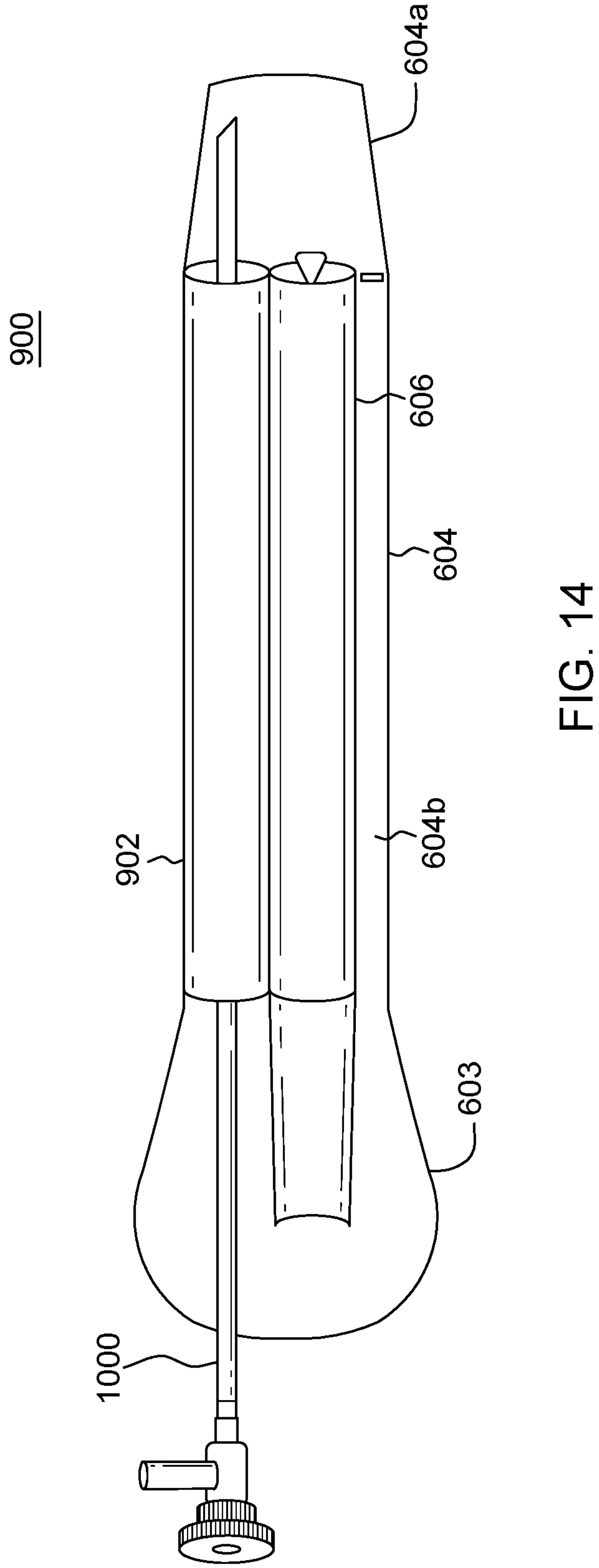
FIG. 14 shows a retractor of the present invention used with the visualization device of FIG. 10.

In another embodiment, another version of a retractor 900 is shown in FIG. 14. The configuration of the retractor 900 is similar to that of FIGS. 6 and 7, and similar features are shown using similar reference numbers. However, instead of including a camera in the retractor 900, the retractor of FIG. 14 includes a tunnel 902 formed on or connected to the blade 604 for loading a visualization device 1000, such as a cystoscope, an angioscope or an endoscope. The visualization device may be the same visualization device used for hydrodissecting the GSV under direct vision.

As shown in FIG. 14, the tunnel 902 is formed on the first surface 604*b* of the blade 604 and extends adjacent to the channel cover 606 used for smoke evacuation or fluid/gas delivery. The size and shape of the tunnel 902 is not limited to the shape shown in FIG. 4 and may be smaller in width, shorter or longer in length and/or may be formed using a solid tunnel cover permanently or releasably attached to the first surface 604*b* of the blade or using a plurality of C or U shaped attachments permanently or releasably attached to the first surface of the blade along the channel cover 606. In other embodiments, the tunnel may be integrally formed with the blade, instead of using a separate cover or attachments. In some embodiments, the position of the tunnel 902 may be varied. For example, the tunnel 902 may be provided on top of the channel cover 606 instead of to the side of the channel cover 606.

As shown in FIG. 14, the tunnel 902 is used for loading and holding the visualization device 1000 adjacent to the retractor blade 604. In the illustrative embodiment of FIG. 14, when the visualization device is loaded into the tunnel, the tip of the visualization device is placed near the tip 604*a* of the retractor for optimal visualization of the GSV during harvesting. However, in other embodiments the positioning of the tip of the visualization device may be adjusted so as to provide desired visualization of the GSV. Although not shown, in some embodiments, a locking mechanism may be used to lock in place the position of the visualization device in the tunnel 902 or relative to the retractor blade 604. The locking mechanism would prevent movement of the visualization device relative to the retractor during the GSV harvesting procedure.

Although the tunnel 902 in the retractor of FIG. 14 is used for loading the visualization device, in other embodiments, the tunnel can be used for holding other devices, as needed. In the retractor of FIG. 14, since a camera is not required to be part of the retractor, a smaller size of the retractor and lower manufacturing cost can be maintained. However, in some embodiments, the configuration of the retractor of FIG. 6 may be modified to include the tunnel for loading the visualization device. In such embodiments, the retractor would include a camera, as shown in FIGS. 8A and 8B, and would also be capable of loading a visualization device, or other devices, as needed.

In certain embodiments, instead of using the retractor of FIGS. 8A-B and 14, the hydrodissector 1200 of FIGS. 15-21 or the hydrodissector with the shovel-shaped or spatula-shaped tip described above may be used during the harvesting procedure. In these embodiments, the camera of the hydrodissector provides direct visualization and illumination of the GSV being harvested. One or more of the fluid ports 1240, 1240*a*, 1240*b* of the hydrodissector may be used for washing the GSV with fluid, such as the sodium bicarbonate solution or a solution of one or more medications mentioned above, and/or for providing a $CO_2$ infusion to the GSV. Furthermore, if needed, suction may be provided to the GSV using one of the fluid ports 1240*a*, 1240*b* to remove any excess fluids.

As discussed above, in some embodiments, the hydrodissector of FIGS. 15-21 has interchangeable tips or interchangeable bodies with different tips, so that the angled tip 1230 or the body with the angled tip of the hydrodissector in FIGS. 15-21 may be removed and replaced with another tip, such as a shovel-shaped or spoon-shaped tip, or another body with a different tip, in order to convert the hydrodissector into a retractor/harvester. As also discussed above, the shovel-shaped or spoon-shaped tip includes a camera provided on its concave surface and directed so as to provide direct visualization of the GSV when the tip is used to retract tissue around the GSV. In certain embodiments, the camera is angled between 90 and 180 degrees relative to the surface of the shovel-shaped or spoon-shaped tip. In addition, as in the embodiments of the retractor in FIGS. 6 and 7, one or more C-shaped or U-shaped attachment(s) may be removably attached to the shovel-shaped or spoon-shaped tip or to the tubular-shaped body so that the C-shaped or U-shaped attachment(s) is used for lifting the GSV. For example, one or more C-shaped or U-shaped attachments may be removably attached on the concave side of the shovel-shaped or spoon-shaped tip. The one or more C-shaped or U-shaped attachments may be attached at other locations on this convertible hydrodissector so as to optimize lifting of the hydrodissected GSV without causing damage thereto.

In certain embodiments, other devices that prevent trauma to the GSV and preserve the GSV may be utilized for vein harvesting in addition to the above-described retractor and/or hydrodissector. For example, a Vein Preparation Kit manufactured and sold by VasoPrep Surgical (vasoprep.com) may be used during harvesting the GSV. The VasoPrep Vein Preparation Kit includes a non-toxic surgical marking pen that preserves endothelial function, a pressure relief assembly that automatically limits distention pressure during preparation of the vein, a bulldog clamp for atraumatic vein occlusion, a vein cannula and cannula introducer assembly and other components such as syringes and temporary vein storage cup. Either some or all of the components of this kit may be used during GSV harvesting. Other techniques and devices which preserve the vein during harvesting are described in U.S. Pat. No. 8,691,556, assigned to Vanderbilt University, which may be used during GSV harvesting. The entire disclosure of the '556 patent is incorporated herein by reference.

In accordance with the present invention, a kit for performing the MINT procedure may be provided in order to supply the devices needed for performing the MINT procedure. In certain embodiments, the kit includes one or more of the following items: one or more needles for use in hydrodissecting the GSV, one or more disposable venous hydrodissectors having a pencil tip and/or the cone-shaped blunt tip, at least one disposable "smart" retractor/harvester with one or more U-shaped and/or C-shaped adapters, disposable clip appliers, such as clip appliers manufactured by Microline Surgical, clips, such as hemoclips, disposable scissors, disposable hook(s), disposable cauteries, disposable electrode(s) and tumescent fluid for use in hydrodissection. The kit may also include medication solutions for use after hydrodissection and other solutions and/or devices for use during the MINT procedure. The kit may also include the hydrodissector and sheath introducer shown in FIGS. 10-13, and/or the hydrodissector of FIGS. 15-19 and/or FIGS. 20A-C and/or FIGS. 21A-C as well as interchangeable tips or interchangeable bodies with different tips for the hydrodissector of FIGS. 15-19, 20A-C and/or 21A-C to enable conversion between hydrodissecting functions and harvesting functions. Moreover, the kit may also include a vein preservation kit, such as a Vein Preparation Kit manufactured by VasoPrep (www.vasoprep.com) that includes a surgical marking pen, a pressure relief assembly, a bulldog clamp for atraumatic vein occlusion, a vein cannula and cannula introducer assembly and other components such as syringes, temporary vein storage cup, etc.

Using Endoscopic ASVAL, a Modification of the Mint Procedure to Treat Varicose Veins The most popular method for treating varicose veins involves the removal or destruction of the Great Saphenous Vein (GSV). This technique is based on the "descending theory" of the etiology of varicose veins, which was first posited by Trendelenburg in 1894, when patients presenting for treatment had far advance disease. Today, the majority of patients treated for varicose veins have far milder disease with GSVs that do not have to be sacrificed for the treatment to be effective. This more modern treatment is based on the "ascending theory" of the etiology of varicose veins. The "ascending theory" posits that varicose veins start in the more superficial, thin wall veins and the GSV only becomes pathologic once a large venous reservoir develops. This allows the majority of patients to be treated by meticulous, ultrasound guided, phlebectomy such as the ASVAL technique, which can prevent the loss of the GSV. According to the CEAP Classification System, there are six levels of venous disease. The ASVAL method works well for C-2 level venous disease and for some C-3 level venous disease. However, for patients with more far advanced disease, the ASVAL method alone will not save the GSV, and this patient group would be an ideal group of candidates for Endoscopic ASVAL of the present invention.

The Endoscopic ASVAL procedure starts exactly as the MINT procedure described above, with ultrasound guided hydrodissection of the GSV from just below the knee at Boyd's perforator to the groin. A small incision is made at the knee and the hydrodissection is started as in the MINT procedure. The position of the incision and hydrodissection may be adjusted as needed for the procedure. The Endoscopic ASVAL procedure differs from the above-described MINT procedure in that the side branches which are varicosed and incompetent perforators are divided, while branches which are normal, healthy and competent perforators are left alone and are not divided. In this way, the varicosed branches of the GSV are divided while leaving the healthy branches that are competent perforators intact to ensure long-term patency of the GSV.

The abnormal branches to be divided can be identified by ultrasound preoperatively with the patient in a standing position. Once the abnormal vessels have been divided, the Endoscopic ASVAL procedure is finished with the GSV left in situ. The knee incision is closed and the patient is placed in a thigh length compression stocking. Compression therapy is continued for several weeks post-op to ensure that the GSV remains undilated while the cicatrix around the vein forms. The cicatrix formed around the GSV should act as an exoskeleton at the time it is harvested for bypass. The use of exoskeletons around venous bypasses in animal and human studies have resulted in improved hemodynamics and reduced Vein Graft Failure (VGF). At the time of bypass, the GSV and its surrounding cicatrix can be harvested using the principles developed by Dr. Keith Delman in performing minimally invasive lymph node groin dissection in patients with metastatic malignant melanoma.

The Endoscopic ASVAL procedure and any future harvesting of the GSV can be performed using the same equipment as the above-described MINT procedure, namely the echogenic needle and/or venous hydrodissector, the portable ultrasound, such as Terason t3200 or t3300, and/or the visualization device, and the "smart" retractor, all of which are described above. These procedures can all be done under local tumescent anesthesia in an outpatient setting, thus reducing the complexity and cost of the procedures and reducing patient recovery time.

As with the above-described MINT procedure, the Endoscopic ASVAL allows the adventitia of the GSV to be treated with drugs such as platelet rich plasma or stem cells to strengthen the wall of the GSV, since weakness of the vein wall is thought to be a primary cause of varicose veins. These and other drugs, as well as gene therapy, can be delivered to the GSV over several days, weeks or months, using existing technology. For example, drug therapy, stem cell therapy and/or gene therapy can be delivered to the GSV on a permanent or a bioabsorbable drug eluting stents. Other drugs, such as the ones mentioned herein above used in the MINT procedure, may be applied to the GSV to promote strengthening of the venous wall, preventing thrombosis and preventing damage to the GSV.

Figure 9A:
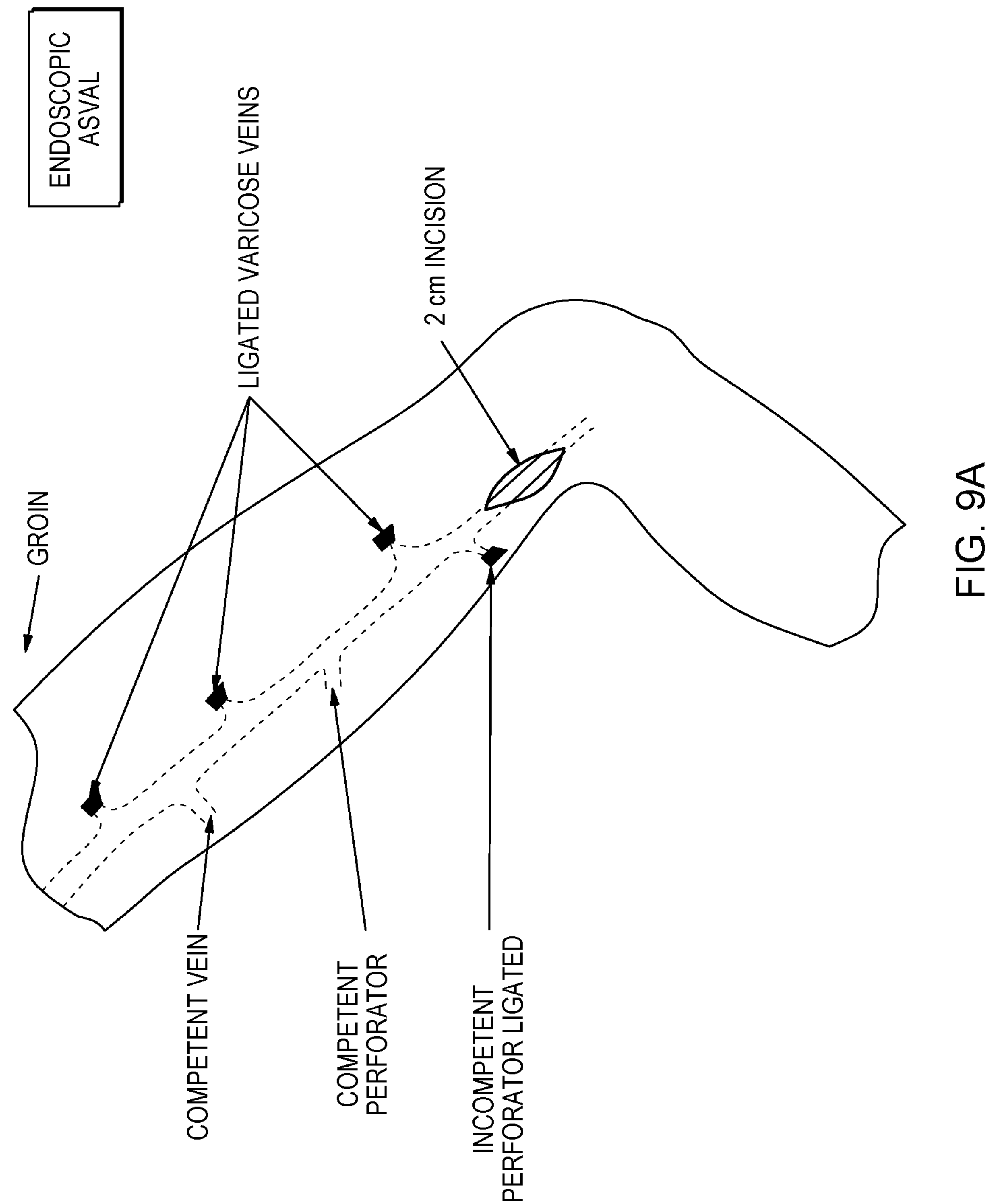
FIG. 9A shows a GSV after undergoing an endoscopic ASVAL procedure.

FIG. 9A shows a GSV after undergoing the Endoscopic ASVAL procedure described above. As shown in FIG. 9A, the procedure is performed through a 2-cm incision preferably in the knee region to hydrodissect the GSV between the knee and the groin. As also shown in FIG. 9A, incompetent perforator and varicosed vein branches are ligated while competent perforator branches are left intact. In other embodiments, the position of the incision and the size thereof may be different, and in some embodiments, the portion of the GSV treated may be between the knee and the ankle or may be the full length of the GSV. The procedure of FIG. 9A may be modified to use a diaphragm with a one-way access port, as described above with respect to FIGS. 22-26, and to perform multiple hydrodissection passes.

Figure 9B:
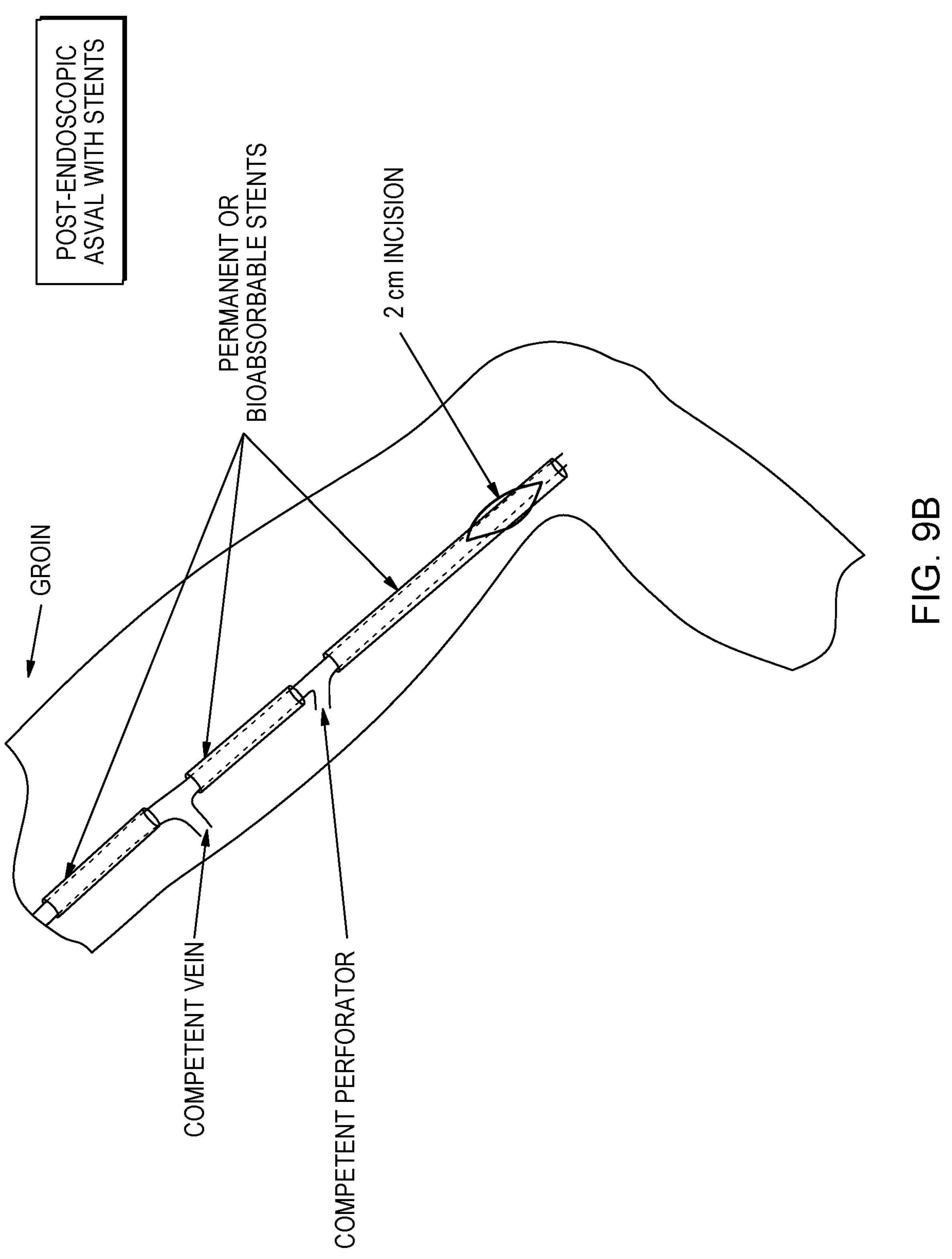
FIG. 9B shows a GSV after undergoing the Endoscopic ASVAL procedure and having bioabsorbable drug eluting stents applied thereto.

FIG. 9B shows a GSV after undergoing the Endoscopic ASVAL procedure and having bioabsorbable drug eluting stents applied thereto. As shown, the stents are applied to the hydrodissected GSV and the ligated branches in order to deliver drug therapy, stem cell therapy and/or gene therapy to the GSV. In the embodiment shown in FIG. 9B, the stents are not applied to the competent perforator branches, which are not ligated. In other embodiments, however, the stents may be applied to all branches, including the competent perforator branches and the ligated branches, or to selected branches of the GSV, as needed.

The above-described MINT procedure and the Endoscopic ASVAL procedure can also address a concern that thrombus might develop in the GSV at the time of hydrodissection. This may be prevented by giving the patient one dose of therapeutic Lovenox two hours prior to the hydrodissection. This would protect against the possibility of any intraluminal clots developing during the hydrodissection and the effect of the Lovenox would be completely neutralized by the time GSV harvesting is carried out at the time of the CABG. In certain cases, standard EVH procedure as well as the MINT procedure described above can cause intra and postoperative bleeding at the saphenectomy site leading to hematoma formation and increased leg wound complications. This complication can be avoided by infusing tumescent fluid containing isotonic sodium bicarbonate with Lidocaine and epinephrine into the potential space created by the saphenectomy at the time of the harvesting. This would also eliminate any possibility of intra or postoperative bleeding necessitating the use of drains in the leg.

While the above descriptions of the MINT procedure and the Endoscopic ASVAL procedure direct the use of a needle, such as an echogenic spinal needle, or venous hydrodissector to perform the hydrodissection under ultrasound guidance or under direct vision to make this procedure as minimally invasive as possible, other effective imaging techniques are available. For example, if the sonographic skills of the average Physician Assistant performing this procedure do not allow them to safely use an echogenic needle, a rigid 2 mm cannula can be easily placed in the saphenous space with a 7-French introducer sheath. This blunt tipped 2 mm infusion cannula completely eliminates any potential damage to the GSV at the time of hydrodissection secondary to a sharp tipped echogenic spinal needle. Alternatively, the venous hydrodissectors described above can be used instead of the needle.

The above-described MINT procedure and the Endoscopic ASVAL procedure solve a number of problems typically associated with vein dissection and harvesting procedures. First, the MINT procedure and the Endoscopic ASVAL procedure solve a problem of leg wound complications that occur with open vein harvest techniques by using a minimally invasive technique performed through a 3 cm incision. Second, the MINT procedure and the Endoscopic ASVAL procedure solve a problem of blunt trauma to the GSV that occurs during harvesting because hydrodissection of the GSV eliminates all blunt trauma during harvesting.

Another common problem occurring in conventional procedures is thrombus, both macro and micro, which occurs in about 67% of GSVs harvested with standard EVH procedures. In the present invention, addition of low molecular heparin to the perivascular space has been demonstrated to penetrate the vessel wall down to the endothelium. Also, addition of aspirin to the perivascular space has a direct protective effect on the endothelium which reduces endothelial denudation and thrombosis. The MINT procedure and the Endoscopic ASVAL procedure also solve a problem of spasms of the GSV. Specifically, addition of anti-spasmodic agents such as Papaverine or nitroglycerine-verapamil solutions, to the tumescent fluid prevents spasms of the GSV.

When the hydrodissection of the GSV is performed about 24 hours before performing a lower extremity bypass, the fascial space surrounding the GSV has to be gently re-expanded with the tumescent fluid solution containing the above-described medications, i.e., aspirin, low molecular weight heparin, Papaverine, etc. This is necessary to ensure the perivascular delivery of the aspirin, low molecular weight heparin and anti-spasmodic agents at the moment the harvesting of the GSV is started. This prevents the initiation of thrombosis, which is known to be the first step leading to intimal hyperplasia and the chief cause of vein graft failure. Therefore, at the time of vein harvest for either CABG or the lower extremity bypass, the hydrodissector and/or retractor described above used for harvesting is required.

The present invention also solves a problem of a toxic environment surrounding the GSV. In the present invention, Plasma-Lyte A solution, which is a major component of the tumescent fluid, has a pH of 7.4 compared to Normal Saline with a pH of 5.6, which is known to be toxic to the GSV. Thus, the tumescent fluid used during the MINT procedure and the Endoscopic ASVAL procedure avoids a toxic environment surrounding the GSV. In addition, the present invention solves the problem of a toxic effect of $CO_2$, which is a further cause of acidosis leading to endothelial damage. Specifically, the MINT procedure and the Endoscopic ASVAL procedure use an open $CO_2$ system and the Plasma Lyte solution is a buffered salt solution which would neutralize the effect of $CO_2$.

The MINT procedure and the Endoscopic ASVAL procedure of the present invention solve a problem of inexperienced physician assistants (PAs) damaging the GSV during harvesting, thus leading to inferior GSV patency rates. In the present invention, for lower extremity bypass procedures, where hydrodissection is performed 24 hours pre-op with an ultrasound guided spinal needle or with an ultrasound and/or direct vision guided hydrodissector, the PA can perfect the hydrodissection technique on venous patients that are having their GSVs ablated. PAs would be allowed in a cardiac suite after video confirmation of mastery of this technique on venous patients. Moreover, for CABG patients, where the MINT procedure takes place immediately prior to bypass, the hydrodissectors described above feature real-time visualization of the GSV and ultrasound monitoring of the hydrodissection will ensure complete and atraumatic dissection of the GSV. As a result, this process eliminates the learning curve needed for the standard EVH procedures.

Moreover, the MINT procedure and the Endoscopic ASVAL procedure of the present invention solve a problem of post-operative hematomas at harvest site. In the present invention, once the GSV is harvested, the site is infiltrated with tumescent fluid consisting of isotonic sodium bicarbonate with xylocaine and epinephrine added. During this procedure, no drain is used and a watertight closure is performed. Thigh length stocking and Ace wrap is applied to the patient's extremity prior to leaving the operating room.

Finally, performing hydrodissection of the GSV, as described above, about 24 hours prior to a lower extremity bypass allows the surgeon to perform this complex vascular reconstruction under straight local anesthesia since all of the dissection has already been completed the day before. As a result, the present invention substantially reduces the occurrence of surgical trauma, and the surgical trauma for this reconstruction is the same as for a simple embolectomy. Therefore, the procedures of the present invention reduce post-operative morbidity and mortality rates.

As explained, the invention provides improvements to conventional venous harvesting techniques, such as described above, the improvements including various inventive systems for implementing inventive variations of the minimally invasive no touch ("MINT") procedures. In greater detail, while the inventive MINT procedure improves the patency rates of harvested GSVs without the local leg wound complications associated with the Souza "No Touch" harvesting technique, it relies upon ultrasound to provide for visualization of the vein during dissection/harvesting. Ultrasound guidance, however, can be challenging for novice practitioners, as developing competent ultrasound guidance skills while also implementing the hydrodissection takes time and experience. Put another way, while the ultrasound-guided MINT procedure performed by an experienced medical professional for GSV harvesting is effective, the procedure requires ultrasound experience, or substantial training to master ultrasound-based navigation, of course with some risk of inadvertent undesirable damage to harvested veins during the learning.

Inventive Modified Endoscopic Vein Harvesting (EVH) System

In an embodiment, the invention foregoes reliance on ultrasound to guide EVH. Instead, the inventive method relies upon a modified conventional endoscopic vein harvesting (EVH), originally intended to use endoscopic imaging to guide a tip that relies on application of mechanical "push" energy to separate the vessel for harvesting from its surrounding tissues. That is, known conventional EVH systems utilize a dissecting end cap (blunt end) that is physically compelled against the vessel and its surrounding tissue to dislodge and separate it for extraction. And the conventional system utilizes $CO_2$ insufflation in the space through which the blunt end is forced to effect separation of the vessel from its surrounding tissue, such as nerve, connective and fatty tissue, to define the imaging environment. The inventive, modified EVH system instead relies upon injection of a hydrodissecting fluid to effect MINT-based hydrodissection (atraumatic) and to create a fluid-defined imaging environment in the space created by the hydrodissecting to support endoscopic imaging.

Figure 27A:
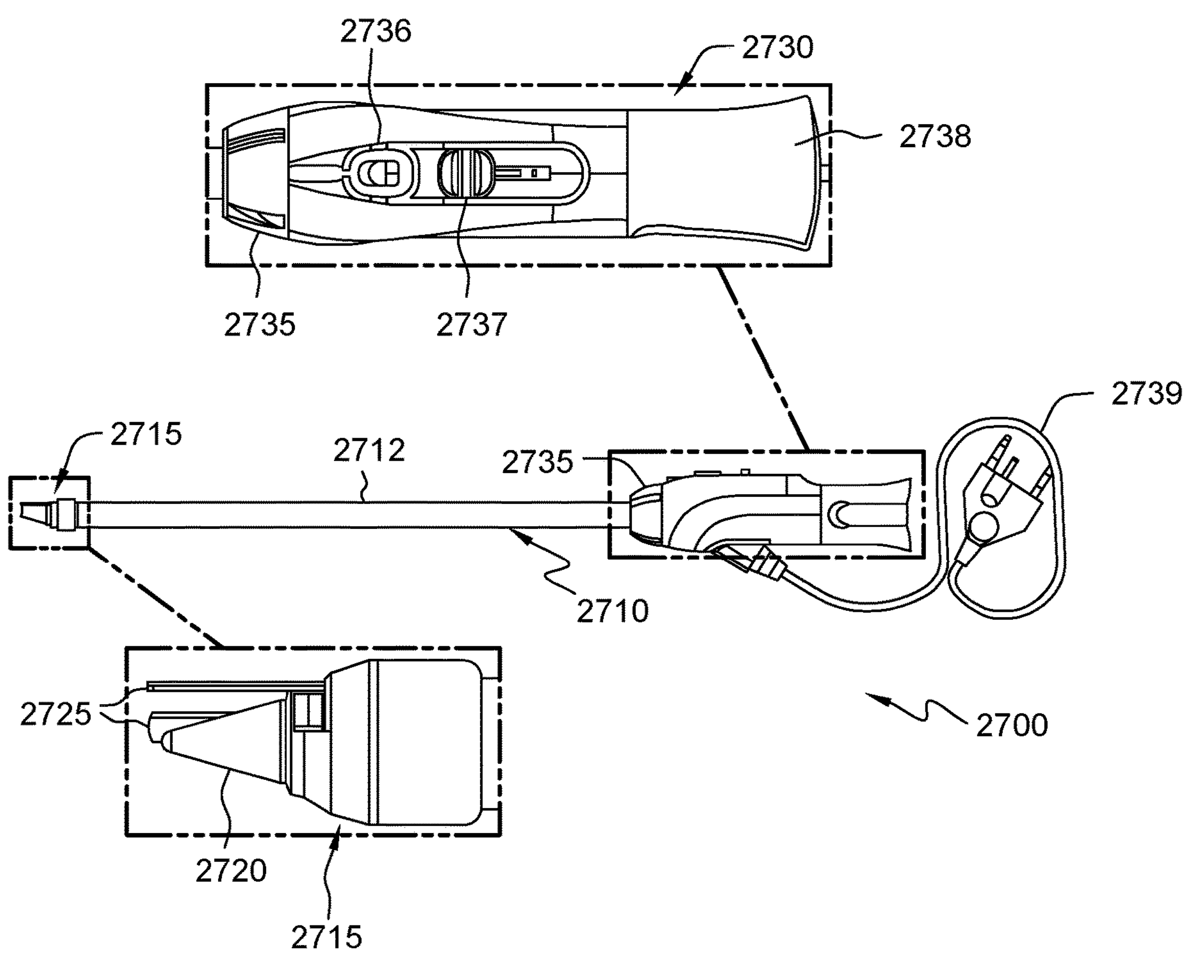
FIG. 27A shows a conventional endoscopic vein harvesting (EVH) system.

A conventional EVH system, such as the Saphena Medical Venapax® EVH system 2700, is shown in FIG. 27A. The conventional EVH system 2700 includes an elongate cannula body or shell 2710, which includes an outer surface 2712 and an internal lumen for receiving and advancing an endoscope (not shown) for visualization (image guidance). At a distal end 2715 of the cannula 2710 is an attached dissecting tip 2720 configured for blunt dissection of tissue connecting the vessel for dissection to its surrounding tissue, to isolate the vessel in a cavity or space formed during a harvesting procedure. Bipolar ligating forceps 2725 are included for vessel ligation and division. A handle portion 2730 includes a forceps rotator 2735, a power button 2736 and a forceps slider 2737. The dissecting tip 2720 as shown is conical and transparent to facilitate image pickup, where the endoscope passed through the inner lumen to the tip may be a chip-on-a-tip endoscope. The power button may be used for cautery sealing of ligated divided vessels, e.g., side vessels. The handle 2730 includes an adapter 2738 for advancing devices such as the endoscope into the lumen; a power connector 2739 is included for connecting the conventional EVH cannula to AC power.

Figure 27B:
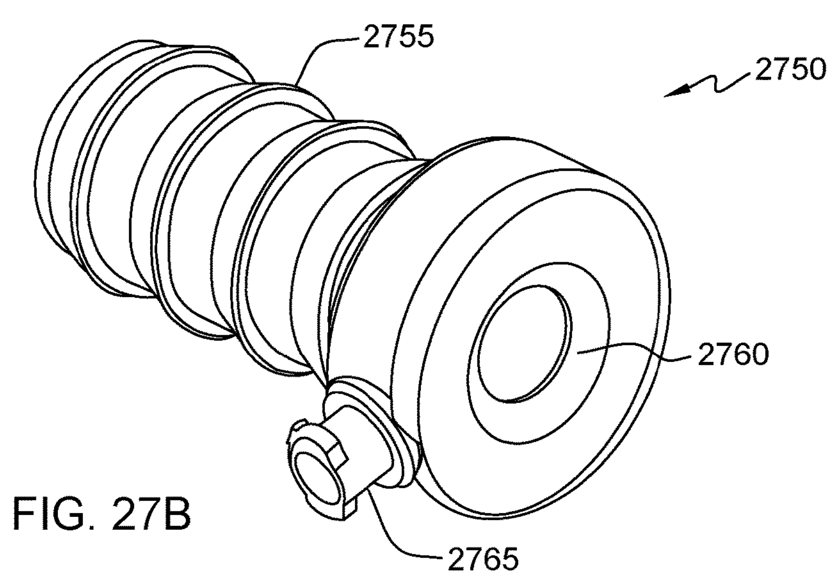
FIG. 27B shows a short, blunt tip cannula that is used with the conventional EVH system of FIG. 27A.

The conventional EVH system 2700 typically operates with a short port blunt tip cannula (BTC) 2750 (plug), as shown in FIG. 27B. The short port BTC 2750 has a short cannula body 2755 and includes a built-in gas seal 2760 that maintains fluid seal (e.g., $CO_2$, $H_2O$, etc.) with the outer surface 2712 of the elongate cannula body or shell 2710. A side port 2765 for $CO_2$ insufflation receives a supply of $CO_2$. The end of the short BTC cannula is inserted into an incision to form a seal to prevent the CO2 insufflated through the side port from leaking out as the cannula body passes through the short BTC cannula center to effect separation of the vessel, where the back end is sealed (by seal 2760) against the outer surface 2712 of the cannula.

Figure 28:
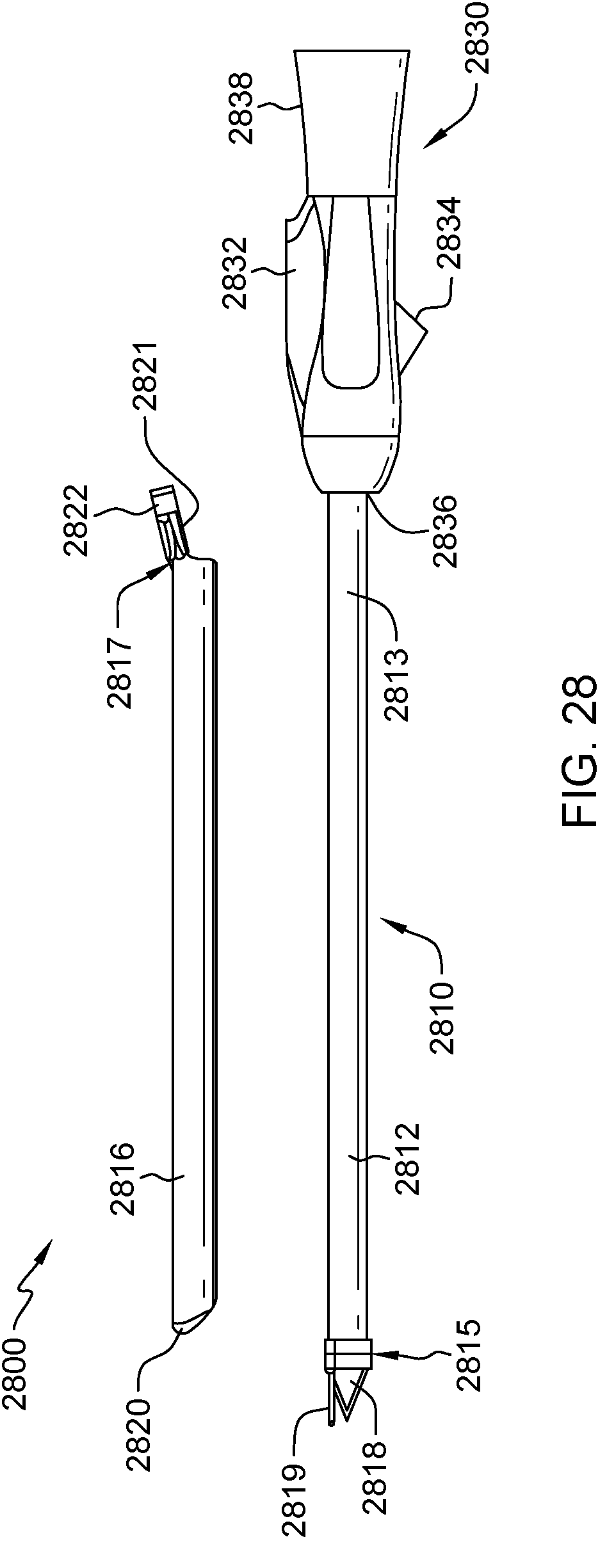
FIG. 28 shows one embodiment of a hydrodissection-based EVH system of the invention.

An embodiment of an inventive hydrodissection-based endoscopic vein harvesting (EVH) system 2800, as shown in FIG. 28, is a modified version of a conventional EVH system, such as depicted in FIG. 27A. A method of using the inventive, modified EVH system 2800 relies upon a water-based fluid solution to effect dissection, rather than blunt dissection. The water-based hydrodissecting fluid also creates a water-based fluid environment in the space created by separating the vessel from its surrounding tissue. The water-based fluid environment not only defines the endoscopic imaging environment to guide the hydrodissecting, but also may promote endothelial health in the hydrodissected vessel based on its constituent elements (e.g., Plasma-Lyte® A, L-Arginine, aspirin, low molecular weight heparin, a vasodilator, without limitation). Such water-based dissecting solutions creates a vessel environment that is preferable to a conventional $CO_2$-based fluid environment (which is acidic and dry).

For that matter, the water-based, treated hydrodissecting fluid not only allows for clear endoscopic imaging, and an endothelial healthful environment, but also provides a hydrostatic pressure in the inner cavity or space that operates to keep the surrounding tissue away from the vessel, which otherwise tends to compress inward to contact the outer surface of the vessel under procedure, limiting visibility. To that end, in addition to the hydrodissecting fluid injected to dissect the vessel from its surrounding tissue, an additional fluid portion may be insufflated through a short port BTC cannula, to maintain the separation using the hydrostatic pressure of the insufflated and/or hydrodissecting fluid.

Figure 32:
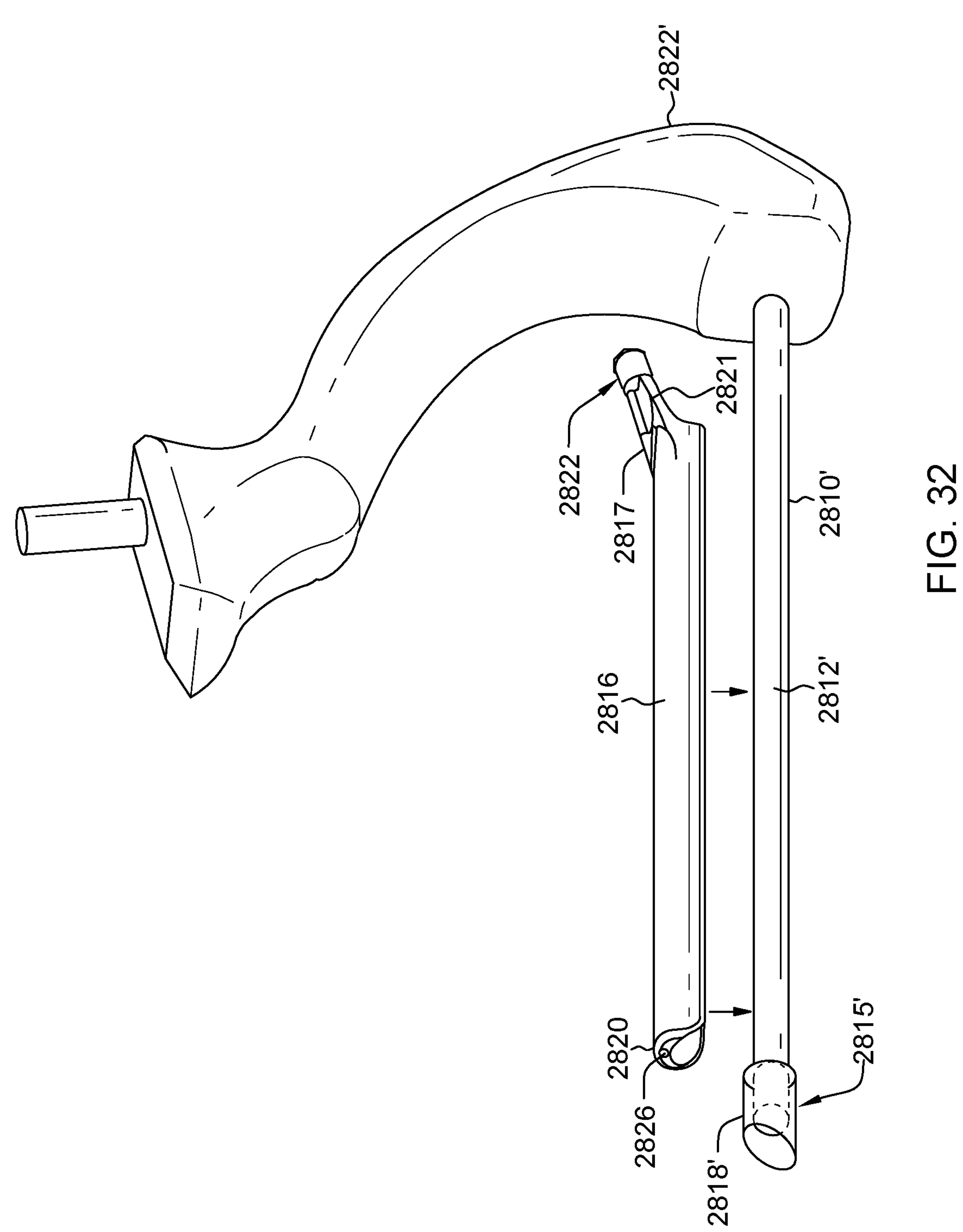
FIG. 32 shows one embodiment of a hydrodissection-based EVH system of the invention.

The FIG. 28 hydrodissection-based EVH system 2800 essentially is a modified, conventional EVH system, such as the Saphena Medical Venapax® EVII system (e.g., the EVH system 2700), or the Liva Nova Vascuclear™ EVH system (see FIG. 32). Therein, a cannula 2810 comprises an elongated body or shell with an outer surface 2812 (which is rigid). The cannula body or shell 2810 has a proximal end 28 that connects to a controller handle 2830 and a distal end 2815 to which a tip/insertion end 2818 (preferably transparent) is connected. Ligating forceps 2819 are also arranged at the cannula distal end 2815 and controlled by the handle 2830 to dissect and cauterize when powered. The preferred dimensions of the cannula are preferably the manufacturer specifications.

The modification requires the addition of a hydrodissecting section or shell 2816 to the outer surface 2812 of the elongate cannula (body) 2810. This realizes an internal volume or lumen between the outside surface 2812 and an inside surface of the shell 2816. The shell-like attachment 2816 is attached or connected to or integrally a part of an outer surface 2812 of elongate cannula (body), for example, snapped on, attached by friction fit, epoxied to, extruded as part of the elongate cannula (body) 2812, etc., as known to persons of ordinary skill in the art. For example, the attachment means may facilitate a friction fit between surface 2812 and the edges and/or inner surface of the shell, or attachment means that allow the shell to "snap on" and "snap off" the elongate cannula body as shown. This might include a rim or shoulder, or just an arrangement where there is a sufficient circumferential portion of the shell such that its ends operate as jaws that may be expanded to envelop the outer circumferential surface and then spring back to effect attachment. The shell-like attachment 2816 must create a lumen portion, once attached to the cannula 2810, that can accommodate the fluid supply conduit or channel therein. The attachment portion may be the same diameter or slightly larger than the cylindrical outside diameter of the cannula, where another part with the lumen should reflect a larger radial extent to its inner surface, again, to create a lumen or inner space sufficient to accommodate the fluid supply or conduit.

Said detachable connection preferably realizes a substantially airtight lumen between the outer surface 2812 of the elongate cannula body 2810 and an inner surface of the hydrodissection section or shell 2816. The hydrodissection shell or section preferably is made from plastic, polymer material, glass, acrylic glass, e.g., poly(methylmethacrylate), plexiglass, etc., or other suitable biomaterials, and is preferably transparent or translucent. For that matter, hydrodissection shell or section could be formed from a metallic material, e.g., stainless steel, aluminum, titanium, etc., or from a suitable plastic or polymer material.

The hydrodissecting section or shell 2816 includes an input port 2817. Preferably, a fluid communication conduit or tube 2821 extends from a fluid connector 2822 (e.g., a Luer lock connector) at the input port 2817 through the internal lumen or pathway to a hydrodissecting distal end 2820. The fluid communication tube 2821 carries the hydrodissecting fluid. A reservoir or supply of hydrodissecting fluid (not shown) is connected to the fluid connector 2822 at the input port 2817 with a connector that mates with connector 2822. The reservoir or may be pressurized. A hydrojet of the hydrodissecting fluid from the reservoir is ejected through the ejection or hydrodissecting port 2826 to effect cutting/dissection as tip/insertion end 2818 and hydrodissecting distal end 2820 are directed along the vessel for hydrodissection. Controlling the positioning of the port 2826 is carried out in reliance on endoscopic imaging. The inventive system 2800 does not rely on the tip/insertion end 2818 for blunt dissection, but only as a window for the image capture end of the endoscope in endoscopic cannula 2810.

The fluid communication tube or conduit 2821 may alternatively comprise an infusion catheter. For example, in one form, an introducer sheath (not shown) may be inserted through the infusion port 2817 and extended through the lumen created by attachment of the shell 2816. The infusion catheter, like the fluid communication conduit or tube 2821 extends to the ejection or hydrodissection port 2826 (FIG. 29) Preferably, the shell-like attachment 2816 rotates around 360 degrees. As such, the endoscopic view may be straight (0°), as in the conventional Venepax® system, or at an angle (e.g., 30°), such as in the Vascuclear™ EVH system. Hydrodissecting distal end 2820 of the shell-like attachment 2816 ejects the hydrodissecting fluid, whether from the fluid communication conduit or tube 2821, the infusion catheter (not shown) or some other hydrodissecting fluid delivery means (known to the ordinary skilled person). The aforementioned elements, where necessary, are formed from biocompatible materials, as should be apparent to persons of ordinary skill in the art.

A controller handle 2830 includes a power button 2832, a forceps slide 2834, a forceps rotator and an adaptor 2838. A foot pedal for a pump connected to the fluid reservoir and the fluid connector 2822 at port 2817 preferably is used to control fluid ejection (hydrodissecting) during a hydrodissection procedure. While not shown in FIGS. 28-31, a short blunt tip cannula (BTC) with a cannula body, built-in gas seal and hydrodissecting fluid insufflation port is included to slide onto an outer surface of the shell 2816 and exposed portion of the outer surface 2812 of the cannula 2810, when the shell 2816 is detachably connected to the elongate body 2810. Hydrodissecting fluid is added through a side port as needed to maintain the tumescent hydrodissecting fluid in an inner cavity or space formed first by an incision for entry and once hydrodissection is initiated, enlarged as hydrodissecting is carried out.

Figure 29:
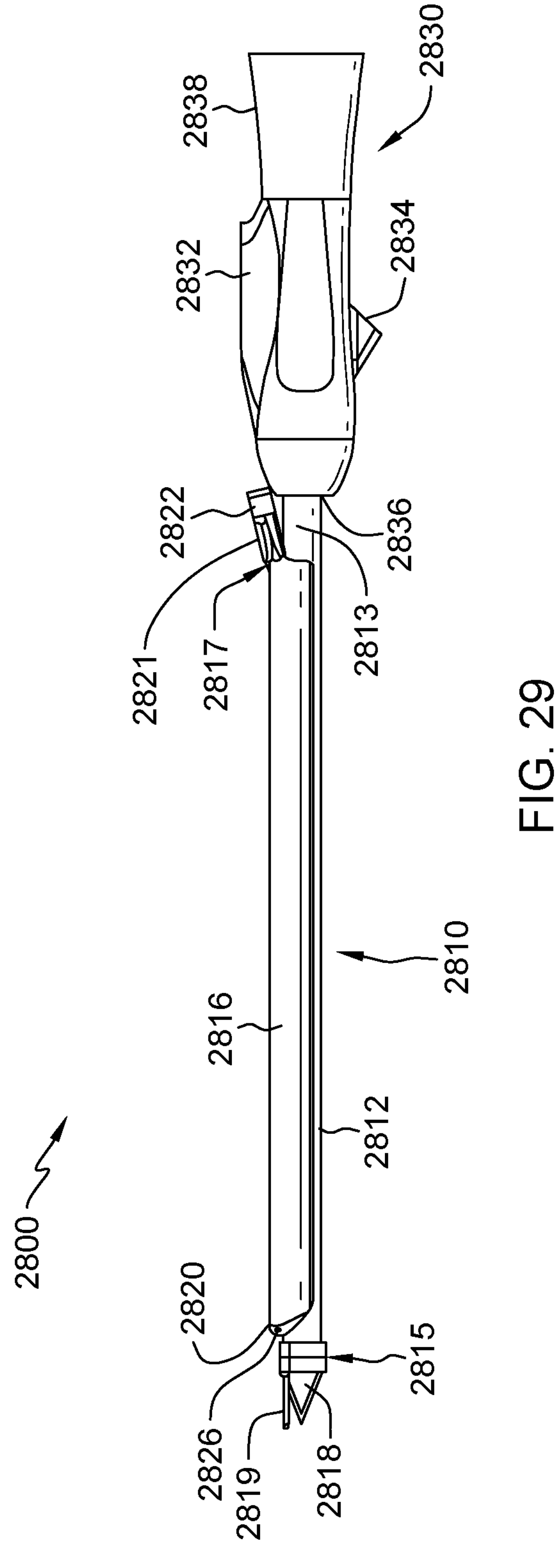
FIG. 29 presents a side plan view of the inventive hydrodissection-based EVH system embodiment of FIG. 28.

FIG. 29 presents a side plan view of the inventive hydrodissection-based EVH system 2800. The EVH system 2800 therein is shown with the shell-like attachment 2816 attached to the elongate body of cannula 2810. And as explained, a conventional endoscopic insertion tube (endoscope) with an imaging end is inserted into and through the cannula 2810 for endoscopic imaging to capture image data through a window or lens in the transparent blunt tip in order to guide the hydrodissection procedure. A proximate end of the endoscope is connected to a processing part, such as a display device (preferably portable) via adapter 2830. While the transparent blunt tip 2828 is included for conventional use as a blunt dissector, it only is used for imaging in the inventive, modified hydrodissection-based EVH system 2800, which obviates any need for blunt dissection by relying on endoscopically guided hydrodissection to effect separation of the vessel from its surrounding tissue. The ligating forceps 2819 may be used to support hydrodissection, for example, by dividing and cauterizing side vessels (when powered).

Figure 30:
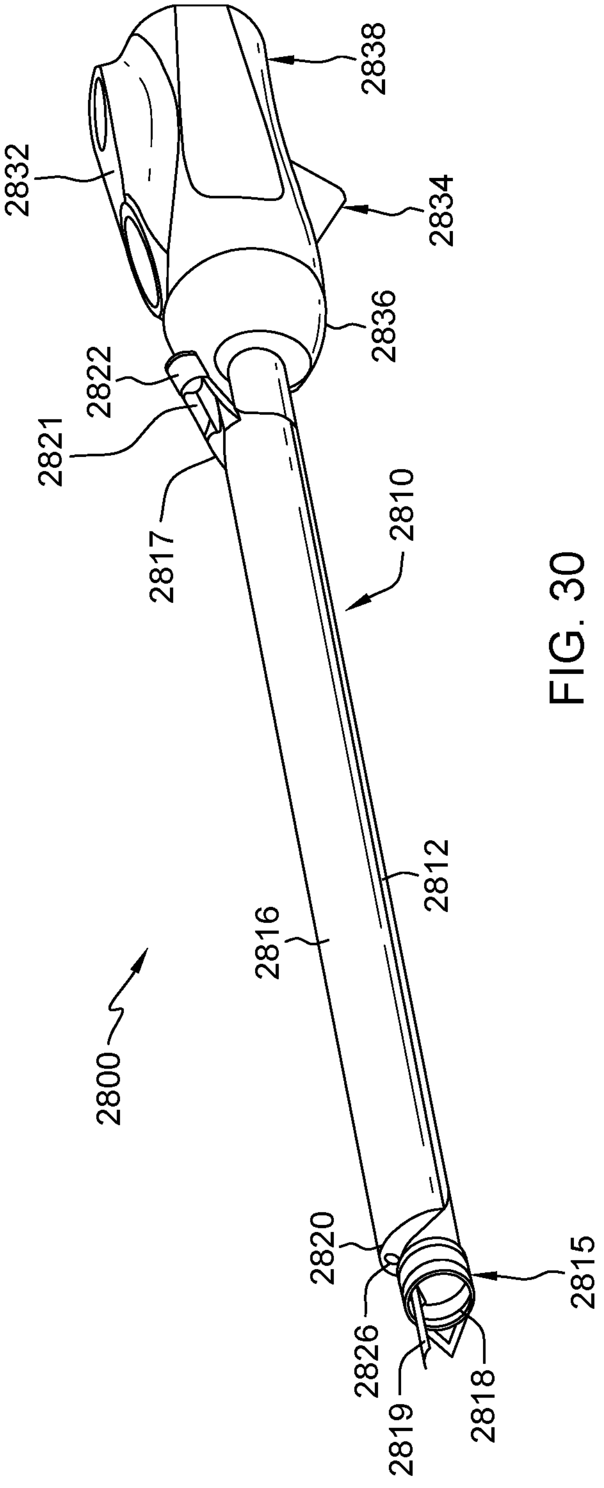
FIG. 30 presents a side perspective view of the inventive hydrodissection-based EVH system embodiment of FIGS. 28 and 29.

FIG. 30 presents a side perspective view of the inventive hydrodissection-based EVH system of FIGS. 28 and 29, with the shell-like attachment 2816 attached to the cannula 2810 of the modified EVH system. As explained above, the controller handle 2830, in reliance upon various control input elements, such as the power button 2832 and forceps slider 2834, provides for controlling the modified hydrodissection-based EVH system operation, i.e., cutting and cauterizing; the endoscopic imaging means and hydrodissecting fluid pump/reservoir provides for the image-controlled hydrodissecting. Please note that a fluid constrictor may be included to impose a sufficient velocity at which the hydrodissecting fluid is ejected from port 2826 to effect the hydrodissecting. Such a constrictor may be attached at a proximal end to the distal end of fluid communication conduit or tube 2821 (for example, inserted into or connected to an end of the conduit), where the constrictor distal end is arranged at or extending slightly from the ejecting port 2826.

Figure 31:
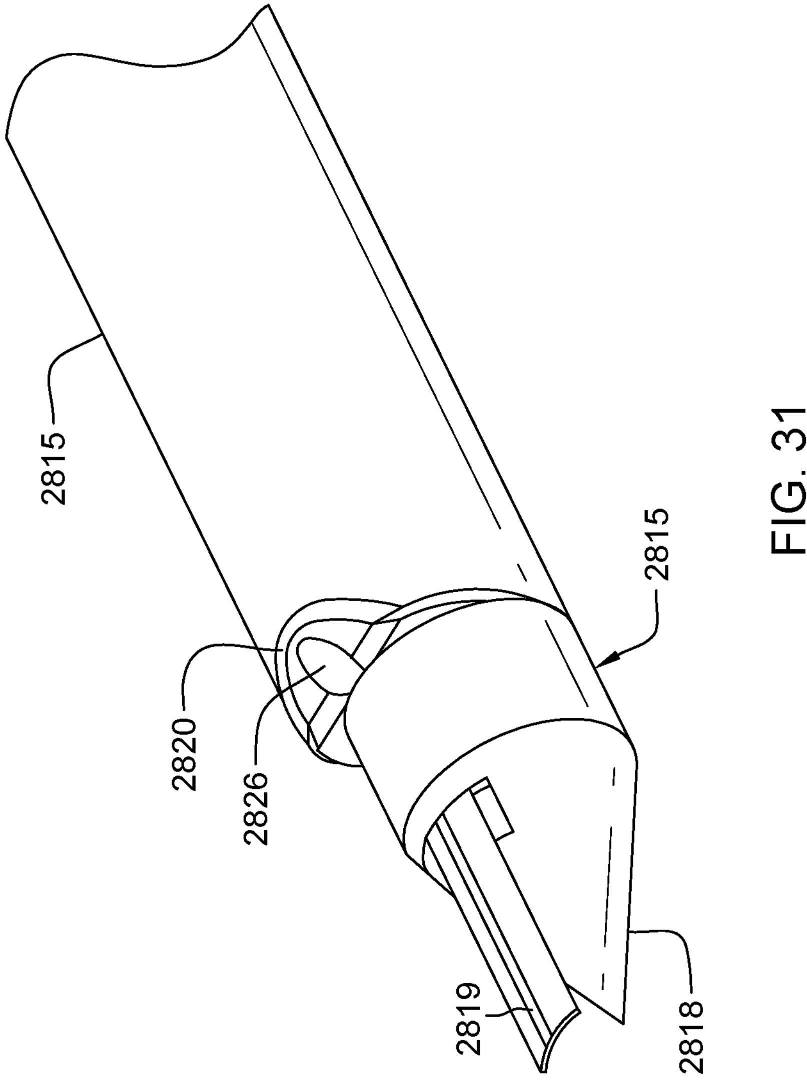
FIG. 31 presents an enlarged view of a front portion of the hydrodissection-based EVH system embodiment of FIGS. 28-30.

FIG. 31 presents an enlarged view of a front portion of the inventive hydrodissection-based EVH system 2800, with the hydrodissecting shell 2816, including the hydrodissecting distal end 2820 and ejection port 2826, attached to the cannula 2810. The cannula 2810 includes its tip/insertion end 2818 at insertion end 2815 and ligating forceps 2819. The FIG. 31 depiction highlights the hydrojet opening (through which hydrodissection fluid is ejected) for separating the GSV from the tissue to which it is connected. As shown, the bipolar ligating forceps 2819 are in an extended state for cutting. Please note that the tip/insertion end 2818 is detachably connected to the cannula distal end 2815.

FIG. 32 depicts another inventive, modified hydrodissection-based EVH system 2800', which was transformed from a Liva Nova (Sorin Group) VASCUCLEAR™ EVH system (not shown), according to the inventive principles. Therein, an elongate body of cannula 2810' is shown attached to a controller handle 2830'. A shell-like attachment 2816 is attached or connected to or integrally a part of an outer surface 2812' of elongate cannula (body) 2810', for example, snapped on, attached by friction fit, epoxied to, extruded as part of the elongate cannula (body) 2812, etc., as known to persons of ordinary skill in the art. While the physical dimensions of the modified conventional EVH systems preferably are those defined by the manufacturers (see FIGS. 27 and 32), they are not limited thereto, but may be modified to fit the needs of a desired application. The dimensions of the attachment shell or body must follow those of the known cannula body and other common elements, as should be understood by the person of ordinary skill in the art. The controller handle 2822' is used to manually insert the EVH system 2800" and image (an endoscopic means is arranged within the cannula (body) 2810' (which is rigid) with an imaging end at the distal end 2815' to guide the hydrodissection.

Like the FIG. 28 embodiment, the hydrodissecting section or shell 2816 provides an inner volume or lumen through which a fluid conduit 2821 (with a fluid connector 2822) is arranged from shell input port 2817 to the ejection port 2826 at hydrodissecting distal end 2820. The shell 2816 detachably attaches to an outer surface of the cannula elongate body 2810'. The endoscopic insertion tube with an image pick-up end extends through the cannula 2810' to tip or end 2816'. The hydrodissecting fluid is ejected out of ejection port 2826 at end 2820 to separate a vessel such as the GSV from its surrounding tissue. And as explained, the hydrodissecting fluid preferably is infused with various agents so that after the fluid does its job as both the hydrodissecting medium and a tumescent fluid that surrounds a separated vessel in a healthful, nurturing environment, such as to promote endothelial tissue health, as explained above.

A manufacturer seeking to construct an inventive hydrodissection-based EVH system according to the inventive principles can begin with a Venapax® system, a Vascuclear™ EVH system, or like conventional EVH systems, modified where necessary attach the hydrodissecting shell or section, attach a hydrodissecting fluid supply and control the EVH system and application of the hydrodissecting fluid under endoscopic guidance.

Endoscopic Ambulatory Selective Varicose Vein Ablation Under Local Anesthesia (ASVAL) Technique As discussed above, a significant number of those afflicted with coronary artery disease (CAD) also might require treatment for varicose veins, and vice versa. And frequently, varicose vein treatments are required at in earlier stage in such person's lives than is the CAD treatment. But in conventional varicose vein treatment, the treatment focus is on ablating the vein, which can also affect surrounding veins, such as the GSV. The instant inventive embodiment provides support for those dual disease sufferers by providing a process for treating a patient's varicose veins without destroying the GSV. Such treatment maintains the GSV so that it is available for a coronary artery bypass graft (CABG) procedure subsequently, as persons with CAD likely will need their GSV for CABG.

Historically, destruction of the GSV was first performed in 1894 by Trendelenburg. At that time, a typical venous patient presented for treatment with far advanced vascular disease needed immediate relief. Trendelenburg's approach was based on the so-called descending theory of the etiology of varicose veins, whereby reflux of the GSV was thought to be the primary cause of varicose veins. That being said, over the past 20 years or so, the so-called ascending theory of the etiology of varicose veins has become popular in the medical community. The ascending theory posits that the varicose veins start in the more superficial and thinner walled veins of the leg and once the varicose veins become numerous enough, they increase the venous reservoir. The venous reservoir interferes with flow through the GSV and causes valvular dysfunction and GSV dilation and incompetence. In many cases of mild venous disease, meticulous phlebectomy, implemented as endoscopic ambulatory selective varicose vein ablation under local anesthesia (ASVAL) is found to effectively treat the varicose veins and restore the GSV to normal diameter and competence. In far advanced veinous disease, however, the GSV is too large and incompetent to be salvaged and must be ablated.

In intermediate level venous disease, the GSV may be salvaged by the inventive endoscopic ASVAL procedure now described in detail. This endoscopic ASVAL technique is a MINT procedure, where the varicose veins (thin walled or superficial) are first removed in reliance on a conventional procedure. Next, the CSV is hydrodissected in reliance upon a MINT procedure whereby the varicose branches and incompetent perforators are divided with bipolar cautery. But additionally, the normal branches and perforators are left in situ with the hydrodissected GSV. In this way, the GSV is maintained by the body until that time that it might be needed for a CABG (in case of CAD).

Additionally, according to the inventive principles, the tumescent fluid surrounding the hydrodissected GSV (insufflated and remaining after being provided for the actual hydrodissecting) treats the GSV in the state it is in at the medical intervention. The tumescent hydrodissecting fluid, which comprises a water-based solution that includes additives to facilitate endothelium health, is further infiltrated with resorbable beads containing A-Cell (an A-Cellular matrix derived from porcine bladder) in an extracellular matrix. In vivo, the A-cell is released over the next four weeks after the varicose vein procedure. The A-Cell recruits m2 macrophages that promote the deposition of site appropriate tissue rather than scar during the healing process. This goal of the inventive treatment is to realize a normal diameter and competent GSV, post operatively.

Such treatment has the effect of minimizing damage such that the GSV may be dissected but not removed, so that it will be available for harvesting at a later date. The technique also requires that during the post-procedure time the patient wears two pairs of class ii thigh length stockings, for example, for four weeks (post hydrodissection). The use of these stockings after the described A-cell treatment supports maintaining a normal diameter and competence of the GSV. Again, the intact GSV so treated can be used as an autotransplant at a time in the future where a GSV transplant for a CABG might be needed.

Vest Procedure

For that matter, even damaged GSVs could be saved by utilizing this inventive MINT-based ASVAL procedure. For example, consider a diabetic patient in his 50's with severe CAD and multiple coronary artery stents already in place. Such a patient is a likely candidate for a CABG procedure. Many lower extremity bypass procedures have been successfully performed on such CAD patients utilizing a varicosed GSV. For such patients, the inventive endoscopic ASVAL procedure is considered safe. Implementing a lower extremity bypass procedure according to the inventive principles may include placing the GSV in a subcutaneous position that can easily be monitored for aneurysmal dilation using duplex ultrasound. And until recently, using a varicosed GSV would have been considered too dangerous to do for CABG, since the GSV cannot be easily monitored in the chest and any aneurysmal dilatation or bleeding could prove catastrophic results if positioned therein.

To overcome this potential problem, a vest procedure is further implemented that places a cobalt-chrome braid around the GSV at the time of CABG. Such external stenting of saphenous vein grafts reduces intimal hyperplasia, improves lumen uniformity and reduces oscillatory shear stress. The cobalt-chrome braid surrounding the GSV at the time of the CABG has already been demonstrated to be safe and effective in clinical trials. Therefore, its use with varicose veins should follow the known medicine preventing any dilatation or bleeding of a thin walled GSV once transplanted. Put another way, reliance upon the vest procedure, when it is required, insures the ready availability of a GSV autotransplant at the time of CABG in thousands of patients with both CAD and varicose veins.

Figure 33:
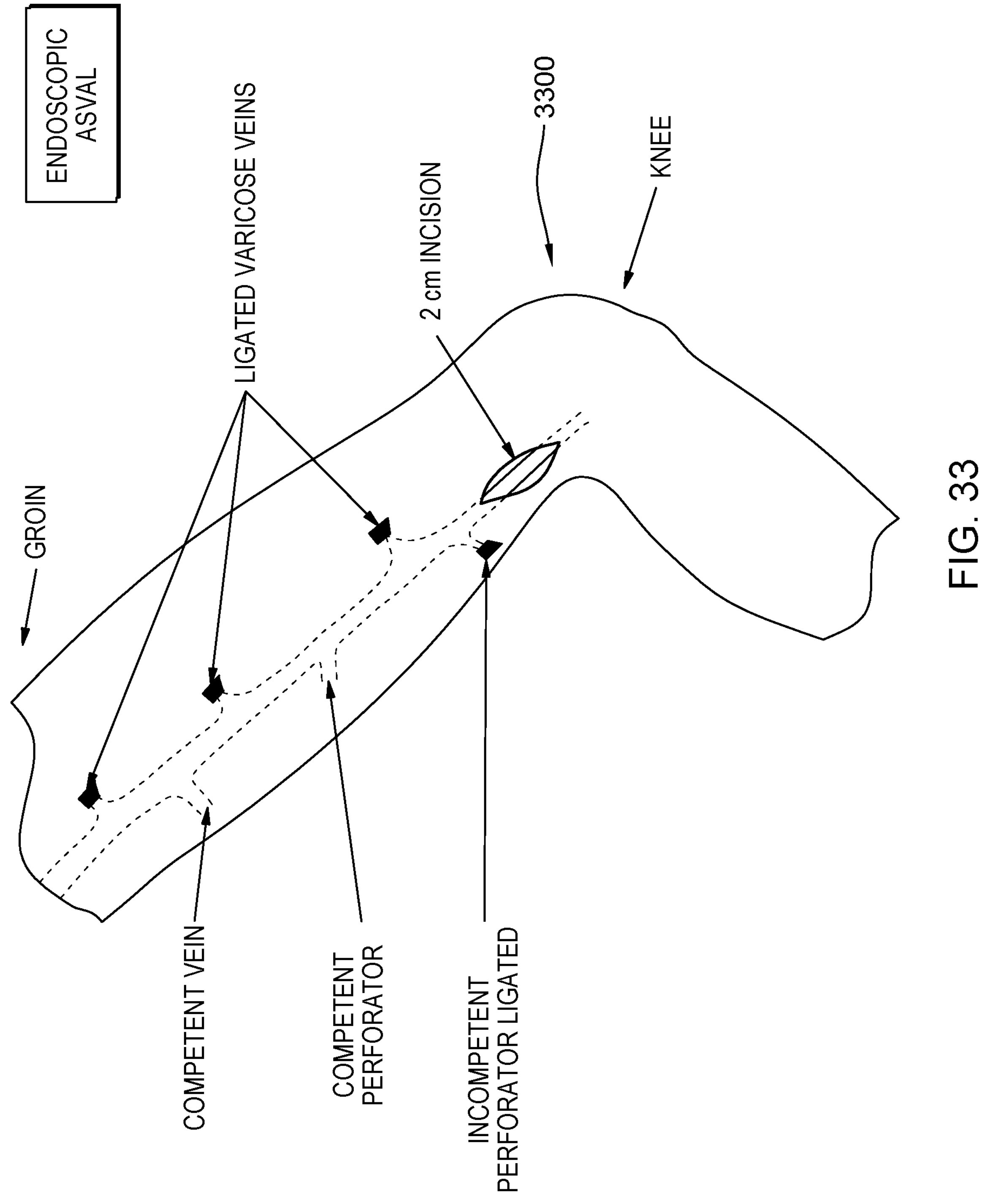
FIG. 33 is a representative image of a patient's leg after the patient has been treated for varicose veins using the inventive endoscopic ASVAL procedure.

FIG. 33 herein presents a representative image of a patient's leg 3300 after the patient has been treated for varicose veins using the endoscopic ASVAL procedure explained above. In the example depicted, the endoscopic ASVAL procedure was implemented via a small 2 cm incision proximate the patient's knee. Three (3) varicose veins were ligated using a hydrodissection-based endoscopic vein harvesting (EVH) system, described above, and one incompetent perforator on the lower left was ligated. As shown, a competent vein and competent perforator were not ligated, as they were healthy and could be maintained and the GSV maintained, post-treatment, until that time that the GSV could be needed for a CABG procedure related to the patient's CAD. But maintaining rather than destroying the GSV, making it available at a later time if needed, should save the lives of patients who might otherwise not have such a replacement vessel available.

Endoscopic-Assisted Perforate Invaginate (Pin) Stripping of the Superficial Great Saphenous Vein As explained above, the removal or ablation of an incompetent greater saphenous vein (GSV) is frequently an important step in the conventional treatment of varicose veins.[1] In many cases, the GSV is deep enough so that it can be thermally or chemically ablated without leaving any staining or unsightly scarring on the overlying skin. In certain cases, however, usually during treatment of thin females, the GSV is very superficial and chemical or thermal ablation can result in an unsightly "racing stripe" along the course of the GSV. Racing stripes are a permanent cosmetic defect. Under these circumstance, the most cosmetically acceptable approach is perforate invaginate (PIN) stripping of the GSV. The inventive hydrodissection-based EVH system and method also facilitates perforate invaginate (PIN) stripping.

A perforate invaginate (PIN) stripping technique involves stripping the vein into itself in a manner like turning a stocking inside out. PIN stripping essentially removes or ties off the GSV in the leg to treat varicose veins. The PIN stripping technique requires inserting an instrument called a PIN stripper through a small incision in the leg, whereinafter the PIN stripper is advanced through the vein. The end of the PIN stripper is sewn to the end of the vein, which will typically require a second incision at the distal end of the target vessel for PIN stripping. The PIN stripper and, thereby the vein, is then pulled in on itself as it is stripped out of the leg. PIN stripping is performed in a hospital operating room or outpatient surgical center under general anesthesia or local anesthesia with IV sedation.

If the GSV is thick walled and strong, pin stripping can be successfully performed. However, if the GSV is thin walled and fragile, pin stripping cannot be performed because the GSV tears away from the pin stripper and either a piece of the GSV is left behind in situ or additional incisions must be made to remove the entire GSV. One of the most important reasons that the ASVAL phlebectomy technique works is that the entire varicose vein is removed so no scarring or staining is possible.

This inventive principle is applicable with pin stripping of the GSV. So, and when dealing with a gossamer-like, incompetent GSV that is likely to tear during pin stripping, endoscopic assistance is a useful adjunct to the procedure. Hence, the invention provides a novel PIN stripping technique whereby the PIN stripping is carried out in routine fashion except that prior to blindly stripping the GSV, a 5 mm endoscope is introduced into a tumescent fluid comprising anesthesia around the GSV. Such tumescent anesthesia is left from the instantly prior hydrodissection procedure carried out with the inventive, modified hydrodissection-based EVH system using a 5 mm watertight cannula.

As the GSV is being PIN stripped, the endoscope of the inventive, modified hydrodissection-based EVH system follows the course of the great saphenous vein (GSV) and visualizes the branches and perforators coming off the GSV. Under direct vision, the branches can be atraumatically divided with the bevel of a 16 gauge needle placed percutaneously. This action leaves no permanent scar. Such novel and non-obvious technique, in reliance upon the inventive, modified hydrodissection-based EVH system, ensuring that the GSV will be removed in its entirety in an atraumatic fashion, and requiring only a 1 cm incision at the groin and a 1 cm incision at the knee (in reliance upon the inventive hydrodissecting techniques and modified EVH or cystoscope systems described herein.

Modified AMBU Cystoscope

In an embodiment, the inventive MINT procedure is implemented with use of a conventional cystoscope modified by attachment of an inventive cap or tip, with a window or lens to better enable the endoscope to capture images, with a constrictor that increases the velocity of fluid ejection to facilitate hydrodissection and with an ejection port for ejecting the hydrodissecting fluid under pressure sufficient to hydrodissect the target vessel without damaging it. The cap or tip preferably is transparent but may be translucent as long as the image signal may be received through the window or lens. The unmodified cystoscope ejects a tumescent fluid as an imaging medium, for example, to better image an internal volume of a bladder, so ejection pressure to effect such imaging is minimal, as distinguished from a pressure required for using a fluid jet for hydrodissection in the modified version with the inventive tip or cap.

Figure 34A:
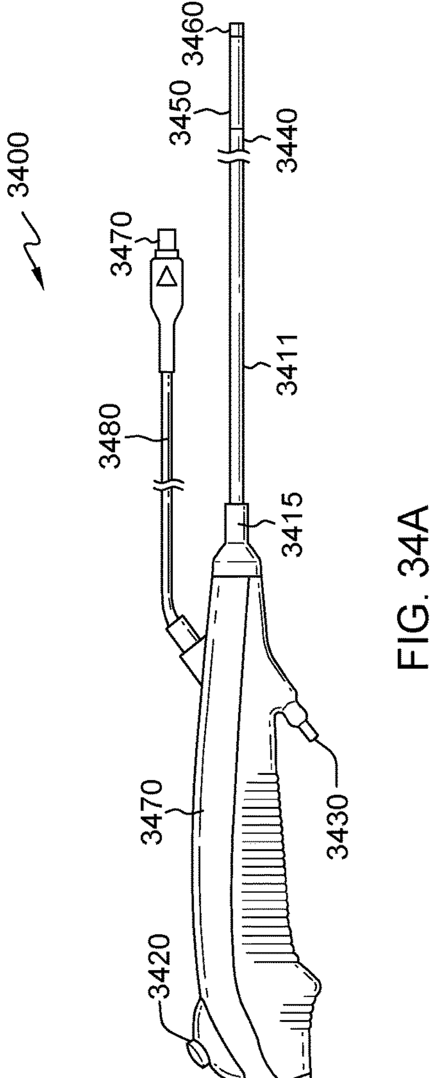
FIG. 34A shows a conventional Ambu® aScope™ 4 Cysto single-use flexible cystoscope.
Figure 34B:
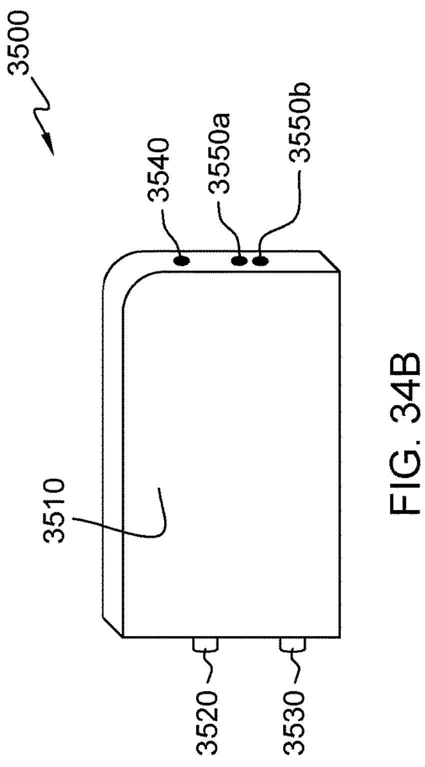
FIG. 34B shows as portable monitor that may be used with the conventional cystoscope of FIG. 34A.

FIG. 34A presents a system-level diagram of a conventional cystoscope. The conventional cystoscope shown is the Ambu® aScope™ 4 Cysto single-use flexible cystoscope ("flexible cystoscope"). FIG. 34B presents a representative view of an imaging display subsystem that receives, processes and displays the image data captured by the flexible cystoscope. The imaging display subsystem shown is a 12.8" HD aView2 Advance (portable) monitor ("portable monitor"). Both the flexible cystoscope and portable monitor are manufactured and/or distributed by AMBU, Inc., 6721 Columbia Gateway Drive, Columbia MD 21046 U.S.

The flexible cystoscope 3400 includes a handle 3410, suitable for left or right hand use. The handle is configured with a bending lever 3420, which is pressed by hand to move a distal end 3460 of the elongate, flexible insertion cord or tube 3440 up and/or down in a single plane. A working channel entry 3430 allows for instillation of fluids and insertion of endoscopic accessories. A working channel (not shown) extends from the working channel entry to a working opening (see FIG. 34B) at the to a distal end 3460. Attached to the elongate, flexible insertion tube 3440 is a bending section or maneuverable part 3450 (maneuvered by bending lever 3420). The distal end 3460 contains the camera, light source (two LEDs) as well as the working channel exit (FIG. 34B). Together, elements 3440, 3450 and 3460 may be said to comprise an insertion portion, i.e., an ensemble of the insertion cord, bending section and distal end. A cable 3480 connects the flexible cystoscope to a connector 3470, which connector connects the cable and flexible cystoscope (cystoscope handle) to a socket (e.g., a blue socket) on the portable monitor 3500 (FIG. 35B).

Portable monitor 3500 includes an interactive display screen 3510, for displaying images picked up by the camera at the distal end 3460. The portable monitor includes two endoscope connects 3520, 3530. A charging/power port or connector 3540 receives AC electrical power. Two USB ports allow data exchange, and other USB functions.

Figure 35:
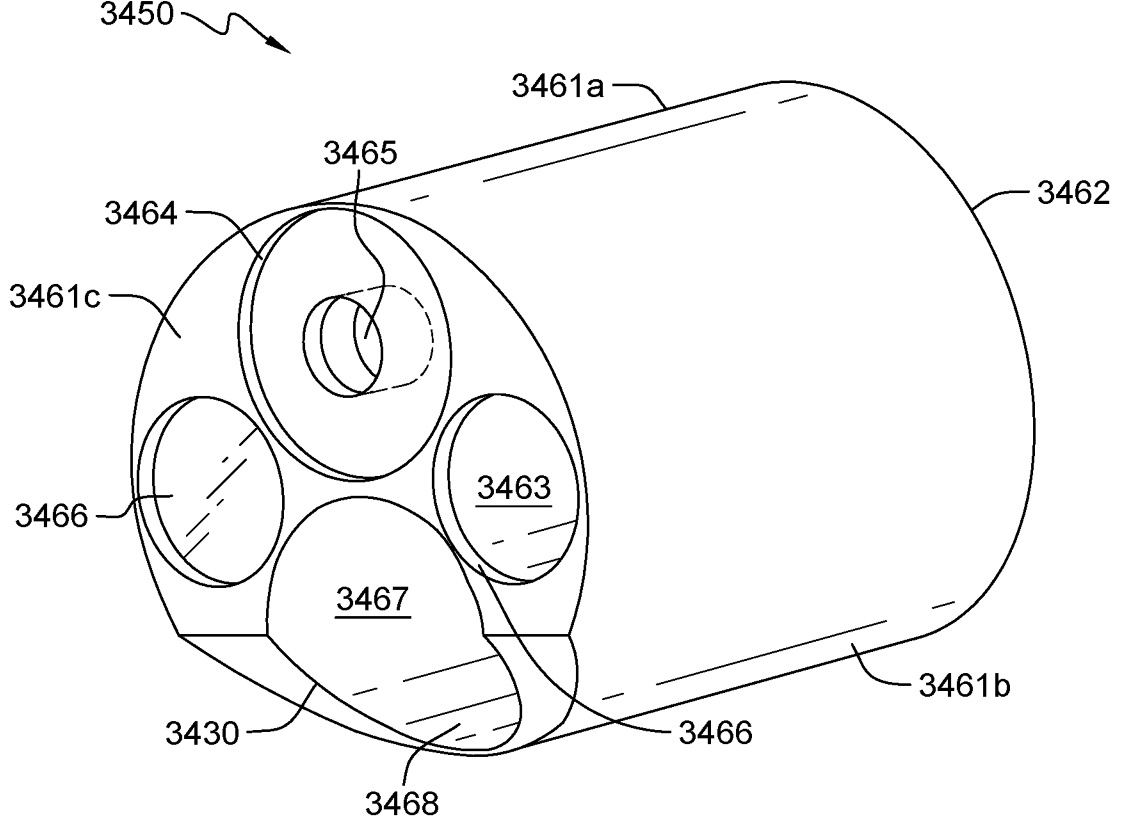
FIG. 35 shows an enlarged, side perspective view of a distal end of the conventional flexible cystoscope of FIG. 34A.

FIG. 35 presents a perspective side view of the tip part 3450 of the flexible cystoscope 3400. The tip part 3450 has an exterior housing 3461*a*, with a cylindrical circumferential wall 3461*b* and a distal front wall 3461*c*. the circumferential wall 3461*b* extending in the proximal-distal direction from the distal front wall 3461*c* to an open proximal end 3462 (prior to attachment to or with the bending section 3450) of the housing 3461*a*. The open proximal end 3462 is for connection to other parts of the device, including, for example, an outer sheath 3441 of the insertion cord or tube 3440. the bending section 3450, etc. The distal front wall 3461*c* and the circumferential wall 3461*b* enclose an interior space or volume 3463. A camera assembly is arranged in a distal camera compartment and comprises a lens stack 3464 with a sensor pick-up device 3465, for example, a charged coupled device (CCD) for endoscopic image capture. Lights, such as LED lights 3466 are included in ports to the inner space or volume 3463. A working channel 3467 is shown with an internal working channel opening 3430. An ejecting port 3468 of a fluid supply conduit or tube is arranged in the working channel 3467 at the working channel entry or opening 3430. Preferably, all of the physical dimensions of the conventional cystoscope are those defined by the manufacturer, but theses may be modified to accommodate a particular application of the inventive, modified system with the distal end cap, which will now be described with reference to FIGS. 36A, 36B, 36C and 36D.

Figure 36A:
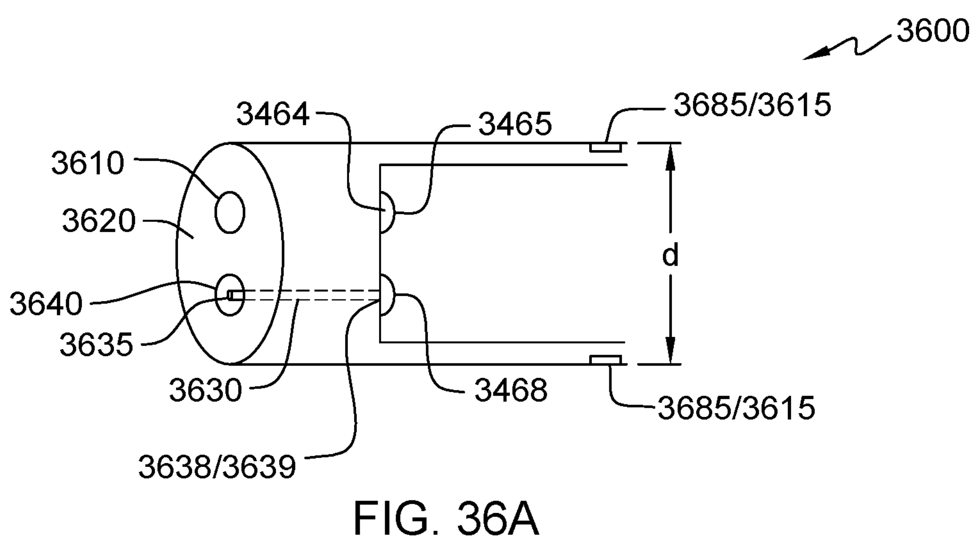
FIG. 36A shows an embodiment of an inventive end cap attached to the distal end of the conventional cystoscope to convert the cystoscope to a hydrodissector.
Figure 36B:
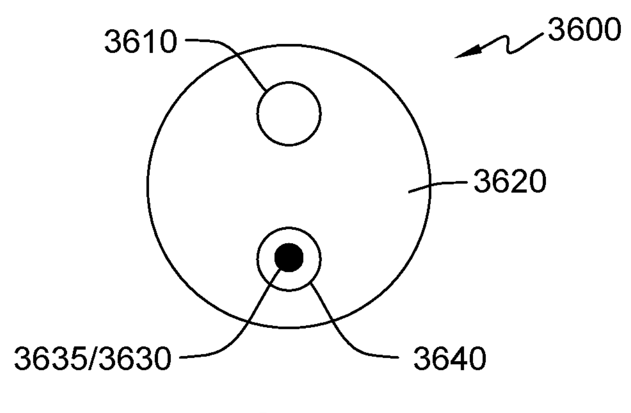
FIG. 36B shows a frontal plan view of the inventive end cap embodiment shown in FIG. 36A.
Figure 36C:
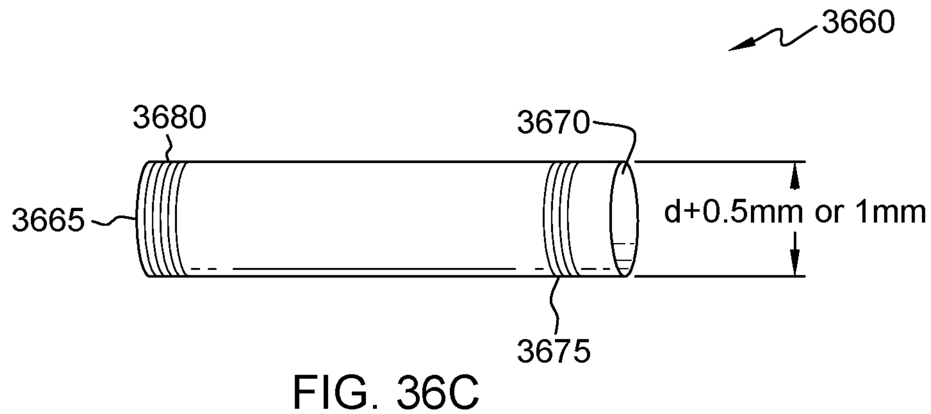
FIG. 36C shows an embodiment of a substantially rigid sleeve or tube that is positioned over a flexible elongate endoscope or cystoscope body to impose substantial rigidity to same.

In an embodiment, the invention provides a modified flexible cystoscope (system) to increase the ejecting fluid (hydrodissecting) pressure and to better facilitate imaging in the space between the target vascular vessel under hydrodissection and the surrounding tissue, once separated. An inventive MINT procedure may be implemented in reliance upon the modified, flexible cystoscope. FIG. 36A presents a perspective side view of one embodiment of the end cap 3600; FIG. 36B presents a frontal plan view of the end cap embodiment.

The inventive modified cystoscope includes a conventional cystoscope and an end cap that receives the distal end 3460 of the cystoscope, preferably configured with an image enhancement window to better capture image signals, for example, with the lens stack 3464 and image pick-up device 3465, independent of whether the insertion cord or tube 3640 is transparent or translucent. The end cap 3600 houses or comprises a fluid constrictor 3630 with a proximal end 3638 that connects to or is integral with the end cap and is in fluid communication with the conventional ejecting end of the fluid supply conduit 3639 or ejecting port of same at or slightly extended out from the working channel entry or opening 3430 of the cystoscope.

The proximal end 3638 of the constrictor 3630 may be formed to be inserted into the ejecting port 3468 at the distal end 3635 of the fluid supply conduit or tube of the elongate cord or tube 3440 of the cystoscope (system). Alternatively, the proximal end 3638 of the constrictor may include a connector that connects to the distal end of the fluid supply and/or a connector thereat, using connecting means as known to those of ordinary skill in the art. The constrictor pressurizes the hydrodissecting fluid. The distal end 3635 of the constrictor ejects the pressurized hydrodissecting fluid. The distal end of the constrictor is positioned, for example, mounted, at an ejection port 3640 in the end cap. The distal end of the constrictor and the ejection port in the end cap allow for ejection of the pressurized hydrodissecting fluid to effect the hydrodissection as the medical professional navigates the distal end 3460 through the space.

The skilled person should note that while it is preferred that the end cap 3600 is formed of transparent material, and as cylindrically shaped, the end cap is not limited thereto. The end cap 3600 may be formed of translucent material as long as a portion facilitates image pick-up, for example, by a window portion 3610, in an end face 3620, through which a light signal comprising the image is allowed in. For that matter, the window portion could comprise a lens-like formation at imaging window 3610, which amplifies, filters or bends the incoming image signal. So, while the cystoscope might be a zero (0) degree cystoscope, the cystoscope could have a non-zero image angle, for example, zero (0) to ninety (90) degrees. For simplicity, however, a zero (o) degree cystoscope is preferred. And the end cap 3600 may be any shape that can accommodate the image pick-up end of the scope and the distal end 3635 of the constrictor 3630, arranged in an ejection port 3640 in an end face 3620 of the end cap (opposite an open proximal end 3615). The proximal end 3638 of the constrictor connects to or attaches to the fluid supply at the ejecting port 3468.

The end cap 3600 preferably is attached to the distal end 3460 of the elongate flexible endoscope body by friction fit. However, the end cap may be connected using connection means known to the skilled person, such as screw threads arranged on an inner cylindrical surface of the end cap and complementary finish threads arranged on an outer cylindrical surface proximate the distal end 3460 of the elongate flexible insertion cord or tube 3440. Where the finish threads are arranged depends upon the length or the end cap, and according, how far the open proximal end of the end cap extends over and beyond the distal end 3460 of the insertion part. The connecting means cannot interfere with or otherwise denigrate the imaging field for capture of the image signal by the image pick-up device 3465.

Please note that while the exemplary cystoscope that is modified according to the invention comprises an elongate flexible insertion cord or tube 3440, bending section or maneuverable part 3450, and distal or working end 3460, the invention may include a means for converting the cystoscope to a substantially rigid elongate insertion cord or tube with the bending section or maneuverable part and distal or working end, or to a substantially rigid elongate insertion cord or tube and distal or working end without a bending section or maneuverable part.

The means for converting may comprise a simple substantially rigid tube 3660 (FIG. 36C) with an inside diameter substantially equivalent or slightly larger than the 6 mm outer diameter of the conventional tube or cord 3440. Bending section 3450 and distal end 3460 (example, 0.5 mm, 1 mm (preferably). The substantially rigid tube 3660 is arranged to connect to a distal end 3415 of the handle 3410 at a proximal end 3665 of the tube, and to the end cap 3600 at a distal end 3670 of the tube. Preferably, the inside diameter of the tube 3660 is substantially the same or 0.5 or mm greater that the outside diameter of the tube/cord 3460, bending section 3450 and distal end 3460, as the case may be. This is to ensure that the contacting inner rigid tube inner surfaces and the outer cystoscope outer surface 3411 display minimal friction therebetween so that the insertion cord or tube 3440 will readily slip into the inner space for the entire length to the handle distal end 3415. The substantially rigid tube 3660 as implied adds rigidity to the flexible and bending portions of the entire insertion portion. This allows a practitioner to manage the positioning of the distal end 3460, with the end cap 3600 attached, by articulating the handle 3410 opposite the distal end. The end cap 3600, in the embodiment of the rigid tube, preferably connects to or is formed with the rigid tube, whereby the rigid tube 3660 and end cap slide over the distal end 3460 and up to and in order to connect to the distal end 3415 of the handle 3410 (for rigidity) so that the distal end 3460 is arranged in the internal volume of the end cap 3600, as described.

For that matter, the length of the rigid tube 3660 preferably is sized to extend and to cover the flexible tube 3440, the bending section or maneuverable part 3450 and the distal end 3460. In either case, the outer surfaces of the substantially rigid tube proximate the distal end 3670 (depending on the length of the end cap 3600) and at the proximal end 3665 may be formed with screw threads 3675, 3680 that complement screw-type threads provided on the inner surface of the end cap 3600 and on an inner surface of a shoulder or insertion port at a distal end 3415 of handle 3410. Please note that in a case where the outer surface of the distal end 3415 of handle 3410 is modified with screw-type threads the inner surface at the proximal end 3665 may be threaded. Likewise, the inner surface of the proximal end 3615 of the end cap 3600 may have screw-type threads 3685 to effect attachment. In lieu of screw-type threads, the attachments may be friction with, with appropriate-sized complementary outer and inner surface diameters.

Figure 36D:
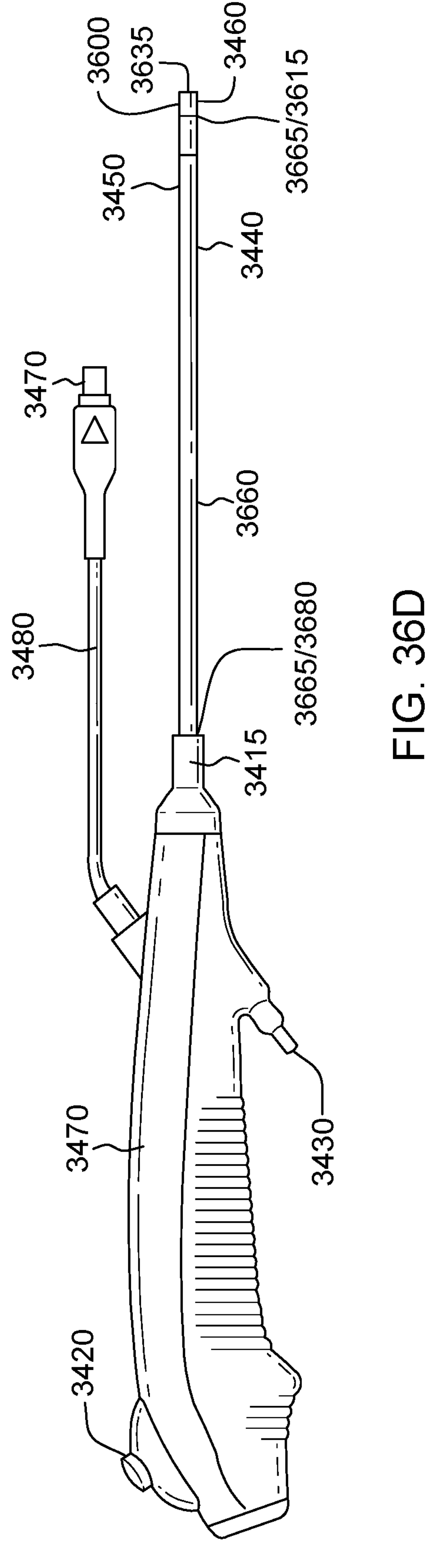
FIG. 36D shows a representation of an embodiment of an inventive, modified cystoscope with the rigid tube attached at the handle, the end cap 3600 attached proximate the distal end of the rigid tube and covering and sealingly housing the distal end 3460 of the insertion tube or cord.

FIG. 36D shows a representation of an embodiment of an inventive, modified cystoscope 3690 with the rigid tube 3660 attached at the handle (at proximal end 3665), the end cap 3600 attached proximate the distal end 3670 of the rigid tube and covering and sealingly housing the distal end 3460 of the insertion tube or cord 3440 such that the distal end 3635 of the fluid constrictor 3630, or the ejecting port 3468 at the distal end of the fluid supply or conduit is capable of ejecting the hydrodissecting fluid as a sufficient velocity or pressure to effect the hydrodissection. The hydrodissecting fluid post hydrodissection is maintained in a space created between the hydrodissected target vessel and the separated surrounding tissue as a tumescent treatment fluid for maintaining and treating the endothelium and outer tissues comprising the hydrodissected vessel. And while the axial length of the end cap 3600 (FIGS. 36A and 36B) preferably is 1 inch, the length is not limited thereto but may be in a range of 0.25 inch to 4.00 inches.

The present disclosure, in connection with the accompanied drawings, describes example configurations that are not representative of all the examples that may be implemented or all configurations that are within the scope of this disclosure. The term "exemplary" should not be construed as "preferred" or "advantageous compared to other examples" but rather "an illustration, an instance or an example." By reading this disclosure, including the description of the embodiments and the drawings, it will be appreciated by a person of ordinary skills in the art that the technology disclosed herein may be implemented using alternative embodiments. The person of ordinary skill in the art would appreciate that the embodiments, or certain features of the embodiments described herein, may be combined to arrive at yet other embodiments for practicing the technology described in the present disclosure. Thus, the disclosure is not limited to the examples and designs described herein but is to be accorded the broadest scope consistent with the principles and novel features disclosed herein.

INCORPORATION BY REFERENCE

The present application claims priority to U.S. Provisional Patent Application Nos. 62/533,714 filed on Jul. 18, 2017, 62/640,892 filed on Mar. 9, 2018, 62/683,376 filed Jun. 11, 2018, 63/300,206 filed on Jan. 17, 2022 and 63/328,413 filed on Apr. 7, 2022, the disclosures of which are incorporated herein by reference.

What is claimed is:

1. An endoscopic hydrodissector for atraumatically hydrodissecting a vascular target, the hydrodissector comprising:

a handle;

an elongate endoscopic tube attached to or integral with the handle at a proximal end of the elongate endoscopic tube with a working port or opening at a distal end of the elongate endoscopic tube;

a hydrodissecting shell with a distal end and a proximal end, the hydrodissecting shell configured for attachment to an outer surface of the elongate endoscopic tube, wherein a fluid ejection port is arranged at the distal end of the hydrodissecting shell in fluid-flow connection to a fluid conduit or channel in an inner volume of the hydrodissecting shell that is in fluid-flow connection to a fluid supply for supplying hydrodissecting fluid for ejection from the fluid ejection port to hydrodissect and substantially separate the vascular target from tissues surrounding the vascular target, creating a substantially hydrodissecting fluid-filled space therebetween;

wherein the working port or opening of the elongate endoscopic tube and the fluid ejection port of the attached hydrodissecting shell are inserted into an incision space formed by making an incision into the tissue proximate a proximal end of the vascular target and controlled to move through the incision space and create a created space by hydrodissecting to separate the vascular target from the tissues surrounding the vascular target and enlarging the created space as the elongate endoscopic tube with working port or opening and hydrodissecting shell with the fluid ejection port to traverse the created space to the distal end of the vascular target; and wherein the hydrodissecting fluid is formulated to minimize or prevent formation of microthrombi in the endothelium of the hydrodissected vascular target.

2. The hydrodissector of claim 1, wherein the fluid is formulated with a vascular graft treatment solution to maintain endothelial function and structure of the vascular target.

3. The hydrodissector of claim 2, wherein the hydrodissecting fluid further includes at least one of aspirin and low molecular weight heparin.

4. The hydrodissector of claim 1, wherein the hydrodissecting fluid supply provides sufficient pressure and velocity to the hydrodissecting fluid ejected to effect the hydrodissection.

5. The hydrodissector of claim 1, further comprising a short blunt tip (SBT) cannula with an insertion end, a fluid seal end, and a side port, wherein the insertion end is inserted partially into the incision to form a fluid barrier to prevent or minimize fluid leakage and the side port acts as as the hydrodissecting shell input port.

6. The hydrodissector of claim 1, wherein at or near the working port or opening at the distal end of the elongate endoscopic tube, an image capture assembly or device is provided for direct visualization while the elongate endoscopic tube and attached hydrodissecting shell are navigated under direct vision to hydrodissect the vascular target and divide branches using a cautery device that extends from the the working opening.

7. The hydrodissector of claim 1, wherein the elongate endoscopic tube embodies a rigid cannula.

8. The hydrodissector of claim 7, wherein the fluid supply is maintained in a housing, separate from the hydrodissecting shell, wherein the hydrodissecting shell is detachably connected to an outer surface of the cannula and wherein the hydrodissecting fluid is ejected from the fluid ejection port arranged in a distal end of the hydrodissecting shell proximate the working tip.

9. The hydrodissector of claim 8, wherein the elongate endoscopic tube includes a bending portion comprising a first end and a second end, wherein the first end is attached to or integral with a truncated end of the flexible, elongate endoscopic tube and wherein the second end is attached to or integral with the working tip.

10. The hydrodissector of claim 9, wherein the handle includes a manipulating means coupled or connected to the bending portion, to control articulation of the bending portion and a position of the working tip with the ejection port and thereby a direction to which the fluid is directed to effect hydrodissection.

11. The hydrodissector of claim 9, wherein the hydrodissecting shell is detachably connected to the outer surface of the elongate endoscopic tube such that the working tip is positioned proximate the distal end of the hydrodissecting shell when the hydrodissecting shell is detachably connected to the elongate endoscopic tube.

12. The hydrodissector of claim 6, further comprising a portable display detachably connectable to the image capture device for capturing and displaying an image signal to support atraumatic hydrodissection.

13. A method of atraumatically hydrodissecting a vascular target from a proximal end to a distal end, or vice versa, while maintaining an endothelial function and structure of the vascular target, comprising the steps of:

forming an insertion space in tissue proximate the proximal end of the vascular target and inserting a distal end of a cannula with an endoscope arranged in an inner volume thereof, into the insertion space wherein the cannula with endoscope includes a working tip with an image pick-up device and an input port for connecting to a fluid supply means and a hydrodissecting port for ejecting a hydrodissecting fluid;

visualizing the vascular target and cannula with endoscope with an image signal captured by the image pick-up device while advancing the cannula with endoscope and working tip to the distal end of the vascular target while ejecting the hydrodissecting fluid to substantially separate or dissect the vascular target from the surrounding tissues and creating a created space, which is enlarged as the cannula with endoscope and working tip are advanced towards the distal end of the vascular target;

wherein the hydrodissecting fluid is formulated to minimize or prevent formation of microthrombi in the endothelium of the hydrodissected vascular target.

14. The method of claim 13, wherein the hydrodissecting fluid is a water-based vascular graft treatment solution that comprises water and one or more of a balanced salt solution, metallic salt solution, vascular graft treatment solution, L-Arginine, aspiring and low molecular weight heparin.

15. The method of claim 13, further including, after hydrodissecting the vascular target, dividing and/or sealing branches of the vascular target and substantially closing the incision space and the created space while some portion of hydrodissecting fluid is maintained as a tumescent fluid in or is otherwise introduced to the created space and remains in the created space during harvesting wherein side branches of the hydrodissected vascular target are separated from the vascular target under direct vision.

16. The method of claim 13, wherein during harvesting all side branches extending from the vascular target are divided and sealed and the distal and proximal ends of the vascular target are ligated to atraumatically extract the vascular target from the created space.

* * * * *